(12) United States Patent  (10) Patent No.: US 8,937,080 B2
Raboisson et al. (45) Date of Patent: Jan. 20, 2015

(54) PYRIMIDINE SUBSTITUTED MACROCYCLIC HCV INHIBITORS

(75) Inventors: Pierre Jean-Marie Bernard Raboisson, Rosieres (BE); Anna Karin Gertrud Linnea Belfrage, Huddinge (SE); Björn Olof Classon, Huddinge (SE); Karin Charlotta Lindquist, Huddinge (SE); Karl Magnus Nilsson, Huddinge (SE); Åsa Annica Kristina Rosenquist, Huddinge (SE); Bertil Bengt Samuelsson, Huddinge (SE); Horst Jürgen Wähling, Huddinge (SE)

(73) Assignees: Medivir AB, Huddinge (SE); Janssen R&D Ireland, Co Cork (IE)

( * ) Notice: Subject to any disclaimer, the term of this patent is extended or adjusted under 35 U.S.C. 154(b) by 459 days.

(21) Appl. No.: 12/526,553

(22) PCT Filed: Feb. 8, 2008

(86) PCT No.: PCT/EP2008/051553
§ 371 (c)(1),
(2), (4) Date: Aug. 10, 2009

(87) PCT Pub. No.: WO2008/095999
PCT Pub. Date: Aug. 14, 2008

(65) Prior Publication Data
US 2010/0113440 A1   May 6, 2010

(30) Foreign Application Priority Data
Feb. 8, 2007 (EP) .................................. 07102005

(51) Int. Cl.
  *A61K 31/506*  (2006.01)
  *C07D 245/02*  (2006.01)
  *C07K 5/078*  (2006.01)
  *C07D 403/12*  (2006.01)
  *A61K 38/00*  (2006.01)

(52) U.S. Cl.
  CPC .......... *C07K 5/06165* (2013.01); *C07D 403/12* (2013.01); *A61K 38/00* (2013.01)
  USPC .......................................... 514/269; 540/460

(58) Field of Classification Search
  USPC .......................................... 514/269; 540/460
  See application file for complete search history.

(56) References Cited

U.S. PATENT DOCUMENTS

| 5,484,801 | A | 1/1996 | Al-Razzak et al. |
| 6,037,157 | A | 3/2000 | Norbeck et al. |
| 7,741,281 | B2 * | 6/2010 | D'Andrea et al. ............ 424/85.4 |
| 7,989,471 | B2 * | 8/2011 | Simmen et al. ............... 514/309 |

FOREIGN PATENT DOCUMENTS

| WO | 94/14436 A1 | 7/1994 |
| WO | 95/07696 A1 | 3/1995 |
| WO | 95/09614 A1 | 4/1995 |
| WO | 98/17679 A1 | 4/1998 |
| WO | 98/22496 A2 | 5/1998 |
| WO | 99/07734 A2 | 2/1999 |
| WO | 02/18369 A2 | 3/2000 |
| WO | 00/56331 A1 | 9/2000 |
| WO | 03099274 A1 | 12/2003 |
| WO | WO 2005/073195 | 8/2005 |
| WO | WO2005073216 A2 | 8/2005 |
| WO | WO 2007/014919 | 2/2007 |
| WO | WO 2007/014925 | 2/2007 |
| WO | WO 2007014927 | * 2/2007 |

OTHER PUBLICATIONS

Bryn, Solid State Chemistry of Drugs, 2nd edition, 1999, SSCI. Inc, Chapter 10, Polymorphs, p. 232-247.*
Bryn, et al., Hydrates and Solvates, Solid State Chemistry of Drugs, 1999, chapter 11, pp. 232-247, 2nd edition, US.
Miller, S.J., et al., "Application of Ring-Closing Metathesis to the Synthesis of Rigidified Amino Acids and peptides" J. Am. Chem. Soc. 118, (1996), 9606-9614.
Kingsbury, J.S., et al., "A Recyclable Ru-Based Methathesis Catalyst", J. Am. Chem. Soc. 121, (1999), 791-799.
Huang et al., "Olefin Methathesis-Active Ruthemium Complexes Bearing a Nucleophilic Carbene Ligand", J. Am. Chem. Soc. 121, (1999), 2674-2678.
Smith, E.M. et al., "Synthesis and Pharmacological Activity of Angiotensin Converting Enzyme Inhibitors: N-(Mercaptoacyl)-4-substituted-(S)-proline", J. Med. Chem. (1988), 31, 875-885.

(Continued)

*Primary Examiner* — Rebecca Anderson
*Assistant Examiner* — Karen Cheng
(74) *Attorney, Agent, or Firm* — Andrea Jo Kamage

(57) ABSTRACT

Compounds of the formula I:

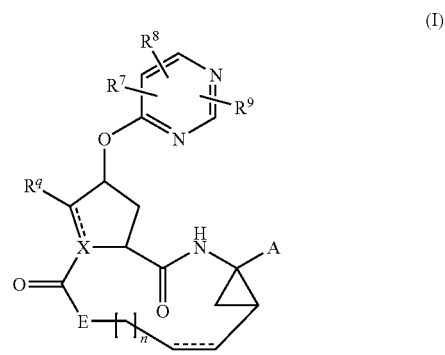

including a stereoisomer thereof, or an N-oxide, a pharmaceutically acceptable addition salt, or a pharmaceutically acceptable addition solvate thereof; useful as HCV inhibitors; processes for preparing these compounds as well as pharmaceutical compositions comprising these compounds as active ingredient.

13 Claims, No Drawings

(56) References Cited

OTHER PUBLICATIONS

Oyo Mitsunobu, "The Use of Diethyl Azodicarboxylate and Triphenylphosphine in Synthesis and Transformation of Nature Products", Synthesis, Jan. 1-28; 1981.

Krchnak et al., "Polymer-Supported Mitsunobu Ether Formation and its Use in Combinatorial Chemistry", Tetrahedron Letters, 1995, 36, 5, 6193-6196.

Richter et al., "A Surprising Observation about Mitsunobu Reactions in Solid Phase Synthesis", Tetrahedron Lett., 1994, 35, 27, 4705-4706.

Dolby et al. "Studies of the Synthesis of the B, C, and D Rings of Gibberellic Acid", J. Org. Chem. 36 (1971) 1277-1285.

Lohmann et al. "Replication of Subgenomic Hepatitis C Virus RNAs in a Hepatoma Cell Line", (1999) Science 285:110-113.

Krieger et al. "Enhancement of Hepatitis C Virus RNA Replication by Cell Culture-Adaptive Mutations", (2001) Journal of Virology 75: 4614-4624.

Rano et al., "Solid Phase Synthesis of Aryl Ethers Via The Mitsunobu Reaction", Tetrahedron Letters, 1995, 36, 22, 3779-3792.

* cited by examiner

PYRIMIDINE SUBSTITUTED MACROCYCLIC HCV INHIBITORS

CROSS REFERENCE TO RELATED APPLICATIONS

This application is the national stage of PCT Application No. PCT/EP2008/051553 filed Feb. 8, 2008, which claims priority from European Patent Application No. 07102005.1, filed Feb. 8, 2007, the entire disclosures of which are hereby incorporated in their entirety.

TECHNICAL FIELD

This invention relates to macrocyclic compounds having inhibitory activity on the NS3 serine protease of HCV. It further concerns compositions comprising these compounds as active ingredients as well as processes for preparing these compounds and compositions.

BACKGROUND OF THE INVENTION

Hepatitis C virus (HCV) is the leading cause of chronic liver disease worldwide and has become a focus of considerable medical research. HCV is a member of the Flaviviridae family of viruses in the hepacivirus genus, and is closely related to the flavivirus genus, which includes a number of viruses implicated in human disease, such as dengue virus and yellow fever virus, and to the animal pestivirus family, which includes bovine viral diarrhea virus (BVDV). The genome of HCV comprises both 5' and 3' untranslated regions that adopt RNA secondary structures, and a central open reading frame that encodes a single polyprotein. The polyprotein encodes ten gene products, which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are differently distributed geographically. HCV type 1 is the predominant genotype in Europe and the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better-tolerated treatments.

A number of similar HCV protease inhibitors have been disclosed in the academic and patent literature. The sustained administration of HCV protease inhibitors usually leads to the selection of resistant HCV mutants, so called drug escape mutants. These have characteristic mutations in the HCV protease genome, notably D168V, D168Y and/or A165S. Accordingly, there is a need for additional drugs with different resistance patterns to provide failing patients with treatment options. Such drugs may find use in combination therapy, which is expected to become the norm in the future, even for first line treatment.

Experience with HIV drugs, in particular with HIV protease inhibitors, has taught that sub-optimal pharmacokinetics and complex dosing regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants.

Achieving the necessary pharmacokinetics and drug metabolism to allow such trough levels provides a stringent challenge to drug design. Known HCV protease inhibitors, with multiple peptide bonds, pose additional pharmacokinetic hurdles to effective dosage regimes.

There is a need for HCV inhibitors that may overcome the disadvantages of current HCV therapy such as side effects, limited efficacy, the emerging of resistance, and compliance failures.

The present invention concerns inhibitors of HCV replication that exhibit at least one improved property in view of the compounds of the prior art compounds. In particular, the inhibitors of the present invention are superior in one or more of the following pharmacological related properties, i.e. potency, decreased cytotoxicity, improved pharmacokinetics, improved resistance profile, acceptable dosage and pill burden. The HCV inhibitors of the present invention are particularly attractive due to their good activity against mutant HCV strains.

BRIEF DESCRIPTION OF THE INVENTION

The present invention concerns inhibitors of HCV replication, which can be represented by formula (I):

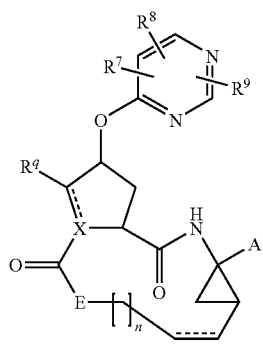

(I)

wherein

A is —C(=O)OR¹, —C(=O)—NH—SO₂—R², —C(=O)C(=O)NR³ᵃR³ᵇ, —C(=O)—NH—SO₂—NR³ᵃR³ᵇ, —C(=O)NH—P(=O)(OR⁴ᵃ)(R⁴ᵇ), or —P(=O)(OR⁴ᵃ)(R⁴ᵇ) wherein;

R¹ is hydrogen; aryl; Het; C₃₋₇cycloalkyl optionally substituted with C₁₋₆alkyl; or C₁₋₆alkyl optionally substituted with C₃₋₇cycloalkyl, aryl or with Het;

R² is aryl; Het; C₃₋₇cycloalkyl optionally substituted with C₁₋₆alkyl; or C₁₋₆alkyl optionally substituted with C₃₋₇cycloalkyl, aryl, or with Het;

each R³ᵃ and R³ᵇ independently are hydrogen; C₁₋₆alkyl optionally substituted with C₁₋₆alkoxy, hydroxy, halo, C₃₋₇cycloalkyl, aryl, or with Het; aryl; C₂₋₆alkenyl; Het; C₃₋₇cycloalkyl optionally substituted with C₁₋₆alkyl; or R³ᵃ and R³ᵇ together with the nitrogen atom to which they are attached form a group Het¹; and R³ᵃ may also be C₁₋₆alkoxy;

R⁴ᵃ is hydrogen, C₁₋₆alkyl, C₂₋₆alkenyl, C₃₋₇cycloalkyl, aryl, or C₁₋₆alkyl optionally substituted with C₃₋₇cycloalkyl or aryl;

R⁴ᵇ is R⁴ᵇ′, OR⁴ᵇ′ or NHR⁴ᵇ′;

R⁴ᵇ′ is C₁₋₆alkyl, C₂₋₆alkenyl, C₃₋₇cycloalkyl, aryl, or C₁₋₆alkyl optionally substituted with C₃₋₇cycloalkyl or with aryl;

X is N, CH and when X bears a double bond it is C;

Rᵍ is hydrogen, or where X is C or CH, Rᵍ may also be C₁₋₆alkyl;

E is NR⁵ or when X is N then E is NR⁵ or CR⁶ᵃR⁶ᵇ;

R⁵ is hydrogen, C₁₋₆alkyl, C₁₋₆alkoxyC₁₋₆alkyl, or C₃₋₇cycloalkyl;

R⁶ᵃ and R⁶ᵇ are independently hydrogen or C₁₋₆alkyl, or R⁶ᵃ and R⁶ᵇ together with the carbon atom to which they are attached form C₃₋₇cycloalkyl;

n is 3, 4, 5 or 6;

each dotted line ----- independently represents an optional double bond;

R⁷ and R⁸ independently are C₁₋₆alkyl optionally substituted with C₁₋₆alkoxy, —NRᵃRᵇ, hydroxy, halo, C₃₋₇cycloalkyl, or with aryl; C₃₋₇cycloalkyl; aryl; Het; C₂₋₆alkenyl; C₁₋₆alkoxy; C₃₋₇cycloalkyloxy; aryloxy; Het-O—; hydroxy; cyano; halo; polyhalo-C₁₋₆alkyl; —NRᵃRᵇ; and R⁷ may also be hydrogen;

R⁹ is hydrogen or C₁₋₆alkyl;

Rᵃ is H, C₁₋₆alkyl, C₁₋₆alkoxy;

Rᵇ is H; C₃₋₇cycloalkyl; C₁₋₆alkyl optionally substituted with C₃₋₇cycloalkyl or aryl; or Ra and Rb together with the nitrogen atom to which they are attached form Het¹;

each aryl independently is phenyl optionally substituted with one, two or three substituents selected from halo, hydroxy, nitro, cyano, carboxyl, C₁₋₆alkyl, C₁₋₆alkoxy, C₁₋₆alkoxyC₁₋₆alkyl, C₁₋₆alkylcarbonyl, amino, mono- or diC₁₋₆alkyl-amino, azido, mercapto, C₁₋₆alkylthio, polyhaloC₁₋₆alkyl, polyhaloC₁₋₆alkoxy, C₃₋₇cycloalkyl, and Het¹;

each Het independently is a 5 or 6 membered saturated, partially unsaturated or completely unsaturated heterocyclic ring containing 1, 2, 3 or 4 heteroatoms each independently selected from nitrogen, oxygen and sulfur, said heterocyclic ring being optionally substituted with one, two or three substituents each independently selected from halo, hydroxy, nitro, cyano, carboxyl, C₁₋₆alkyl, C₁₋₆alkoxy, C₁₋₆alkoxyC₁₋₆alkyl, C₁₋₆alkylcarbonyl, amino, mono- or diC₁₋₆alkylamino, azido, mercapto, polyhaloC₁₋₆alkyl, polyhaloC₁₋₆alkoxy, C₃₋₇cycloalkyl, Het¹;

each Het¹ independently is pyrrolidinyl, piperidinyl, piperazinyl, 4-C₁₋₆alkyl-piperazinyl, 4-C₁₋₆alkylcarbonyl-piperazinyl, and morpholinyl and wherein the morpholinyl and piperidinyl groups may optionally substituted with one or two C₁₋₆alkyl radicals;

or the N-oxides, pharmaceutically acceptable addition salts, or stereoisomers thereof.

The invention further relates to methods for the preparation of the compounds of formula (I) as well as the use of the intermediates in the preparation of the compounds of formula (I).

The invention relates to the compounds of formula (I) per se, and the N-oxides, pharmaceutically acceptable addition salts, and stereochemically isomeric forms thereof, for use as a medicament. The invention further relates to pharmaceutical compositions comprising the aforementioned compounds for administration to a subject suffering from HCV infection. The pharmaceutical compositions may comprise combinations of the aforementioned compounds with other anti-HCV agents.

The invention also relates to the use of a compound of formula (I), an N-oxide, a pharmaceutically acceptable addition salt, or stereochemically isomeric form thereof, for the manufacture of a medicament for inhibiting HCV replication. Or the invention relates to a method of inhibiting HCV replication in a warm-blooded animal, said method comprising the administration of an effective amount of a compound of formula (I), an N-oxide, a pharmaceutically acceptable addition salt, or stereochemically isomeric form thereof.

DETAILED DESCRIPTION OF THE INVENTION

As used in the foregoing and hereinafter, the following definitions apply unless otherwise noted.

As used herein "C₁₋₄alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "C₁₋₆alkyl" encompasses C₁₋₄alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst C₁₋₆alkyl is C₁₋₄alkyl.

The term "C₂₋₆alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst C₂₋₆alkenyl is C₂₋₄alkenyl.

$C_{3-7}$cycloalkyl is generic to cyclopropyl, cyclobutyl, cyclopentyl, cyclohexyl and cycloheptyl.

$C_{1-6}$alkoxy means $C_{1-6}$alkyloxy wherein $C_{1-6}$alkyl is as defined above and is bonded to an oxygen atom, i.e. —O—$C_{1-6}$alkyl. Of interest amongst $C_{1-6}$alkoxy are methoxy, ethoxy and propoxy.

The term halo is generic to fluoro, chloro, bromo and iodo, in particular fluoro or chloro.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoro-ethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

As used herein before, the term (=O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a saturated carbon.

The radical Het is a heterocycle as specified in this specification and claims. Examples of Het comprise, for example, pyrrolidinyl, piperidinyl, morpholinyl, thiomorpholinyl, piperazinyl, pyrrolyl, pyrazolyl, imidazolyl, oxazolyl, isoxazolyl, thiazinolyl, isothiazinolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, triazinyl, and the like. Of interest amongst the Het radicals are those which are non-saturated, in particular those having an aromatic character. Of further interest are those Het radicals having one or two nitrogens.

Each of the Het radicals mentioned in this and the following paragraph may be optionally substituted with the number and kind of substituents mentioned in the definitions of the compounds of formula (I) or any of the subgroups of compounds of formula (I). Some of the Het radicals mentioned in this and the following paragraph may be substituted with one, two or three hydroxy substituents. Such hydroxy substituted rings may occur as their tautomeric forms bearing keto groups. For example a 3-hydroxypyridazine moiety can occur in its tautomeric form 2H-pyridazin-3-one. Where Het is piperazinyl, it preferably is substituted in its 4-position by a substituent linked to the 4-nitrogen with a carbon atom, e.g. 4-$C_{1-6}$alkyl, 4-polyhalo$C_{1-6}$alkyl, $C_{1-6}$alkoxy$C_{1-6}$alkyl, $C_{1-6}$alkylcarbonyl, $C_{3-7}$cycloalkyl.

Interesting Het radicals comprise, for example pyrrolidinyl, piperidinyl, morpholinyl, thiomorpholinyl, piperazinyl, pyrrolyl, pyrazolyl, imidazolyl, oxazolyl, isoxazolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, or any of such heterocycles condensed with a benzene ring, such as indolyl, indazolyl (in particular 1H-indazolyl), indolinyl, quinolinyl, tetrahydroquinolinyl (in particular 1,2,3,4-tetrahydroquinolinyl), isoquinolinyl, tetrahydroisoquinolinyl (in particular 1,2,3,4-tetrahydroisoquinolinyl), quinazolinyl, phthalazinyl, benzimidazolyl, benzoxazolyl, benzisoxazolyl, benzothiazolyl, benzoxadiazolyl, benzothiadiazolyl, benzofuranyl, benzothienyl.

The Het radicals pyrrolidinyl, piperidinyl, morpholinyl, thiomorpholinyl, piperazinyl, 4-substituted piperazinyl preferably are linked via their nitrogen atom (i.e. 1-pyrrolidinyl, 1-piperidinyl, 4-thiomorpholinyl, 4-morpholinyl, 1-piperazinyl, 4-substituted 1-piperazinyl).

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar terms, it is meant to include the compounds of formula (I), their N-oxides, pharmaceutically acceptable addition salts, and stereochemically isomeric forms. One embodiment comprises the compounds of formula (I) or any subgroup of compounds of formula (I) specified herein, and the pharmaceutically acceptable addition salts and the possible stereoisomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e., minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound are synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), the N-oxides, the pharmaceutically acceptable addition salts, and solvates thereof, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The pharmaceutically acceptable addition salts comprise the therapeutically active non-toxic acid and base addition salt forms of the compounds of formula (I). The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salts also is meant to comprise the solvates, which the compounds of formula (I) as well as the salts thereof, are able to form. Such solvates are for example hydrates, alcoholates, e.g. ethanolates, propanolates, and the like.

The N-oxide forms of the present compounds are meant to comprise the compounds of formula (I) wherein one or several nitrogen atoms are oxidized to a so-called N-oxide.

Some of the compounds of formula (I) may also exist in their tautomeric form. Such forms although not explicitly indicated in the above formula are intended to be included within the scope of the present invention.

As mentioned above, the compounds of formula (I) have several asymmetric centers. In order to more efficiently refer to each of these asymmetric centers, the numbering system as indicated in the following structural formula will be used.

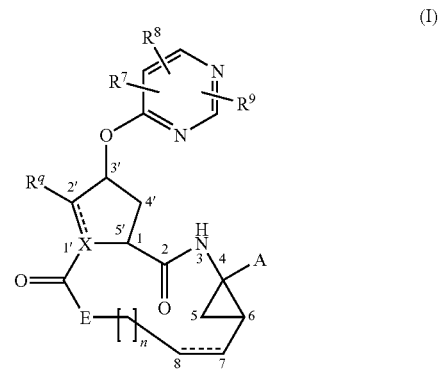

Asymmetric centers are present at positions 1, 4 and 6 of the macrocycle as well as at the carbon atom 3' in the 5-membered ring, at carbon atom 2' when the $R^q$ substituent is $C_{1-6}$alkyl, and at carbon atom 1' when X is CH. Each of these asymmetric centers can occur in their R or S configuration.

When X is N, the stereochemistry at position 1 preferably corresponds to that of an L-amino acid configuration, i.e. that of L-proline as shown below.

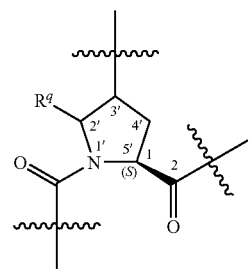

When X is CH, the 2 carbonyl groups substituted at positions 1' and 5' of the cyclopentane ring preferably are in a trans configuration. The carbonyl substituent at position 5' preferably is in that configuration that corresponds to an L-proline configuration. The carbonyl groups substituted at positions 1' and 5' preferably are as depicted below in the structure of the following formula:

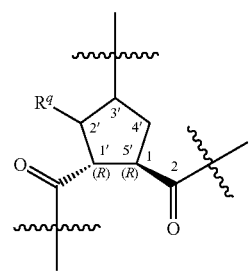

The compounds of formula (I) include a cyclopropyl group as represented in the structural fragment below:

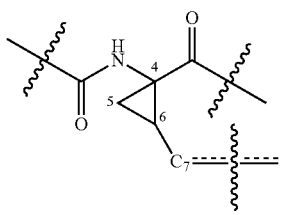

wherein $C_7$ represents the carbon at position 7 and carbons at position 4 and 6 are asymmetric carbon atoms of the cyclopropane ring. The presence of these two asymmetric centers means that the compounds can exist as mixtures of diastereomers, such as the diastereomers of compounds of formula (I) wherein the carbon at position 7 is configured either cis to the carbonyl or cis to the amide as shown below.

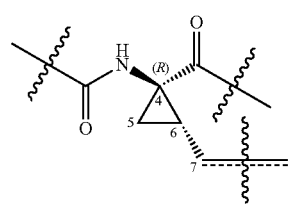
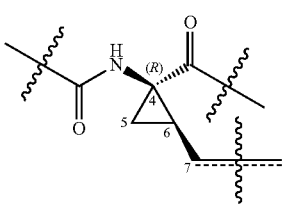

C7 cis to carbonyl     C7 cis to amide

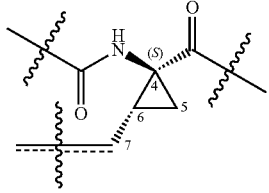
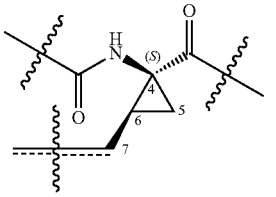

C7 cis to carbonyl     C7 cis to amide

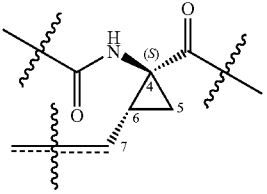

C7 cis to carbonyl

One embodiment concerns compounds of formula I wherein the carbon at position 7 is configured cis to the carbonyl. Another embodiment concerns compounds of formula (I) wherein the configuration at the carbon at position 4 is R. A specific subgroup of compounds of formula (I) is that wherein the carbon at position 7 is configured cis to the carbonyl and wherein the configuration at the carbon at position 4 is R.

According one embodiment the cyclopropyl group ($C_4$-$C_5$-$C_6$) is linked to a group A that is a phosphonate group —P(=O)(OR$^{4a}$)(R$^{4b}$). According to this embodiment, the carbon at position 7 is configured in a cis relationship either to the phosphonate or to the amide as presented in the structural fragment below:

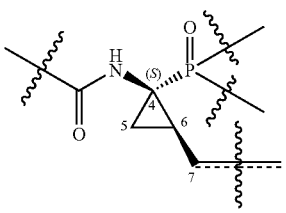

C7 cis to phosphonate     C7 cis to amide

C7 cis to phosphonate     C7 cis to amide

One embodiment concerns compounds of formula (I) wherein the carbon at position 7 is configured cis to the phosphonate. Another embodiment concerns compounds of formula (I) wherein the configuration at the carbon at position 4 is S. A specific subgroup of compounds of formula (I) are those wherein the carbon at position 7 is configures cis to the phosphonate and wherein the configuration at the carbon at position 4 is S.

The compounds of formula (I) may include a proline residue i.e. X is N, or a cyclopentyl or cyclopentenyl residue, i.e. X is CH or C respectively. According to one embodiment of this invention the compounds comprise the partial structures:

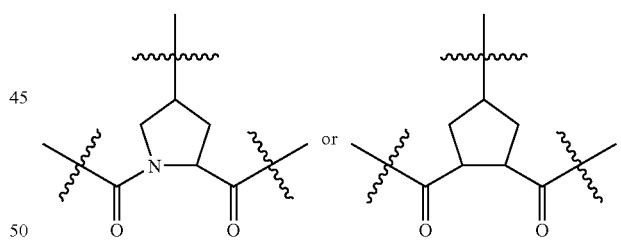

Further embodiments of the invention are compounds of formula (I) or any of the subgroups of compounds of formula (I), wherein R$^q$ is methyl, E is NR$^5$, X is CRz and Rz forms a double bond with the carbon bearing R$^q$.

Preferred are the compounds of formula (I) wherein the substituent at the 1 (or 5') position and the ether-linked pyrimidine substituent at position 3' are in a trans configuration. Of particular interest are the compounds of formula (I) wherein position 1 has the configuration corresponding to L-proline and the ether linked pyrimidine substituent at position 3' is in a trans configuration in respect of position 1.

Preferably the compounds of formula (I) have the stereochemistry as indicated in the structures of formulae (I-a) and (I-b) below:

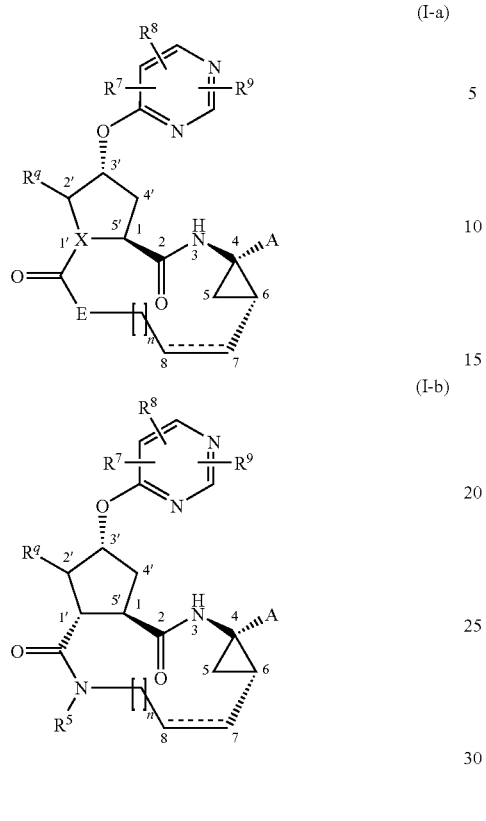

(I-a)

(I-b)

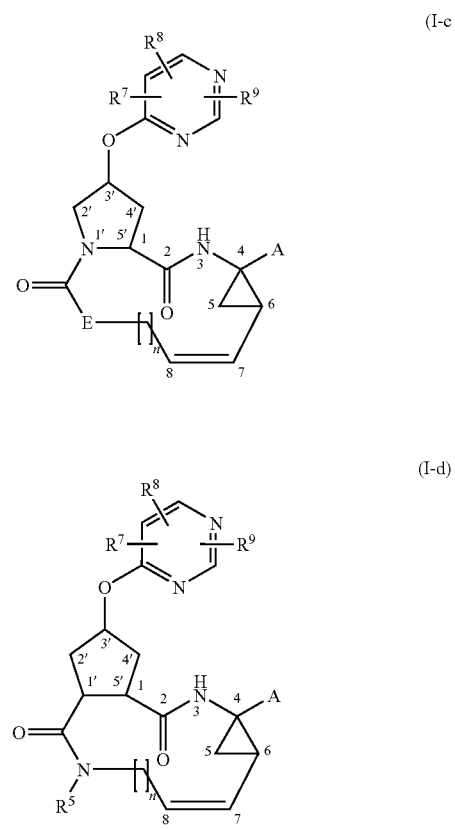

(I-c)

(I-d)

One embodiment of the present invention concerns compounds of formula (I) or of formula (I-a), (I-b) or of any subgroup of compounds of formula (I), wherein one or more of the following conditions apply:

(a) $R^q$ is hydrogen;
(b) X is nitrogen;
(c) E is $NR^5$;
(d) a double bond is present between carbon atoms 7 and 8.

A further embodiment of the present invention concerns compounds of formula (I) or of formulae (I-a), (I-b), or of any subgroup of compounds of formula (I), wherein one or more of the following conditions apply:

(a) $R^q$ is hydrogen;
(b) X is nitrogen;
(c) E is $CR^{6a}R^{6b}$;
(d) a double bond is present between carbon atoms 7 and 8.

A further embodiment of the present invention concerns compounds of formula (I) or of formulae (I-a), (I-b), or of any subgroup of compounds of formula (I), wherein one or more of the following conditions apply:

(a) $R^q$ is hydrogen;
(b) X is CH;
(c) E is $NR^5$, wherein $R^5$ is as defined above, particularly $R^5$ is hydrogen or $C_{1-6}$alkyl;
(d) a double bond is present between carbon atoms 7 and 8.

Particular subgroups of compounds of formula (I) are those represented by the structural formulae (I-c), (I-d) and (I-e) below:

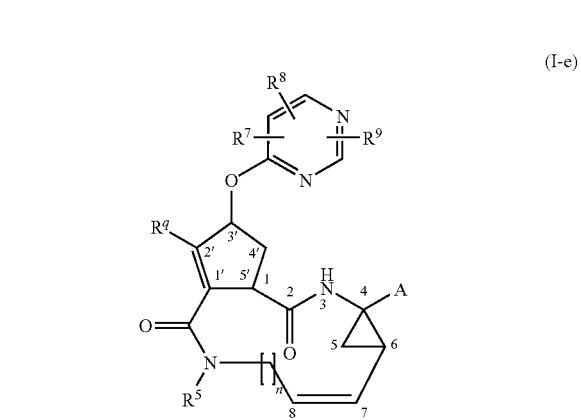

(I-e)

Amongst the compounds of formula (I-c), (I-d) and (I-e), those having the stereochemical configuration shown in formulae (I-a), and (I-b), respectively, are of particular interest.

The double bond between carbon atoms 7 and 8 in the compounds of formula (I), or in any subgroup of compounds of formula (I), may be in a cis or in a trans configuration. Preferably the double bond between carbon atoms 7 and 8 is in a cis configuration, as depicted in formulae (I-c), (I-d) and (I-e).

Other particular subgroups of compounds of formula (I) are those represented by the following structural formulae:

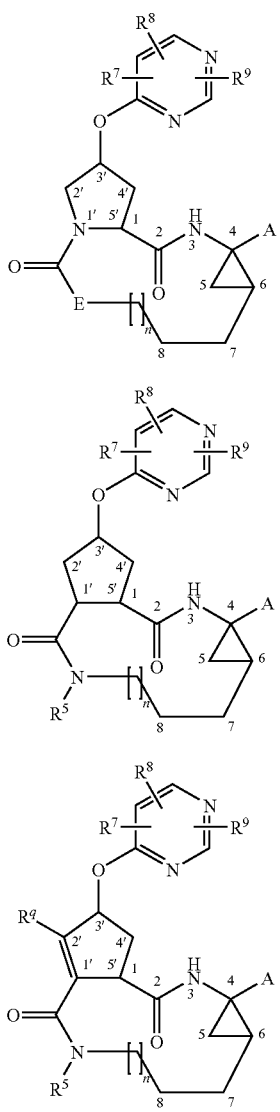

(I-f)

(I-g)

(I-h)

Of particular interest amongst the compounds of formulae (I-f), (I-g) or (I-h) are those having the stereochemical configuration of the compounds of formulae (I-a) and (I-b).

In (I-a), (I-b), (I-c), (I-d), (I-e), (I-f), (I-g) or (I-h), where applicable, A, E, X, n, $R^q$, $R^5$, $R^7$, $R^8$ and $R^9$ are as specified in the definitions of the compounds of formula (I) or of any of the subgroups of compounds of formula (I) specified herein.

It is to be understood that the above defined subgroups of compounds of formulae (I-a), (I-b), (I-c), (I-d) or (I-e), as well as any other subgroup defined herein, are meant to also comprise any N-oxides, addition salts, and stereochemically isomeric forms of such compounds.

When n is 2, the moiety —CH$_2$— bracketed by "n" corresponds to ethanediyl in the compounds of formula (I) or in any subgroup of compounds of formula (I). When n is 3, the moiety —CH$_2$— bracketed by "n" corresponds to propanediyl in the compounds of formula (I) or in any subgroup of compounds of formula (I). When n is 4, the moiety —CH$_2$— bracketed by "n" corresponds to butanediyl in the compounds of formula (I) or in any subgroup of compounds of formula (I). When n is 5, the moiety —CH$_2$— bracketed by "n" corresponds to pentanediyl in the compounds of formula (I) or in any subgroup of compounds of formula (I). When n is 6, the moiety —CH$_2$— bracketed by "n" corresponds to hexanediyl in the compounds of formula (I) or in any subgroup of compounds of formula (I). Particular subgroups of the compounds of formula (I) are those compounds wherein n is 4 or 5.

Embodiments of the invention are compounds of formula (I) or any of the subgroups of compounds of formula (I) wherein A is —C(=O)OR$^1$ in particular wherein R$^1$ is C$_{1-6}$alkyl, such as methyl, ethyl, or tert-butyl, and most preferably where R$^1$ is hydrogen.

A further embodiment of the invention are compounds of formula (I) or any of the subgroups of compounds of formula (I) wherein A is —C(=O)—NH—SO$_2$R$^2$, in particular wherein R$^2$ is C$_{3-7}$cycloalkyl, phenyl or a group Het, e.g. thiazolyl or pyridyl, either of which is optionally substituted with one or more, such as one or two substituents selected from C$_{1-6}$alkyl, C$_{1-6}$alkoxy, trifluoromethyl, and halo, or in particular with one or two substituents selected from methyl, fluoro and chloro. For example R$^2$ can be 1-methylcyclopropyl.

A further embodiment of the invention are compounds of formula (I) or any of the subgroups of compounds of formula (I) wherein A is —C(=O)C(=O)NR$^{3a}$R$^{3b}$, in particular wherein R$^{3a}$ and R$^{3b}$ are independently selected from hydrogen, C$_{1-6}$alkyl, optionally substituted with aryl, and C$_{2-6}$alkenyl. In one embodiment, one of R$^{3a}$ and R$^{3b}$ is hydrogen and the other is 3-propenyl, cyclopropylmethyl or cyclopropyl. In a further embodiment, R$^{3a}$ and R$^{3b}$ are both hydrogen.

A further embodiment of the invention are compounds of formula (I), or any of the subgroups of compounds of formula (I), wherein A is —C(=O)—NH—P(=O)(OR$^{4a}$)(R$^{4b}$), in particular wherein R$^{4a}$ is C$_{1-6}$alkyl, especially ethyl or isopropyl and R$^{4b}$ is OR$^{4b'}$ and R$^{4b'}$ is C$_{1-6}$alkyl, such as ethyl or isopropyl.

A further embodiment of the invention are compounds of formula (I), or any of the subgroups of compounds of formula (I), wherein A is —P(=O)(OR$^{4a}$)(R$^{4b}$), in particular wherein R$^{4a}$ is C$_{1-6}$alkyl, especially ethyl or isopropyl and R$^{4b}$ is OR$^{4b'}$ and R$^{4b'}$ is C$_{1-6}$alkyl, especially ethyl or isopropyl.

Further embodiments of the invention are compounds of formula (I) or any of the subgroups of compounds of formula (I) wherein (a) R$^5$ is hydrogen; C$_{1-6}$alkyl; C$_{1-6}$alkoxyC$_{1-6}$alkyl; or C$_{3-7}$cycloalkyl
(b) R$^5$ is hydrogen or C$_{1-6}$alkyl;
(c) R$^5$ is hydrogen.

Preferred embodiments of the invention are compounds of formula (I) or any of the subgroups of compounds of formula (I) wherein R$^5$ is hydrogen, or C$_{1-6}$alkyl, more preferably hydrogen or methyl.

Still a further embodiment concerns compounds of formula (I), (I-e) or any subgroup of compounds of formula (I) wherein R$^{6a}$ and R$^{6b}$ independently are hydrogen or C$_{1-6}$alkyl, e.g. methyl. Preferably R$^{6a}$ is hydrogen and R$^{6b}$ is methyl, or more preferably R$^{6a}$ and R$^{6b}$ are both hydrogen.

Still a further embodiment concerns compounds of formula (I) or any subgroup of compounds of formula (I) wherein R$^7$ and R$^8$ each independently are selected from C$_{1-6}$alkyl optionally substituted with C$_{1-6}$alkoxy, hydroxy, halo, or with aryl; aryl; Het; C$_{2-6}$alkenyl; C$_{1-6}$alkoxy; aryloxy; Het-O—; hydroxy; cyano; halo; and —NR$^a$R$^b$; and R$^7$ may be hydrogen; or wherein R$^7$ and R$^8$ each independently are selected from C$_{1-6}$alkyl optionally substituted with C$_{1-6}$alkoxy or aryl; aryl; Het; C$_{2-6}$alkenyl; C$_{1-6}$alkoxy; aryloxy; Het-O—; hydroxy; cyano; halo; —NR$^a$R$^b$; and R$^7$ may be hydrogen; or wherein R$^7$ and R$^8$ each independently are selected from $C_{1-6}$alkyl optionally substituted with $C_{1-6}$alkoxy or aryl; aryl; pyridyl; $C_{1-6}$alkoxy; aryloxy; pyridyl-O—; or —NR$^a$R$^b$; wherein R$^a$ and R$^b$ each independently are hydrogen or $C_{1-6}$alkyl or the group —NR$^a$R$^b$ is Het$^1$; and R$^7$ may be hydrogen; or wherein R$^7$ and R$^8$ each independently are selected from $C_{1-6}$alkyl, $C_{1-6}$alkoxy; aryl; and —NR$^a$R$^b$; wherein R$^a$ and R$^b$ each independently are hydrogen or $C_{1-6}$alkyl or the group —NR$^a$R$^b$ is morpholinyl; and R$^7$ may be hydrogen. Particular subgroups of compounds of this embodiment are those wherein R$^9$ is hydrogen.

A particular embodiment of the invention concerns compounds of formula (I) or any subgroup thereof, wherein the ether linked pyrimidinyl moiety has the following structure:

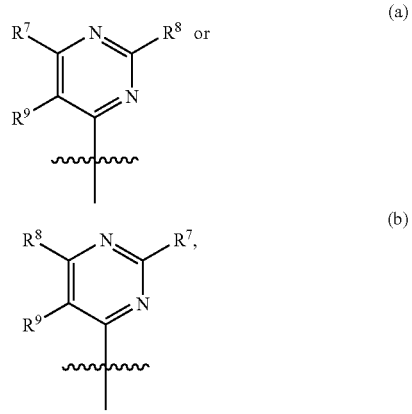

wherein R$^7$, R$^8$ and R$^9$ are as specified above.

Within this embodiment, the following further subgroups of compounds (I), or any subgroups thereof, are of interest: i.e. those wherein one or more of the following definitions apply:

R$^9$ is hydrogen or $C_{1-6}$alkyl, particularly hydrogen or methyl; or R$^9$ is hydrogen;

R$^7$ and R$^8$ independently are $C_{1-6}$alkyl, halo, $C_{1-6}$alkoxy, amino, mono- or di$C_{1-6}$alkyl-amino, aryl, Het, or Het$^1$; in particular wherein aryl, Het, or Het$^1$ is pyridyl, thiazolyl, oxazolyl, pyrazolyl, phenyl, piperidinyl, or morpholinyl; wherein said pyridyl, thiazolyl, oxazolyl, pyrazolyl, phenyl may be optionally substituted with one or two substituents selected from $C_{1-6}$alkyl, $C_{1-6}$alkoxy, halo, amino, and $C_{1-6}$alkoxy-$C_{1-6}$alkyl; or with one or two, or with one, substituent(s) selected from $C_{1-6}$alkyl, halo and $C_{1-6}$alkoxy, or selected from methoxy, chloro, or fluoro; and wherein said piperidinyl, or morpholinyl may be optionally substituted with one or two $C_{1-6}$alkyl; and wherein R$^7$ may also be hydrogen.

Particular subgroups within this embodiment are those wherein in the groups (a) or (b) one or more of the following definitions apply:

R$^7$ and R$^8$ independently are halo (e.g. chloro), $C_{1-6}$alkyl, $C_{1-6}$alkoxy (e.g. methoxy or isopropoxy), morpholinyl, piperidinyl, amino, mono- or di$C_{1-6}$alkylamino; or R$^7$ is hydrogen, $C_{1-6}$alkyl, $C_{1-6}$alkoxy (e.g. methoxy or isopropoxy), morpholinyl, mono- or di$C_{1-6}$alkylamino (e.g. methylamino or i.propylamino); and wherein R$^7$ may also be hydrogen;

R$^9$ is hydrogen or $C_{1-6}$alkyl, particularly hydrogen or methyl; or R$^9$ is hydrogen.

Particular subgroups within this embodiment are those wherein in the groups (a) or (b) one or more of the following definitions apply:

R$^7$ is hydrogen; $C_{1-6}$alkyl; $C_{1-6}$alkoxy; morpholinyl; piperidinyl; phenyl optionally substituted with halo, $C_{1-6}$alkyl, or with $C_{1-6}$alkoxy; amino; mono- or di$C_{1-6}$alkylamino; or R$^7$ is hydrogen; $C_{1-6}$alkoxy (e.g. methoxy or isopropoxy); morpholinyl; phenyl optionally substituted with $C_{1-6}$alkoxy; mono- or di$C_{1-6}$alkylamino (e.g. methylamino or i.propylamino);

R$^8$ is $C_{1-6}$alkyl, phenyl, morpholinyl, mono- or di$C_{1-6}$alkylamino; or R$^8$ is $C_{1-6}$alkyl (e.g. t.butyl), phenyl, morpholinyl, mono- or di$C_{1-6}$alkylamino (e.g. methylamino or i.propylamino).

A further embodiment concerns compounds of formula (I), or any subgroups thereof, wherein the substituents R$^7$ and R$^8$ in the groups (a) or (b) are independently selected from aryl, Het, —O-aryl, —O-Het, $C_{1-6}$alkyl optionally substituted with aryl or with Het. Aryl and Het in the previous definitions in particular may be optionally substituted phenyl, pyridyl, piperidinyl, morpholinyl, pyrazolyl and thiazolyl, each optionally substituted as specified above, in particular for R$^7$ and R$^8$ being phenyl, pyridyl, pyrazolyl, or thiazolyl, with methoxy, chloro or fluoro.

A further embodiment concerns compounds of formula (I), or any subgroups thereof, wherein the substituents R$^7$ and R$^8$ are independently $C_{1-6}$alkyl, e.g. tert.butyl, or $C_{1-6}$alkoxy, e.g. methoxy, or wherein R$^8$ is phenyl or pyridyl, optionally substituted Another embodiment concerns those compounds of formula (I) or any subgroups thereof, are those wherein the pyrimidinyl radical (a) or (b) is:

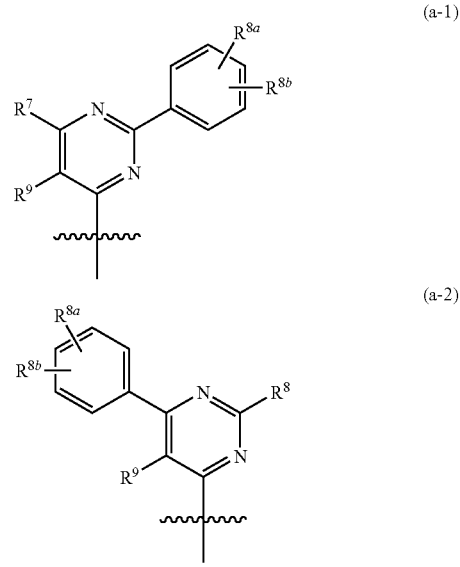

wherein R$^7$ and R$^8$ independently are phenyl or $C_{1-6}$alkoxy, e.g. methoxy;

R$^9$ is hydrogen or $C_{1-6}$alkyl; in particular R$^9$ is hydrogen or methyl; or R$^9$ is hydrogen;

R$^{8a}$ or R$^{8b}$ is an optional substituent of aryl, as specified above, in particular R$^{8a}$ or R$^{8b}$ is hydrogen, $C_{1-6}$alkoxy, e.g. methoxy, or halo, e.g. fluoro or chloro. When one of R$^{8a}$ or R$^{8b}$ is other than hydrogen, it may in particular be substituted in the para position of the phenyl ring.

The compounds of formula (I) consist of three building blocks P1, P2, P3. Building block P1 further contains a P1' tail. The carbonyl group marked with an asterisk in compound (I-c) below may be part of either building block P2 or of building block P3. For reasons of chemistry, building block P2 of the compounds of formula (I) wherein X is C incorporates the carbonyl group attached to the position 1'.

The linking of building blocks P1 with P2, P2 with P3, and P1 with P1' (when $R^1$ is —NH—$SO_2R^2$) involves forming an amide bond. The linking of blocks P1 and P3 involves double bond formation. The linking of building blocks P1, P2 and P3 to prepare compounds (I-i) or (I-j) can be done in any given sequence. One of the steps involves a cyclization whereby the macrocycle is formed.

In the following description, representation of compounds, and reaction schemes, $R^{10}$ represents the pyrimidinyl group:

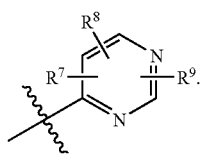

Represented herebelow are compounds (I-i) which are compounds of formula (I) wherein carbon atoms C7 and C8 are linked by a double bond, and compounds (I-j) which are compounds of formula (I) wherein carbon atoms C7 and C8 are linked by a single bond. The compounds of formula (I-j) can be prepared from the corresponding compounds of formula (I-I) by reducing the double bond in the macrocycle.

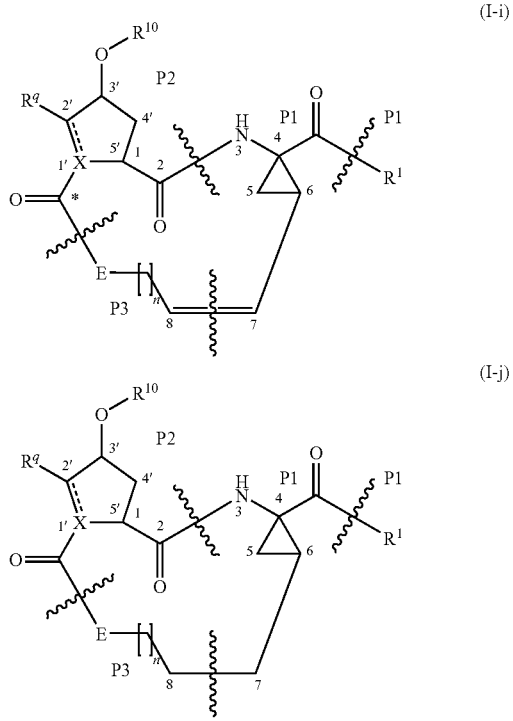

The synthesis procedures described hereinafter are meant to be applicable for as well the racemates, stereochemically pure intermediates or end products, or any stereoisomeric mixtures. The racemates or stereochemical mixtures may be separated into stereoisomeric forms at any stage of the synthesis procedures. In one embodiment, the intermediates and end products have the stereochemistry specified above in the compounds of formula (I-a) and (I-b).

In one embodiment, compounds (I-i) are prepared by first forming the amide bonds and subsequent forming the double bond linkage between P3 and P1 with concomitant cyclization to the macrocycle.

In one embodiment, compounds (I) wherein the bond between $C_7$ and $C_8$ is a double bond, which are compounds of formula (I-i), as defined above, may be prepared as outlined in the following reaction scheme:

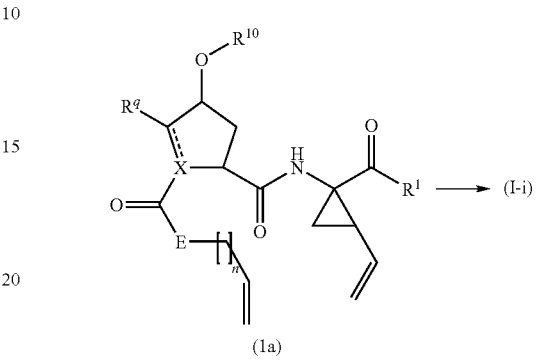

Formation of the macrocycle can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenylthio)methylene]ruthenium (IV) dichloride can be used. Other catalysts that can be used are Grubbs first and second generation catalysts, i.e. benzylidene-bis(tricyclohexylphosphine)dichlororuthenium and (1,3-bis-(2,4,6-trimethylphenyl)-2-imidazolidinylidene)dichloro(phenylmethylene)-(tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2, 4,6-trimethylphenyl)-2-imidazolidinylidene)dichloro-(o-isopropoxyphenylmethylene)ruthenium respectively. Also other catalysts containing other transition metals such as Mo can be used for this reaction.

The metathesis reactions may be conducted in a suitable solvent such as for example ethers, e.g. THF, dioxane; halogenated hydrocarbons, e.g. dichoromethane, $CHCl_3$, 1,2-dichloroethane and the like, hydrocarbons, e.g. toluene. In a preferred embodiment, the metathesis reaction is conducted in toluene. These reactions are conducted at increased temperatures under nitrogen atmosphere.

Compounds of formula (I) wherein the link between C7 and C8 in the macrocycle is a single bond, i.e. compounds of formula (I-j), can be prepared from the compounds of formula (I-i) by a reduction of the C7-C8 double bond in the compounds of formula (I-i). This reduction may be conducted by catalytic hydrogenation with hydrogen in the presence of a noble metal catalyst such as, for example, Pt, Pd, Rh, Ru or Raney nickel. Of interest is Rh on alumina. The hydrogenation reaction preferably is conducted in a solvent such as, e.g. an alcohol such as methanol, ethanol, or an ether such as THF, or mixtures thereof. Water can also be added to these solvents or solvent mixtures.

The A group can be connected to the P1 building block at any stage of the synthesis, i.e. before or after the cyclization, or before or after the cyclization and reduction as described herein above. The compounds of formula (I) wherein A represents —CO—NHSO$_2$R$^2$, said compounds being represented by formula (I-k-1), can be prepared by linking the A group to P1 by forming an amide bond between both moieties. Similarly, the compounds of formula (I) wherein R$^1$ represents —C(=O)OR$^1$, i.e. compounds (I-k-2), can be prepared by linking the R$^1$ group to P1 by forming an ester bond. In one embodiment, the —C(=O)OR$^1$ groups are introduced in the last step of the synthesis of the compounds (I) as outlined in the following reaction schemes wherein G represents a group:

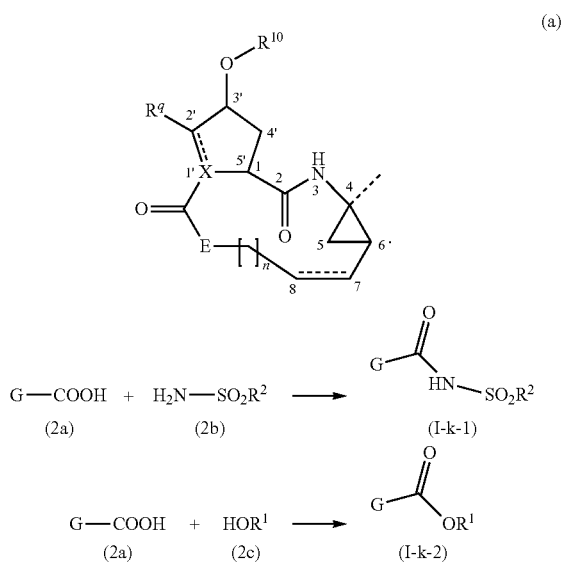

Intermediate (2a) can be coupled with sulfonamide (2b) by an amide forming reaction such as any of the procedures for the formation of an amide bond described hereinafter. In particular, (2a) may be treated with a coupling agent, for example N,N'-carbonyl-diimidazole (CDI), EEDQ, IIDQ, EDCI or benzotriazol-1-yl-oxy-tris-pyrrolidino-phosphonium hexafluorophosphate (commercially available as PyBOP®), in a solvent such as an ether, e.g. THF, or a halogenated hydrocarbon, e.g. dichloromethane, chloroform, dichloroethane, and reacted with the desired sulfonamide (2b), preferably after reacting (2a) with the coupling agent. The reactions of (2a) with (2b) preferably are conducted in the presence of a base, for example a trialkylamine such as triethylamine or diisopropylethylamine, or 1,8-diazabicyclo [5.4.0]undec-7-ene (DBU). Intermediate (2a) can also be converted into an activated form, e.g. an activated form of general formula G-CO—Z, wherein Z represents halo, or the rest of an active ester, e.g. Z is an aryloxy group such as phenoxy, p.nitrophenoxy, pentafluorophenoxy, trichlorophenoxy, pentachlorophenoxy and the like; or Z can be the rest of a mixed anhydride. In one embodiment, G-CO—Z is an acid chloride (G-CO—Cl) or a mixed acid anhydride (G-CO—O—CO—R or G-CO—O—CO—OR, R in the latter being e.g. C$_{1-4}$alkyl, such as methyl, ethyl, propyl, i.propyl, butyl, t.butyl, i.butyl, or benzyl). The activated form G-CO—Z is reacted with the sulfonamide (2b).

The compounds of formula (I) wherein A represents —C(=O)—NH—P(=O)(OR$^{6a}$)(R$^{6b}$), said compounds being represented by formula (I-k-3), can be prepared by forming an amide bond between intermediate (2a) and phosphoramidate (2d), following the procedures for the formation of an amide bond described hereinafter. In particular, (2a) may be treated with a coupling agent in an appropriate solvent, preferably in the presence of a base, followed by reaction with phosphoramidate (2d), preferably after reacting (2a) with the coupling agent. Intermediate (2a) can also be converted into an activated form, e.g. an activated form of general formula G-CO—Z, wherein Z represents halo, or the rest of an active ester, e.g. Z is an aryloxy group such as phenoxy, p-nitrophenoxy, pentafluorophenoxy, trichlorophenoxy, pentachlorophenoxy and the like; or Z can be the rest of a mixed anhydride. In one embodiment, G-CO—Z is an acid chloride (G-CO—Cl) or a mixed acid anhydride (G-CO—O—CO—R or G-CO—O—CO—OR, R in the latter being e.g. C$_{1-4}$alkyl, such as methyl, ethyl, propyl, i.propyl, butyl, t.butyl, i.butyl, or benzyl). The activated form G-CO—Z is reacted with the desired (2d). The coupling agent, solvent and base may be as described hereinafter in the general description of the preparation of amide bonds.

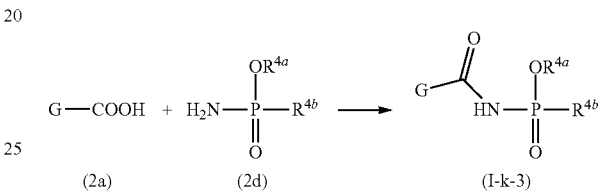

The activation of the carboxylic acid in (2a) as described in the above reactions may lead to an internal cyclization reaction to an azalactone intermediate of formula

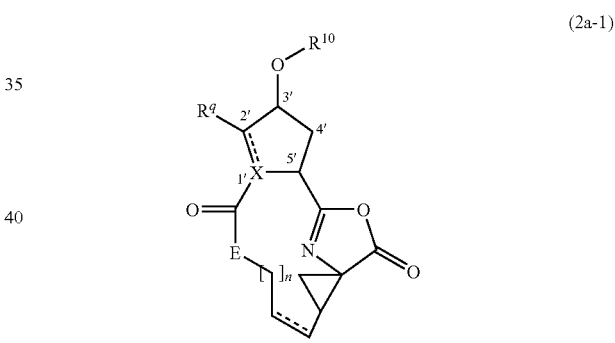

wherein X, E, R$^q$, R$^{10}$ and n are as specified above and wherein the stereogenic centers may have the stereochemical configuration as specified above, for example as in (1-a) or (1-b). The intermediates (2a-1) can be isolated from the reaction mixture, using conventional methodology, and the isolated intermediate (2a-1) is then reacted with (2b) or (2d), or the reaction mixture containing (2a-1) can be reacted further with (2b) or (2d) without isolation of (2a-1). In one embodiment, where the reaction with the coupling agent is conducted in a water-immiscible solvent, the reaction mixture containing (2a-1) may be washed with water or with slightly basic water in order to remove all water-soluble side products. The thus obtained washed solution may then be reacted with (2b) or (2d) without additional purification steps. The isolation of intermediates (2a-1) on the other hand may provide certain advantages in that the isolated product, after optional further purification, may be reacted with (2b) or (2d), giving rise to less side products and an easier work-up of the reaction.

Intermediate (2a) can be coupled with the alcohol (2c) by an ester forming reaction. For example, (2a) and (2c) are reacted together with removal of water either physically, e.g. by azeotropical water removal, or chemically by using a dehydrating agent. Intermediate (2a) can also be converted into an activated form G-CO—Z, such as the activated forms mentioned above, and subsequently reacted with the alcohol (2c). The ester forming reactions preferably are conducted in the presence of a base such as an alkali metal carbonate or hydrogen carbonate, e.g. sodium or potassium hydrogen carbonate, or a tertiary amine such as the amines mentioned herein in relation to the amide forming reactions, in particular a trialkylamine, e.g. triethylamine Solvents that can be used in the ester forming reactions comprise ethers such as THF; halogenated hydrocarbons such as dichoromethane, $CH_2Cl_2$; hydrocarbons such as toluene; polar aprotic solvents such as DMF, DMSO, DMA; and the like solvents.

The compounds of formula (I) wherein E is NH, said compounds being represented by (I-1), can also be prepared by removal of a protecting group PG, from a corresponding nitrogen-protected intermediate (3a), as in the following reaction scheme. The protecting group PG in particular is any of the nitrogen protecting groups mentioned hereinafter and can be removed using procedures also mentioned hereinafter:

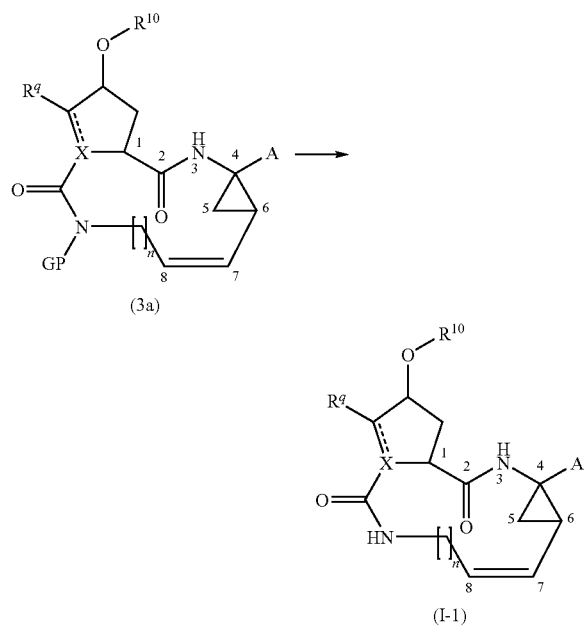

The starting materials (3a) in the above reaction can be prepared following the procedures for the preparation of compounds of formula (I), but using intermediates wherein the group $R^5$ is PG.

The compounds of formula (I) can also be prepared by reacting an intermediate (4a) with intermediate (4b) as outlined in the following reaction scheme wherein the various radicals have the meanings specified above:

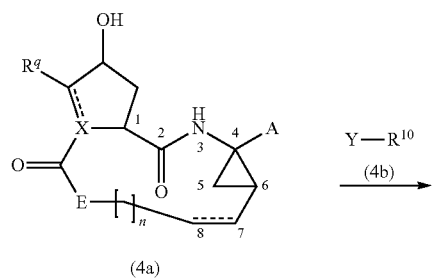

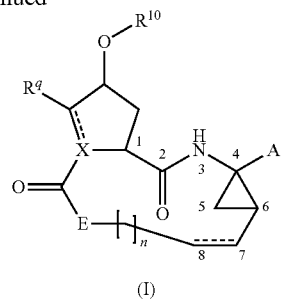

Y in (4b) represents hydroxy or a leaving group LG such as a halide, e.g. bromide or chloride, or an arylsulfonyl group, e.g. mesylate, triflate or tosylate and the like.

In one embodiment, the reaction of (4a) with (4b) is an O-arylation reaction and Y represents a leaving group. This reaction can be conducted following the procedures described by E. M. Smith et al. (J. Med. Chem. (1988), 31, 875-885). In particular, this reaction is conducted in the presence of a base, preferably a strong base, in a reaction-inert solvent, e.g. one of the solvents mentioned for the formation of an amide bond.

In a particular embodiment, starting material (4a) is reacted with (4b) in the presence of a base which is strong enough to detract a hydrogen from the hydroxy group, for example an alkali of alkaline metal hydride such as LiH or sodium hydride, or alkali metal alkoxide such as sodium or potassium methoxide or ethoxide, potassium tert-butoxide, in a reaction inert solvent like a dipolar aprotic solvent, e.g. DMA, DMF and the like. The resulting alcoholate is reacted with the arylating agent (4b), wherein Y is a suitable leaving group as mentioned above. The conversion of (4a) to (I) using this type of O-arylation reaction does not change the stereochemical configuration at the carbon bearing the hydroxy group.

Alternatively, the reaction of (4a) with (4b) can also be conducted via a Mitsunobu reaction (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706). This reaction comprises treatment of intermediate (4a) with (4b) wherein Y is hydroxy, in the presence of triphenylphosphine and an activating agent such as a dialkyl azocarboxylate, e.g. diethyl azodicarboxylate (DEAD), diisopropyl azodicarboxylate (DIAD) or the like. The Mitsunobu reaction changes the stereochemical configuration at the carbon bearing the hydroxy group.

Alternatively, in order to prepare the compounds of formula (I), first an amide bond between building blocks P2 and P1 is formed, followed by coupling of the P3 building block to the P1 moiety in P1-P2, and a subsequent carbamate or ester bond formation between P3 and the P2 moiety in P2-P1-P3 with concomitant ring closure.

Yet another alternative synthetic methodology is the formation of an amide bond between building blocks P2 and P3, followed by the coupling of building block P1 to the P3 moiety in P3-P2, and a last amide bond formation between P1 and P2 in P1-P3-P2 with concomitant ring closure.

Building blocks P1 and P3 can be linked to a P1-P3 sequence. If desired, the double bond linking P1 and P3 may be reduced. The thus formed P1-P3 sequence, either reduced or not, can be coupled to building block P2 and the thus forming sequence P1-P3-P2 subsequently cyclized, by forming an amide bond.

Building blocks P1 and P3 in any of the previous approaches can be linked via double bond formation, e.g. by the olefin metathesis reaction described hereinafter, or a Wittig type reaction. If desired, the thus formed double bond can be reduced, similarly as described above for the conversion of (I-i) to (I-j). The double bond can also be reduced at a later stage, i.e. after addition of a third building block, or after formation of the macrocycle. Building blocks P2 and P1 are linked by amide bond formation and P3 and P2 are linked by carbamate or ester formation.

The tail P1' can be bonded to the P1 building block at any stage of the synthesis of the compounds of formula (I), for example before or after coupling the building blocks P2 and P1; before or after coupling the P3 building block to P1; or before or after ring closure.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[(3-dimethylamino)propyl]carbodiimide) method, the active ester method (e.g. p-nitrophenyl, p-chlorophenyl, trichlorophenyl, pentachloro-phenyl, pentafluorophenyl, N-hydroxysuccinic imido and the like esters), the Woodward reagent K-method, the 1,1-carbonyldiimidazole (CDI or N,N'-carbonyl-diimidazole) method, the phosphorus reagents or oxidation-reduction methods. Some of these methods can be enhanced by adding suitable catalysts, e.g. in the carbodiimide method by adding 1-hydroxybenzotriazole, DBU (1,8-diazabicyclo-[5.4.0]undec-7-ene), or 4-DMAP. Further coupling agents are (benzotriazol-1-yloxy)tris-(dimethylamino) phosphonium hexafluorophosphate, either by itself or in the presence of 1-hydroxybenzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed in either solution (liquid phase) or solid phase.

A preferred amide bond formation is performed employing N-ethyloxycarbonyl-2-ethyloxy-1,2-dihydroquinoline (EEDQ) or N-isobutyloxy-carbonyl-2-isobutyloxy-1,2-dihydroquinoline (IIDQ). Unlike the classical anhydride procedure, EEDQ and IIDQ do not require base nor low reaction temperatures. Typically, the procedure involves reacting equimolar amounts of the carboxyl and amine components in an organic solvent (a wide variety of solvents can be used). Then EEDQ or IIDQ is added in excess and the mixture is allowed to stir at room temperature.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicycle[5.4.0]undec-7-ene (DBU). The reaction temperature may range between 0° C. and 50° C. and the reaction time may range between 15 min and 24 h.

The functional groups in the building blocks that are linked together may be protected to avoid formation of undesired bonds. Appropriate protecting groups that can be used are listed for example in Greene, "Protective Groups in Organic Chemistry", John Wiley & Sons, New York (1999) and "The Peptides: Analysis, Synthesis, Biology", Vol. 3, Academic Press, New York (1987).

Carboxyl groups can be protected as an ester that can be cleaved off to give the carboxylic acid. Protecting groups that can be used include 1) alkyl esters such as methyl, trimethylsilyl and tert-butyl; 2) arylalkyl esters such as benzyl and substituted benzyl; or 3) esters that can be cleaved by a mild base or mild reductive means such as trichloroethyl and phenacyl esters.

Amino groups can be protected by a variety of N-protecting groups, such as:
1) acyl groups such as formyl, trifluoroacetyl, phthalyl, and p-toluenesulfonyl;
2) aromatic carbamate groups such as benzyloxycarbonyl (Cbz or Z) and substituted benzyloxycarbonyls, and 9-fluorenylmethyloxycarbonyl (Fmoc);
3) aliphatic carbamate groups such as tert-butyloxycarbonyl (Boc), ethoxycarbonyl, diisopropylmethoxy-carbonyl, and allyloxycarbonyl;
4) cyclic alkyl carbamate groups such as cyclopentyloxycarbonyl and adamantyloxycarbonyl;
5) alkyl groups such as triphenylmethyl, benzyl or substituted benzyl such as 4-methoxybenzyl;
6) trialkylsilyl such as trimethylsilyl or t.Bu dimethylsilyl; and
7) thiol containing groups such as phenylthiocarbonyl and dithiasuccinoyl. Interesting amino protecting groups are Boc and Fmoc.

Preferably the amino protecting group is cleaved off prior to the next coupling step. Removal of N-protecting groups can be done following art-known procedures. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature, usually around 15-25° C., or 20-22° C.

Other functional groups that can interfere in the coupling reactions of the building blocks may also be protected. For example hydroxyl groups may be protected as benzyl or substituted benzyl ethers, e.g. 4-methoxybenzyl ether, benzoyl or substituted benzoyl esters, e.g. 4-nitrobenzoyl ester, or with trialkylsilyl groups (e.g. trimethylsilyl or tert-butyldimethylsilyl).

Further amino groups may be protected by protecting groups that can be cleaved off selectively. For example, when Boc is used as the α-amino protecting group, the following side chain protecting groups are suitable: p-toluenesulfonyl (tosyl) moieties can be used to protect further amino groups; benzyl (Bn) ethers can be used to protect hydroxy groups; and benzyl esters can be used to protect further carboxyl groups. Or when Fmoc is chosen for the α-amino protection, usually tert-butyl based protecting groups are acceptable. For instance, Boc can be used for further amino groups; tert-butyl ethers for hydroxyl groups; and tert-butyl esters for further carboxyl groups.

Any of the protecting groups may be removed at any stage of the synthesis procedure but preferably, the protecting groups of any of the functionalities not involved in the reaction steps are removed after completion of the build-up of the macrocycle. Removal of the protecting groups can be done in whatever manner is dictated by the choice of protecting groups, which manners are well known to those skilled in the art.

The intermediates of formula (1a) wherein X is N, said intermediates being represented by formula (1a-1), may be prepared starting from intermediates (5a) which are reacted with an alkenamine (5b) in the presence of a carbonyl introducing agent as outlined in the following reaction scheme.

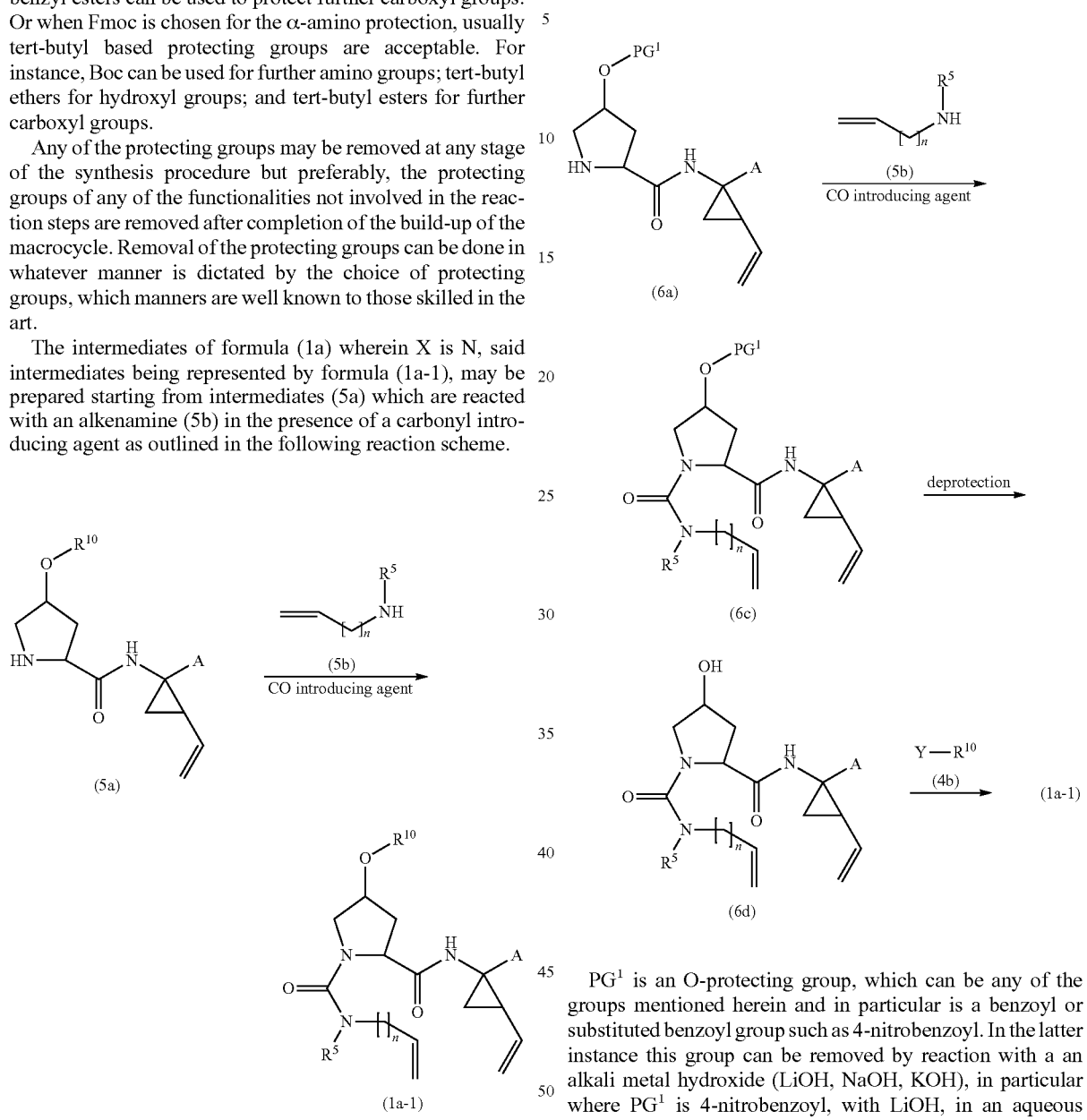

Carbonyl (CO) introducing agents include phosgene, or phosgene derivatives such as carbonyl diimidazole (CDI), and the like. In one embodiment (5a) is reacted with the CO introducing agent in the presence of a suitable base and a solvent, which can be the bases and solvents used in the amide forming reactions as described above. In a particular embodiment, the base is a hydrogencarbonate, e.g. NaHCO$_3$, or a tertiary amine such as triethylamine and the like, and the solvent is an ether or halogenated hydrocarbon, e.g. THF, CH$_2$Cl$_2$, CHCl$_3$, and the like. Thereafter, the amine (5b) is added thereby obtaining intermediates (1a-1) as in the above scheme. An alternative route using similar reaction conditions involves first reacting the CO introducing agent with the alkenamine (5b) and then reacting the thus formed intermediate with (5a).

The intermediates (1a-1) can alternatively be prepared as follows:

PG$^1$ is an O-protecting group, which can be any of the groups mentioned herein and in particular is a benzoyl or substituted benzoyl group such as 4-nitrobenzoyl. In the latter instance this group can be removed by reaction with a an alkali metal hydroxide (LiOH, NaOH, KOH), in particular where PG$^1$ is 4-nitrobenzoyl, with LiOH, in an aqueous medium comprising water and a water-soluble organic solvent such as an alkanol (methanol, ethanol) and THF.

Intermediates (6a) are reacted with (5b) in the presence of a carbonyl introducing agent, similar as described above, and this reaction yields intermediates (6c). These are deprotected, in particular using the reaction conditions mentioned above. The resulting alcohol (6d) is reacted with intermediates (4b) as described above for the reaction of (4a) with (4b) and this reaction results in intermediates (1a-1).

The intermediates of formula (1a) wherein X is C, said intermediates being represented by formula (1a-2), may be prepared by an amide forming reaction starting from intermediates (7a) which are reacted with an amine (5b) as shown in the following reaction scheme, using reaction conditions for preparing amides such as those described above.

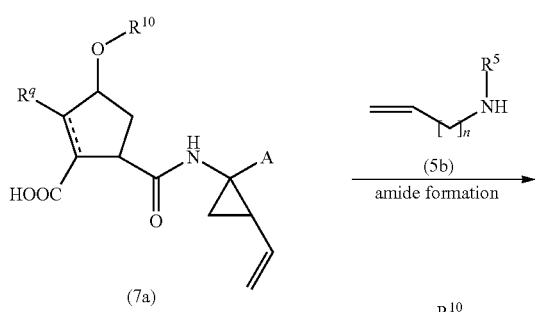

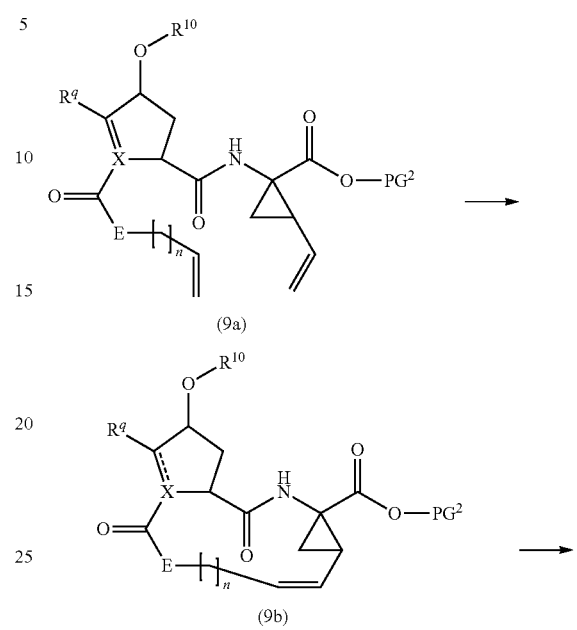

The intermediates of formula (2a) may be prepared by first cyclizing the open amide (9a) to a macrocyclic ester (9b), which in turn is converted to (2a) as follows:

The intermediates (1a-2) can alternatively be prepared as follows:

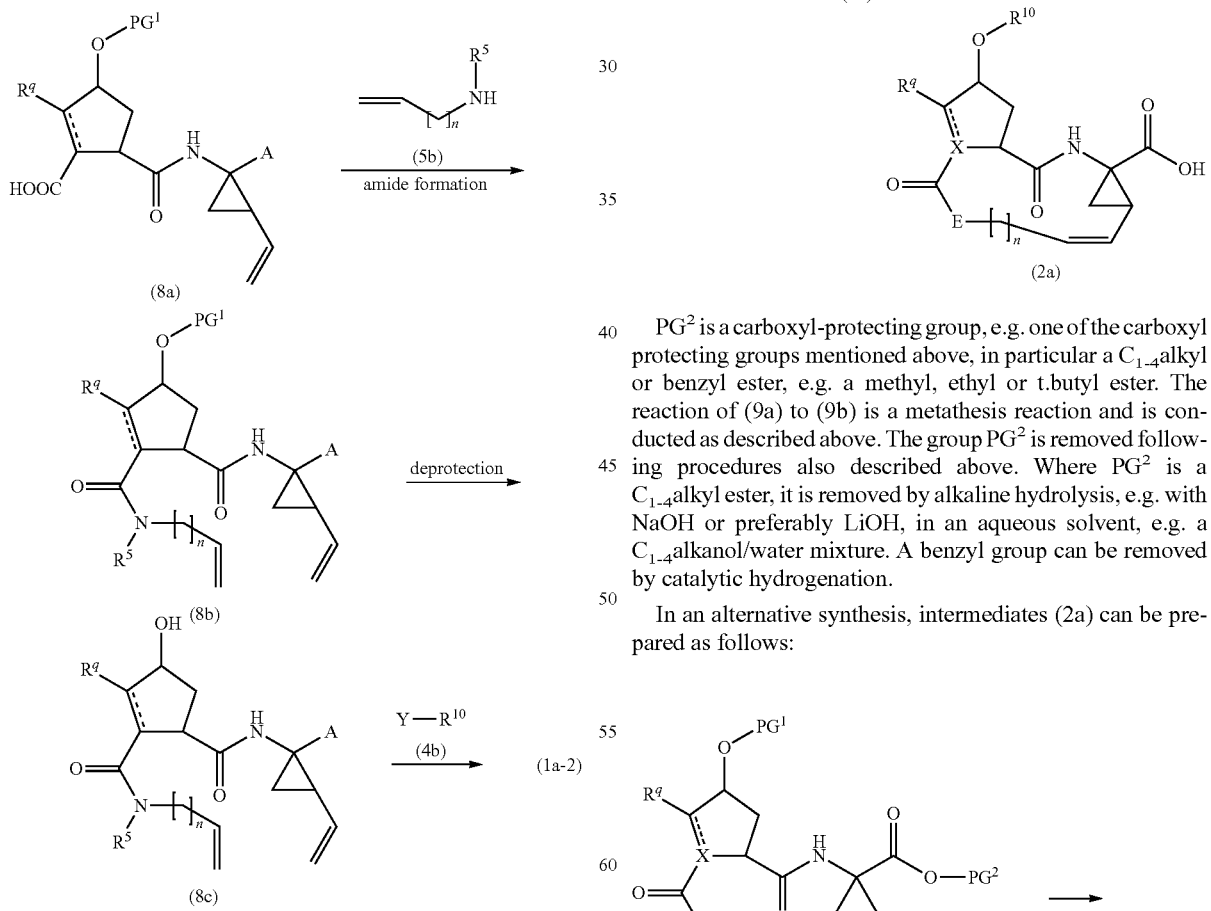

PG² is a carboxyl-protecting group, e.g. one of the carboxyl protecting groups mentioned above, in particular a $C_{1-4}$alkyl or benzyl ester, e.g. a methyl, ethyl or t.butyl ester. The reaction of (9a) to (9b) is a metathesis reaction and is conducted as described above. The group PG² is removed following procedures also described above. Where PG² is a $C_{1-4}$alkyl ester, it is removed by alkaline hydrolysis, e.g. with NaOH or preferably LiOH, in an aqueous solvent, e.g. a $C_{1-4}$alkanol/water mixture. A benzyl group can be removed by catalytic hydrogenation.

In an alternative synthesis, intermediates (2a) can be prepared as follows:

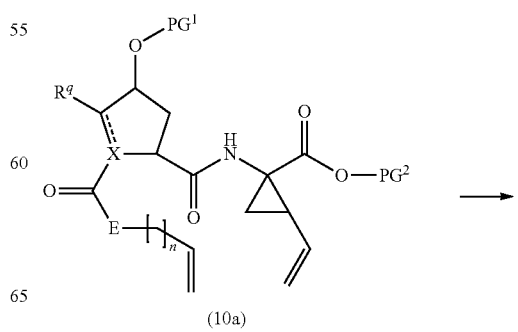

PG¹ is an O-protecting group as described above. The same reaction conditions as described above may be used: amide formation as described above, removal of PG¹ as in the description of the protecting groups and introduction of $R^{10}$ as in the reactions of (4a) with the reagents (4b).

-continued

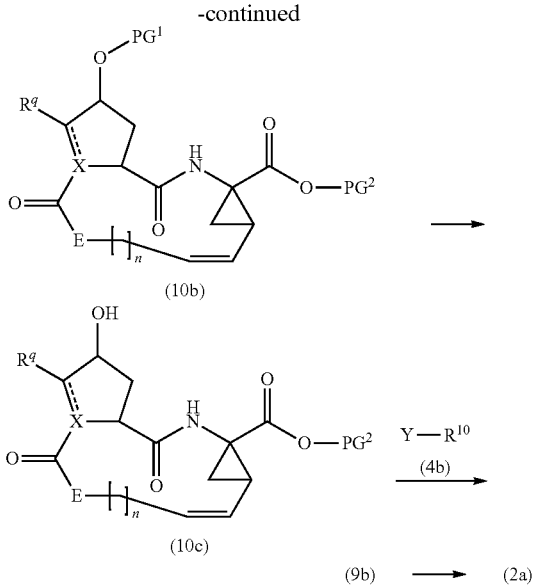

The PG¹ group is selected such that it is selectively cleavable towards PG². PG² may be e.g. methyl or ethyl esters, which can be removed by treatment with an alkali metal hydroxide in an aqueous medium, in which case PG¹ e.g. is t.butyl or benzyl. PG² may be t.butyl esters removable under weakly acidic conditions or PG¹ may be benzyl ethers removable with strong acid or by catalytic hydrogenation, in the latter two cases PG¹ e.g. is a benzoic ester such as a 4-nitrobenzoic ester.

First, intermediates (10a) are cyclized to the macrocyclic esters (10b), the latter are deprotected by removal of the PG¹ group to (10c), which are reacted with intermediates (4b), followed by removal of carboxyl protecting group PG². The cyclization, deprotection of PG¹ and PG² and the coupling with (4b) are as described above.

The A groups can be introduced at any stage of the synthesis, either as the last step as described above, or earlier, before the macrocycle formation. In the following scheme, the groups A being —CO—NH—SO₂R² or —CO—OR⁵ (which are as specified above) are introduced:

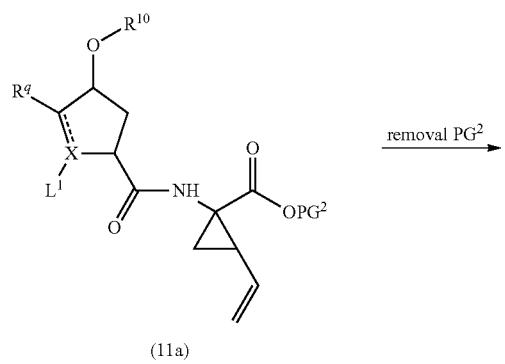

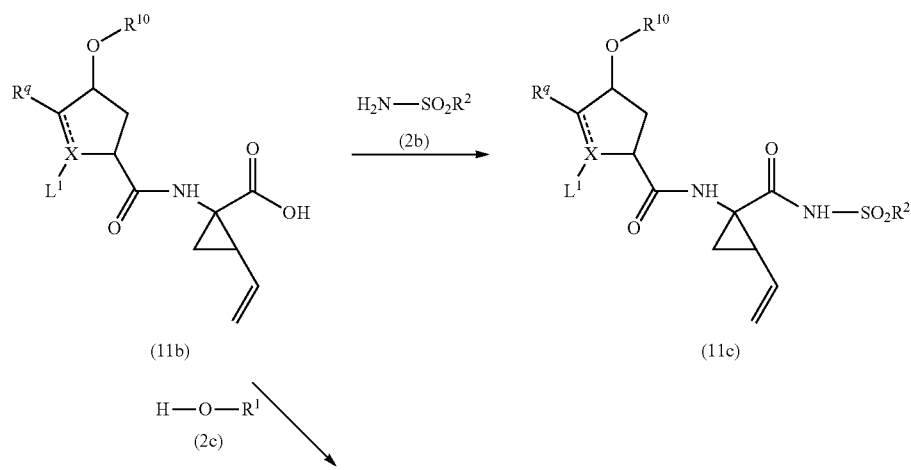

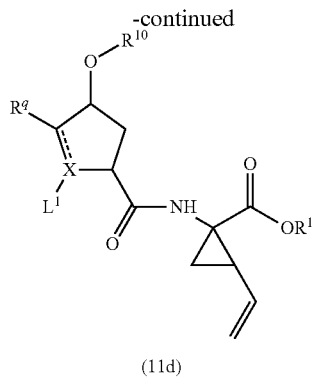

(11d)

In the above scheme, PG² is as defined above and L¹ is a P3 group

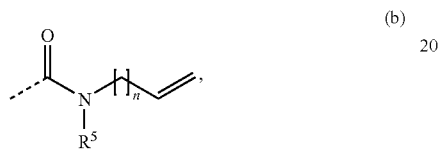

wherein n and $R^5$ are as defined above and where X is N, $L^1$ may also be a nitrogen-protecting group (PG, as defined above) and where X is C, $L^1$ may also be a group —COOPG$^{2a}$, wherein the group PG$^{2a}$ is a carboxyl protecting group similar as PG², but wherein PG$^{2a}$ is selectively cleavable towards PG². In one embodiment PG$^{2a}$ is t.butyl and PG² is methyl or ethyl.

The intermediates (11c) and (11d) wherein $L^1$ represents a group (b) correspond to the intermediates (1a) and may be processed further as specified above.

Coupling of P1 and P2 Building Blocks

The P1 and P2 building blocks are linked using an amide forming reaction following the procedures described above. The P1 building block may have a carboxyl protecting group PG² (as in (12b)) or may already be linked to P1' group (as in (12c)). $L^2$ is a N-protecting group (PG), or a group (b), as specified above. $L^3$ is hydroxy, —OPG¹ or a group —O—R¹⁰ as specified above. Where in any of the following reaction schemes $L^3$ is hydroxy, prior to each reaction step, it may be protected as a group —OPG¹ and, if desired, subsequently deprotected back to a free hydroxy function. Similarly as described above, the hydroxy function may be converted to a group —O—R¹⁰.

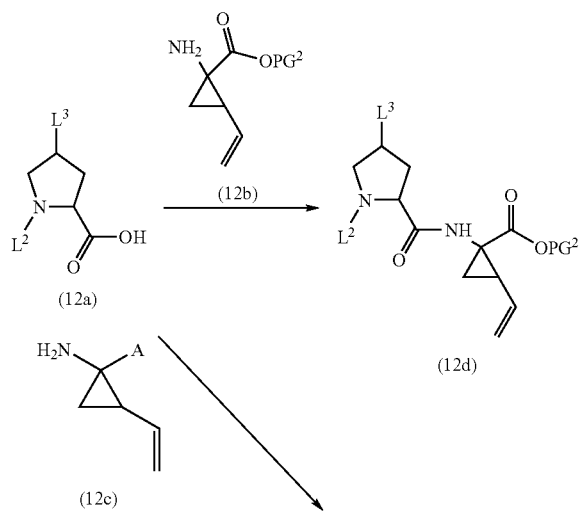

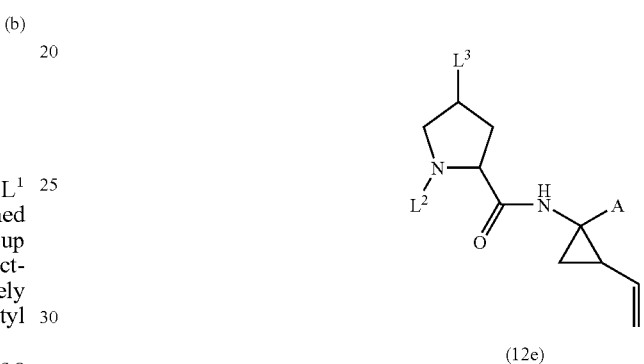

(12e)

In the procedure of the above scheme, a cyclopropyl amino acid (12b) or (12c) is coupled to the acid function of the P2 building block (12a) with the formation of an amide linkage, following the procedures described above. Intermediates (12d) or (12e) are obtained. Where in the latter $L^2$ is a group (b), the resulting products are P3-P2-P1 sequences encompassing some of the intermediates (11c) or (11d) in the previous reaction scheme. Removal of the acid protecting group in (12d), using the appropriate conditions for the protecting group used, followed by coupling with an amine H₂N—SO₂R² (2b), with HOR¹ (2c), or a phosphoramidate (4d), as described above, again yields the intermediates (12e), wherein -A are amide or ester groups. Where $L^2$ is a N-protecting group, it can be removed yielding intermediates (5a) or (6a). In one embodiment, PG in this reaction is a BOC group and PG² is methyl or ethyl. Where additionally $L^3$ is hydroxy, the starting material (12a) is Boc-L-hydroxyproline. In a particular embodiment, PG is BOC, PG² is methyl or ethyl and $L^3$ is —O—R¹⁰.

In one embodiment, $L^2$ is a group (b) and these reactions involve coupling P1 to P2-P3, which results in the intermediates (1a-1) or (1a) mentioned above. In another embodiment, $L^2$ is a N-protecting group PG, which is as specified above, and the coupling reaction results in intermediates (12d-1) or (12e-1), from which the group PG can be removed, using reaction conditions mentioned above, obtaining intermediates (12-f) or respectively (12g), which encompass intermediates (5a) and (6a) as specified above:

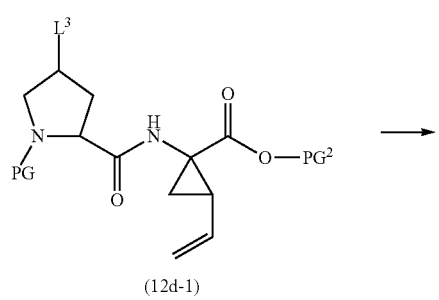

(12d-1)

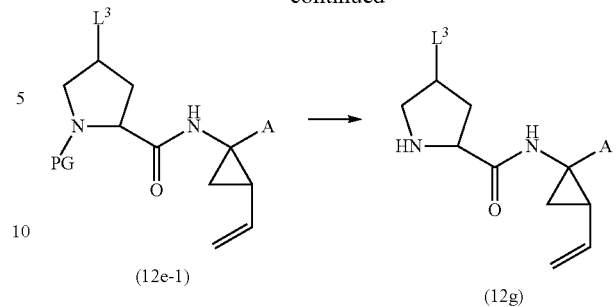

(12e-1) (12g)

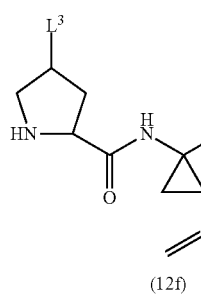

(12f)

In one embodiment, the group $L^3$ in the above schemes represents a group —O-$PG^1$ which can be introduced on a starting material (12a) wherein $L^3$ is hydroxy. In this instance $PG^1$ is chosen such that it is selectively cleavable towards group $L^2$ being PG.

In a similar way, P2 building blocks wherein X is C, which are cyclopentane or cyclopentene derivatives, can be linked to P1 building blocks as outlined in the following scheme wherein A, $R^q$, $L^3$ are as specified above and $PG^2$ and $PG^{2a}$ are carboxyl protecting groups. $PG^{2a}$ typically is chosen such that it is selectively cleavable towards group $PG^2$. Removal of the $PG^{2a}$ group in (13c) yields intermediates (7a) or (8a), which can be reacted with (5b) as described above.

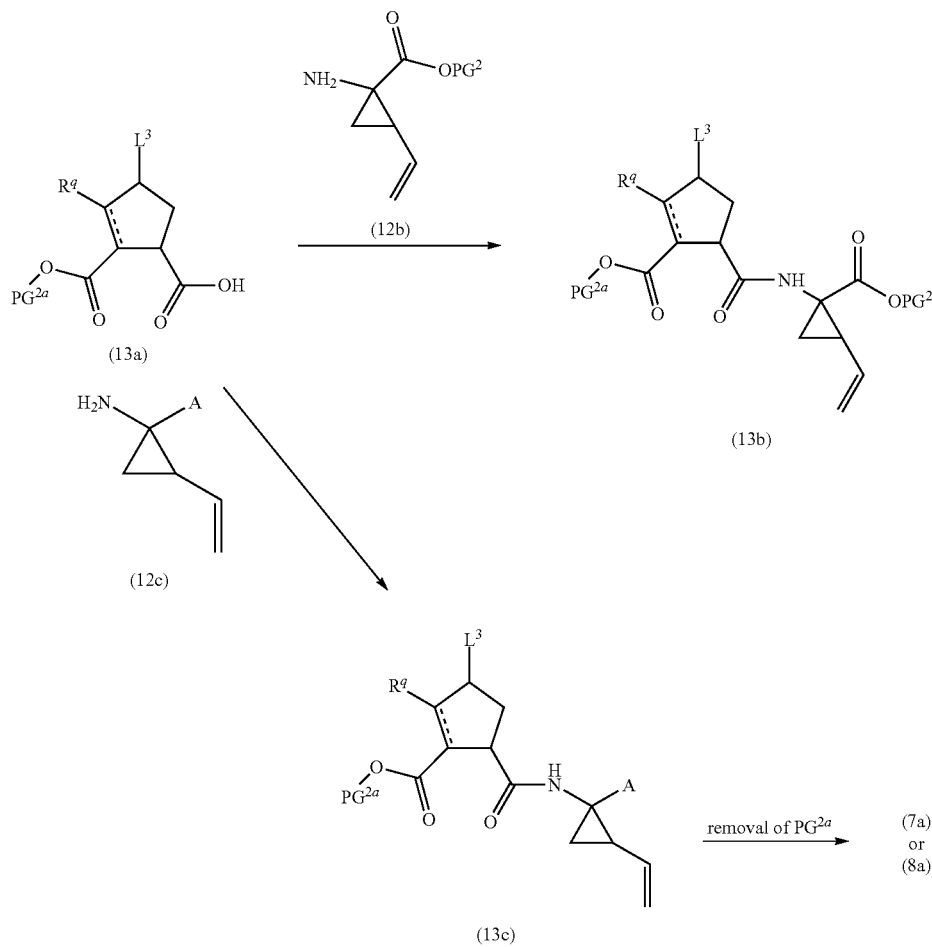

In a particular embodiment, where X is C, $R^q$ is H, and where X and the carbon bearing $R^q$ are linked by a single bond (P2 being a cyclopentane moiety), $PG^{2a}$ and $L^3$ taken together form a bond and the P2 building block is represented by formula:

(c)

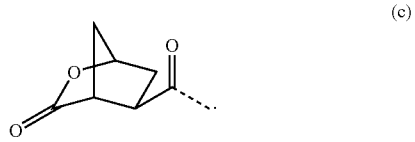

Bicyclic acid (14a) is reacted with (12b) or (12c) similar as described above to (14b) and (14c) respectively, wherein the lactone is opened giving intermediates (14c) and (14e). The lactones can be opened using ester hydrolysis procedures, for example using the reaction conditions described above for the alkaline removal of a $PG^1$ group in (9b), in particular using basic conditions such as an alkali metal hydroxide, e.g. NaOH, KOH, in particular LiOH.

Intermediates (14c) and (14e) can be processed further as described hereinafter.

Coupling of P3 and P2 Building Blocks

For P2 building blocks that have a pyrrolidine moiety, the P3 and P2 or P3 and P2-P1 building blocks are linked using a carbamate forming reaction following the procedures described above for the coupling of (5a) with (5b). A general procedure for coupling P2 blocks having a pyrrolidine moiety is represented in the following reaction scheme wherein $L^3$ is as specified above and $L^4$ is a group —O-$PG^2$, a group (d)

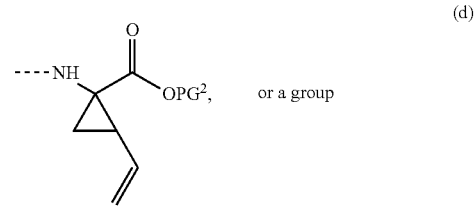

or a group

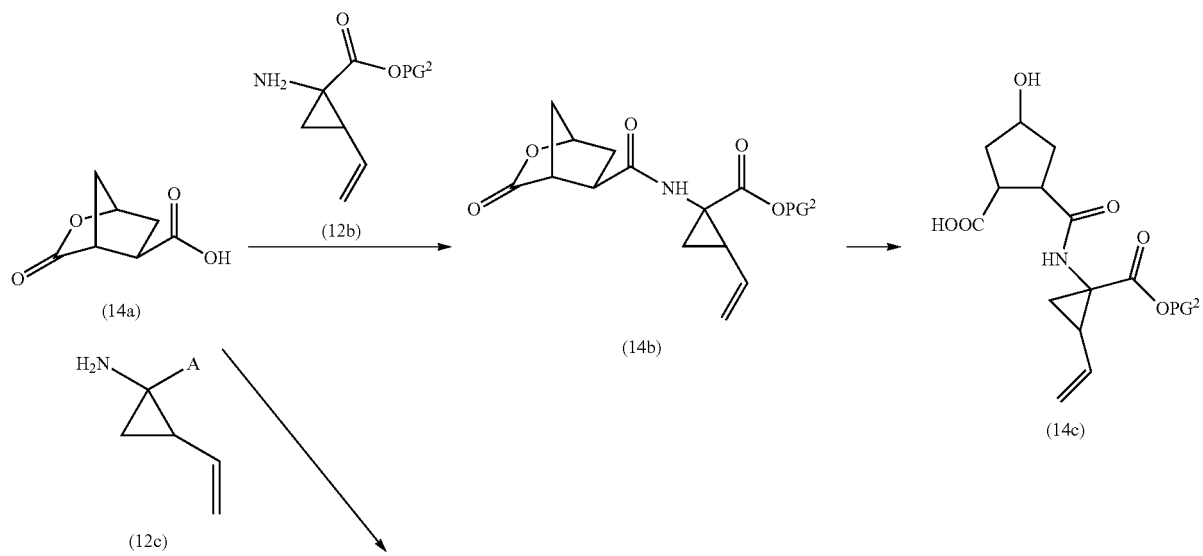

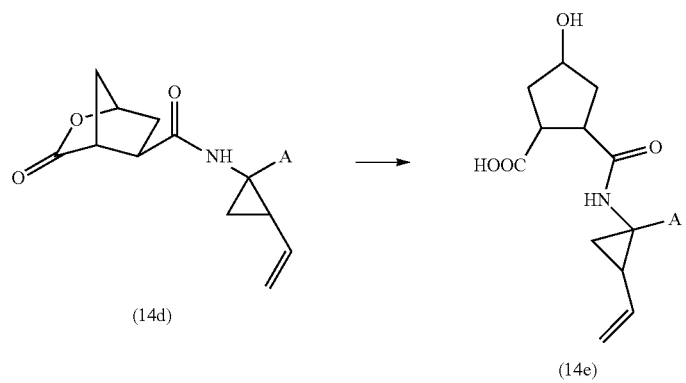

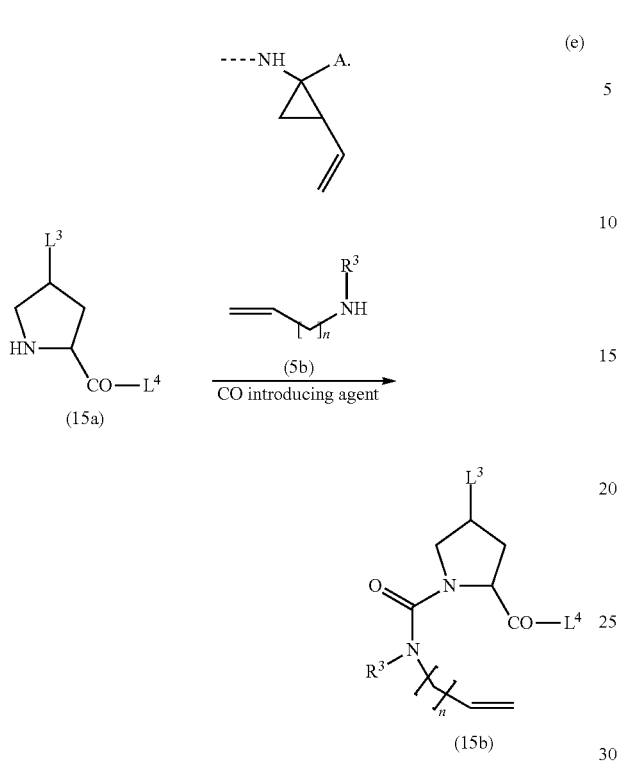

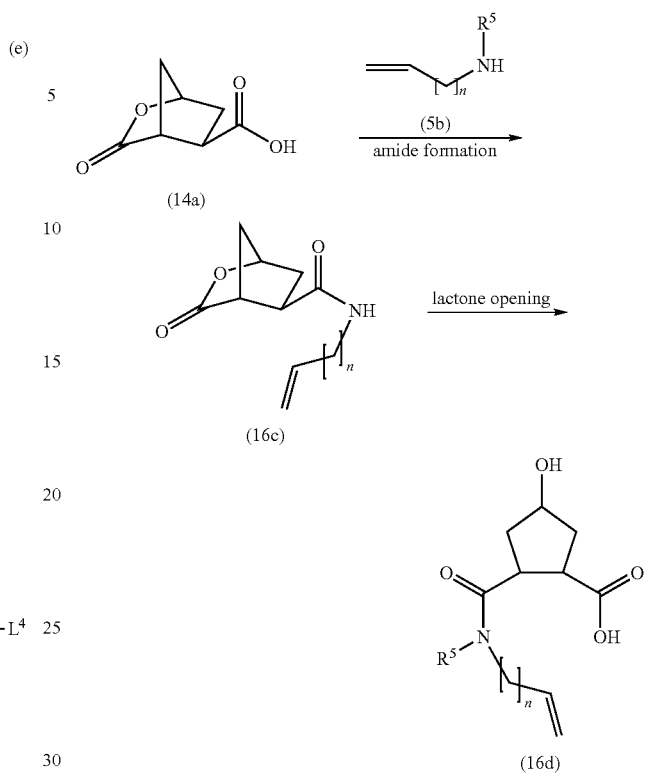

In one embodiment L⁴ in (15a) is a group —OPG², the PG² group may be removed and the resulting acid coupled with cyclopropyl amino acids (12a) or (12b), yielding intermediates (12d) or (12e) wherein L² is a radical (d) or (e).

A general procedure for coupling P3 blocks with a P2 block or a with a P2-P1 block wherein the P2 is a cyclopentane or cyclopentene is shown in the following scheme. L³ and L⁴ are as specified above.

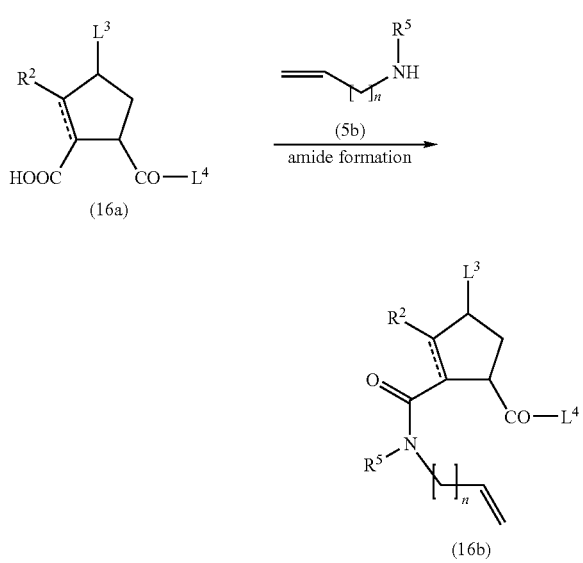

In a particular embodiment L³ and L⁴ taken together may form a lactone bridge as in (14a), and the coupling of a P3 block with a P2 block is as follows:

Bicyclic lactone (14a) is reacted with (5b) in an amide forming reaction to amide (16c) in which the lactone bridge is opened to (16d). The reaction conditions for the amide forming and lactone opening reactions are as described above or hereinafter. Intermediate (16d) in turn can be coupled to a P1 group as described above.

The reactions in the above schemes are conducted using the same procedures as described above for the reactions of (5a), (7a) or (8a) with (5b) and in particular the above reactions wherein L⁴ is a group (d) or (e) correspond to the reactions of (5a), (7a) or (8a) with (5b), as described above.

The building blocks P1, P1', P2 and P3 used in the preparation of the compounds of formula (I) can be prepared starting from art-known intermediates. A number of such syntheses are described hereafter in more detail.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

Synthesis of P2 Building Blocks

The P2 building blocks contain either a pyrrolidine, a cyclopentane, or a cyclopentene moiety substituted with a group —O—R¹⁰.

P2 building blocks containing a pyrrolidine moiety can be derived from commercially available hydroxy proline.

The preparation of P2 building blocks that contain a cylopentane ring may be performed as shown in the scheme below.

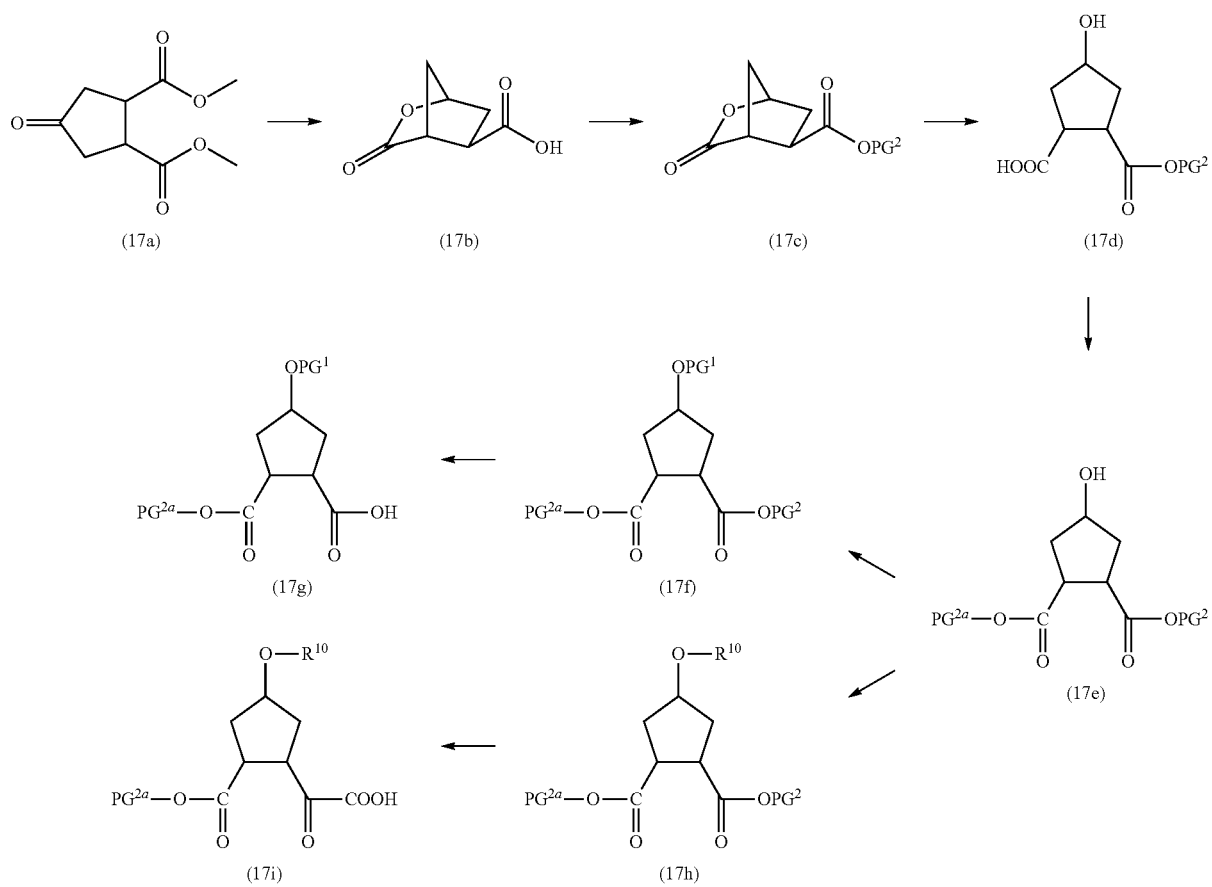

The bicyclic acid (17b) can be prepared, for example, from 3,4-bis(methoxycarbonyl)-cyclopentanone (17a), as described by Rosenquist et al. in Acta Chem. Scand. 46 (1992) 1127-1129. A first step in this procedure involves the reduction of the keto group with a reducing agent like sodium borohydride in a solvent such as methanol, followed by hydrolysis of the esters and finally ring closure to the bicyclic lactone (17b) using lactone forming procedures, in particular by using acetic anhydride in the presence of a weak base such as pyridine. The carboxylic acid functionality in (17b) can then be protected by introducing an appropriate carboxyl protecting group, such as a group $PG^2$, which is as specified above, thus providing bicyclic ester (17c). The group $PG^2$ in particular is acid-labile such as a t.butyl group and is introduced e.g. by treatment with isobutene in the presence of a Lewis acid or with di-tert-butyl dicarbonate in the presence of a base such as a tertiary amine like dimethylaminopyridine or triethylamine in a solvent like dichloromethane. Lactone opening of (17c) using reaction conditions described above, in particular with lithium hydroxide, yields the acid (17d), which can be used further in coupling reactions with P1 building blocks. The free acid in (17d) may also be protected, preferably with an acid protecting group $PG^{2a}$ that is selectively cleavable towards $PG^2$, and the hydroxy function may be converted to a group —$OPG^1$ or to a group —O—$R^{10}$. The products obtained upon removal of the group $PG^2$ are intermediates (17g) and (17i) which correspond to intermediates (13a) or (16a) specified above.

Intermediates with specific stereochemistry may be prepared by resolving the intermediates in the above reaction sequence. For example, (17b) may be resolved following art-known procedures, e.g. by salt form action with an optically active base or by chiral chromatography, and the resulting stereoisomers may be processed further as described above. The OH and COOH groups in (17d) are in cis position. Trans analogs can be prepared by inverting the stereochemistry at the carbon bearing the OH function by using specific reagents in the reactions introducing $OPG^1$ or O—$R^{10}$ that invert the stereochemistry, such as, e.g. by applying a Mitsunobu reaction.

In one embodiment, the intermediates (17d) are coupled to P1 blocks (12b) or (12c), which coupling reactions correspond to the coupling of (13a) or (16a) with the same P1 blocks, using the same conditions. Subsequent introduction of a —O—$R^{10}$-substituent as described above followed by removal of the acid protection group $PG^2$ yields intermediates (8a-1), which are a subclass of the intermediates (7a), or part of the intermediates (16a). The reaction products of the $PG^2$ removal can be further coupled to a P3 building block. In one embodiment $PG^2$ in (17d) is t.butyl which can be removed under acidic conditions, e.g. with trifluoroacetic acid.

(17d) 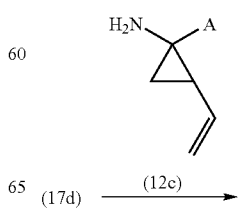 (12c) →

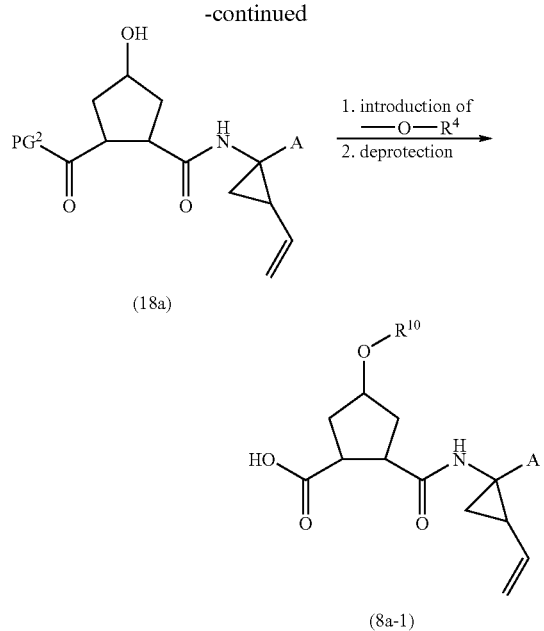

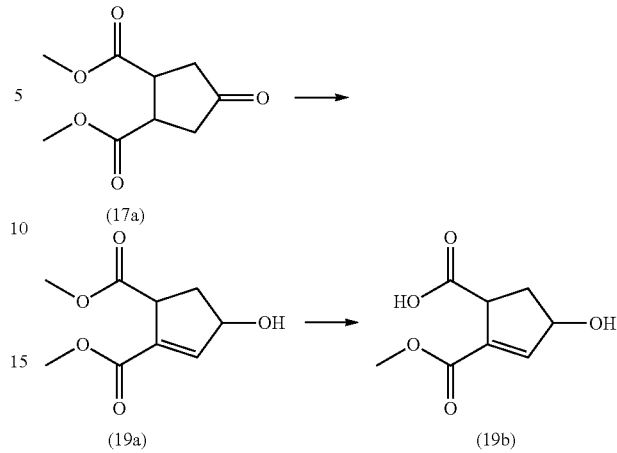

A bromination-elimination reaction of 3,4-bis(methoxycarbonyl)cyclopentanone (17a) as described by Dolby et al. in J. Org. Chem. 36 (1971) 1277-1285 followed by reduction of the keto functionality with a reducing agent like sodium borohydride provides the cyclopentenol (19a). Selective ester hydrolysis using for example lithium hydroxide in a solvent like a mixture of dioxane and water, provides the hydroxy substituted monoester cyclopentenol (19b).

An unsaturated P2 building block wherein $R^q$ can also be other than hydrogen, may be prepared as shown in the scheme below.

An unsaturated P2 building block, i.e. a cyclopentene ring, may be prepared as illustrated in the scheme below.

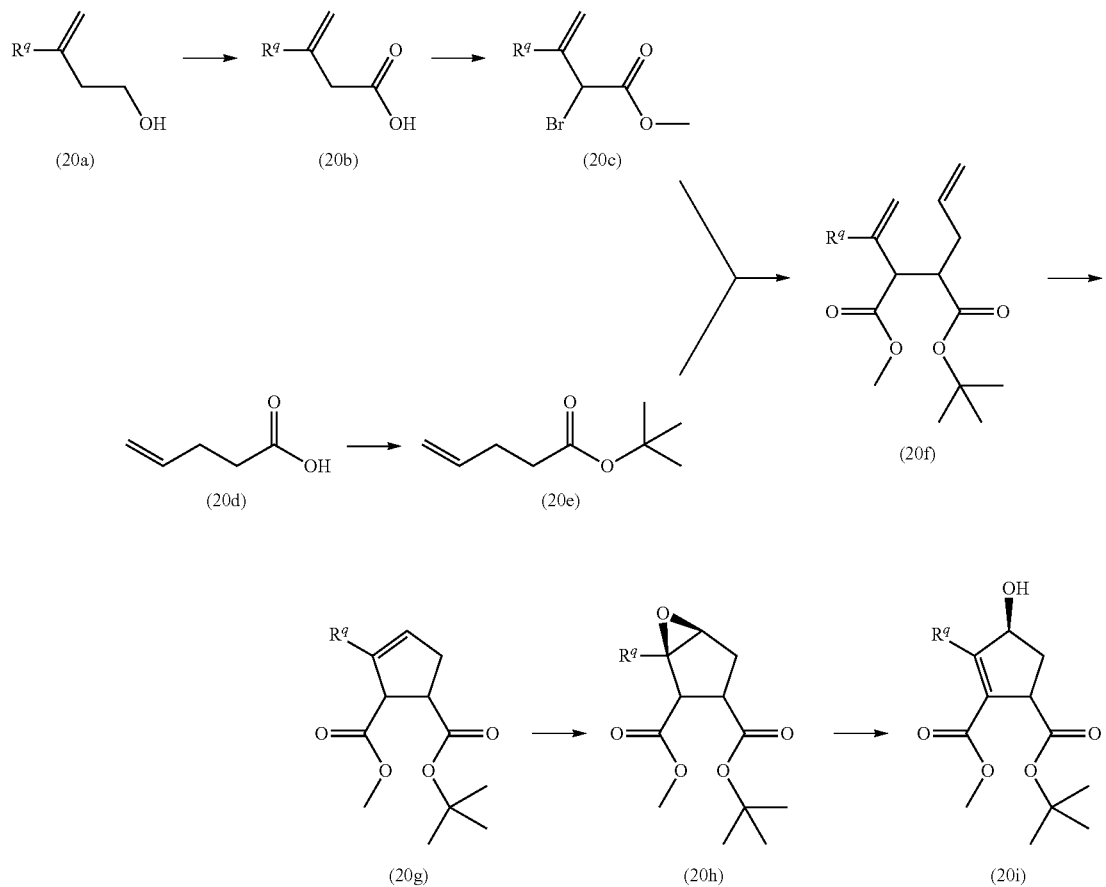

Oxidation of commercially available 3-methyl-3-buten-1-ol (20a), in particular by an oxidizing agent like pyridinium chlorochromate, yields (20b), which is converted to the corresponding methyl ester, e.g. by treatment with acetyl chloride in methanol, followed by a bromination reaction with bromine yielding the α-bromo ester (20c). The latter can then be condensed with the alkenyl ester (20e), obtained from (20d) by an ester forming reaction. The ester in (20e) preferably is a t.butyl ester which can be prepared from the corresponding commercially available acid (20d), e.g. by treatment with di-tert-butyl dicarbonate in the presence of a base like dimethylaminopyridine. Intermediate (20e) is treated with a base such as lithium diisopropyl amide in a solvent like tetrahydrofuran, and reacted with (20c) to give the alkenyl diester (20f). Cyclisation of (20f) by an olefin metathesis reaction, performed as described above, provides cyclopentene derivative (20g). Stereoselective epoxidation of (20g) can be carried out using the Jacobsen asymmetric epoxidation method to obtain epoxide (20h). Finally, an epoxide opening reaction under basic conditions, e.g. by addition of a base, in particular DBN (1,5-diazabicyclo-[4.3.0]non-5-ene), yields the alcohol (20i). Optionally, the double bond in intermediate (20i) can be reduced, for example by catalytic hydrogenation using a catalyst like palladium on carbon, yielding the corresponding cyclopentane compound. The t.butyl ester may be removed to the corresponding acid, which subsequently is coupled to a P1 building block.

The —O—$R^{10}$ group can be introduced on the pyrrolidine, cyclopentane or cyclopentene rings at any convenient stage of the synthesis of the compounds according to the present invention. One approach is to first introduce the —O—$R^{10}$ group to the said rings and subsequently add the other desired building blocks, i.e. P1 (optionally with the P1' tail) and P3, followed by the macrocycle formation. Another approach is to couple the building blocks P2, bearing no —O—$R^{10}$ substituent, with each P1 and P3, and to add the —O—$R^{10}$ group either before or after the macrocycle formation. In the latter procedure, the P2 moieties have a hydroxy group, which may be protected by a hydroxy protecting group $PG^1$.

$R^{10}$ groups can be introduced on building blocks P2 by reacting hydroxy substituted intermediates (21a) or (21b) with intermediates (4b) similar as described above for the synthesis of (I) starting from (4a). These reactions are represented in the schemes below, wherein $L^2$ is as specified above and $L^5$ and $L^{5a}$ independently from one another, represent hydroxy, a carboxyl protecting group —$OPG^2$ or —$OPG^{2a}$, or $L^5$ may also represent a P1 group such as a group (d) or (e) as specified above, or $L^{5a}$ may also represent a P3 group such as a group (b) as specified above The groups $PG^2$ and $PG^{2a}$ are as specified above. Where the groups $L^5$ and $L^{5a}$ are $PG^2$ or $PG^{2a}$, they are chosen such that each group is selectively cleavable towards the other. For example, one of $L^5$ and $L^{5a}$ may be a methyl or ethyl group and the other a benzyl or t.butyl group.

In one embodiment in (21a), $L^2$ is PG and $L^5$ is —$OPG^2$, or in (21d), $L^{5a}$ is —$OPG^2$ and $L^5$ is —$OPG^2$ and the $PG^2$ groups are removed as described above.

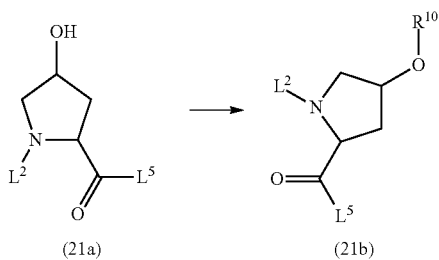

(21a)  (21b)

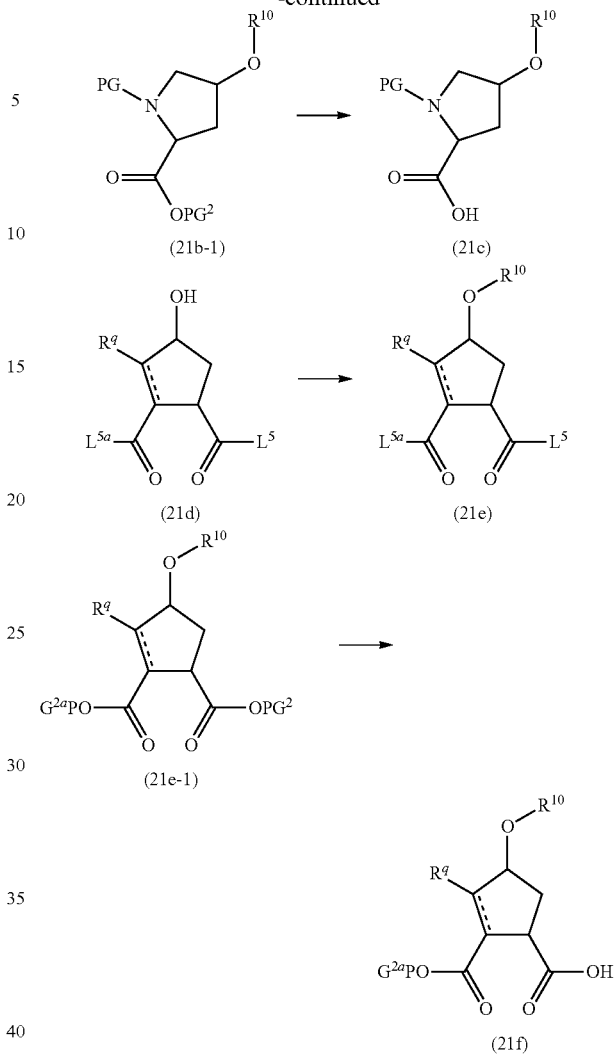

In another embodiment the group $L^2$ is BOC, $L^5$ is hydroxy and the starting material (21a) is commercially available BOC-hydroxyproline, or any other stereoisomeric form thereof, e.g. BOC-L-hydroxyproline, in particular the trans isomer of the latter. Where $L^5$ in (21b) is a carboxyl-protecting group, it may be removed following procedures described above to (21c). In still another embodiment PG in (21b-1) is Boc and $PG^2$ is a lower alkyl ester, in particular a methyl or ethyl ester. Hydrolysis of the latter ester to the acid can be done by standard procedures, e.g. acid hydrolysis with hydrochloric acid in methanol or with an alkali metal hydroxide such as NaOH, in particular with LiOH. In another embodiment, hydroxy substituted cyclopentane or cyclopentene analogs (21d) are converted to (21e), which, where $L^5$ and $L^{5a}$ are —$OPG^2$ or —$OPG^{2a}$, may be converted to the corresponding acids (21f) by removal of the group $PG^2$. Removal of $PG^{2a}$ in (21e-1) leads to similar intermediates.

Synthesis of P1 Building Blocks

The cyclopropane amino acid used in the preparation of the P1 fragment is commercially available or can be prepared using art-known procedures.

In particular the amino-vinyl-cyclopropyl ethyl ester (12b) may be obtained according to the procedure described in WO 00/09543 or as illustrated in the following scheme, wherein $PG^2$ is a carboxyl protecting group as specified above:

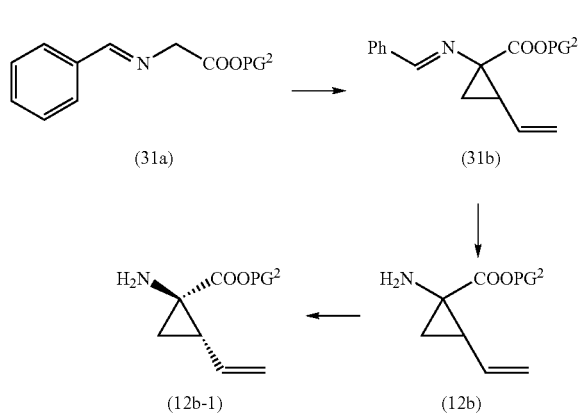

Treatment of commercially available or easily obtainable imine (31a) with 1,4-dihalo-butene in presence of a base produces (31b), which after hydrolysis yields cyclopropyl amino acid (12b), having the allyl substituent syn to the carboxyl group. Resolution of the enantiomeric mixture (12b) results in (12b-1). The resolution is performed using art-known procedures such as enzymatic separation; crystallization with a chiral acid; or chemical derivatization; or by chiral column chromatography. Intermediates (12b) or (12b-1) may be coupled to the appropriate P2 derivatives as described above.

P1 building blocks for the preparation of compounds according to general formula (I) wherein A is —COOR$^1$, —CO—NH—SO$_2$R$^2$ or —CO—NH—PO(OR$^{4a}$)(OR$^{4b}$) can be prepared by reacting amino acids (32a) with the appropriate alcohol or amine respectively under standard conditions for ester or amide formation. Cyclopropyl amino acids (32a) are prepared by introducing a N-protecting group PG, and removal of PG$^2$, and the resulting PG protected amino acids (32a) are converted to the amides (12c-1) or esters (12c-2), which are subgroups of the intermediates (12c), as outlined in the following reaction scheme, wherein PG is as specified above.

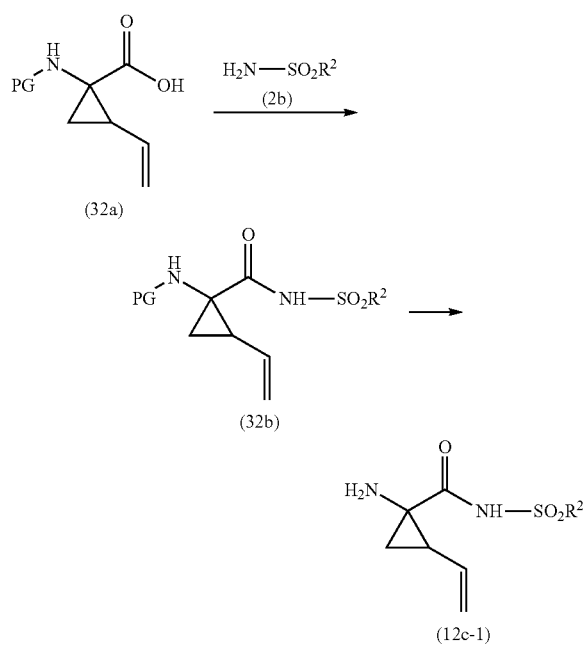

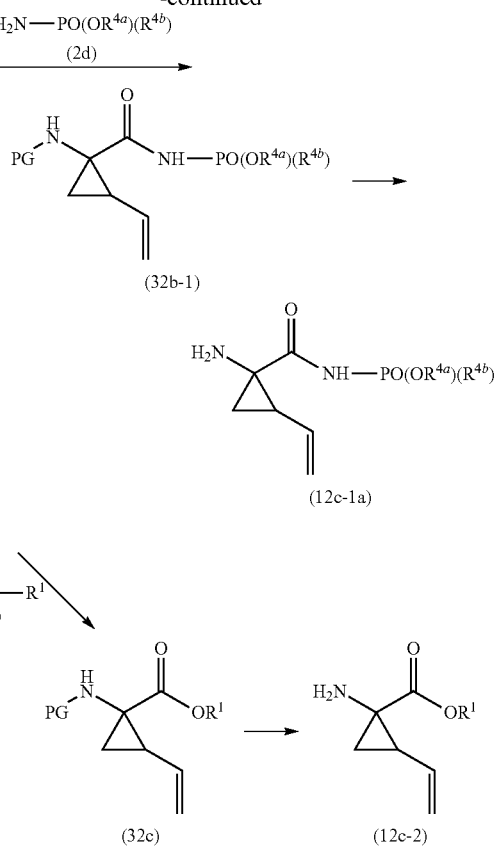

The reaction of (32a) with sulfonamideamine (2b) or with phosphoramidate (2d) is an amide forming procedure. The similar reaction with (2c) is an ester forming reaction. Both types of reaction can be performed following the procedures described above. This reaction yields intermediates (32b), (32b-1), or (32c), from which the amino protecting group is removed by standard methods such as those described above. This in turn results in the desired intermediate (12c-1), (12c-1a), or (12c-2). Starting materials (32a) may be prepared from the above-mentioned intermediates (12b) by first introducing a N-protecting group PG and subsequent removal of the group PG$^2$.

In one embodiment the reaction of (32a) with (2b) or with (2d) is done by treatment of the amino acid with a coupling agent, for example N,N'-carbonyl-diimidazole (CDI) or the like, in a solvent like THF followed by reaction with (2b) or with (2d) in the presence of a base such as 1,8-diazabicyclo[5.4.0]undec-7-ene (DBU). Alternatively the amino acid can be treated with (2b) or (2d) in the presence of a base like diisopropylethylamine followed by treatment with a coupling agent such as benzotriazole-1-yl-oxy-tris-pyrrolidino-phosphonium hexafluorophosphate (commercially available as PyBOP®) to effect the introduction of the sulfonamide group.

P1 building blocks for the preparation of compounds according to general formula (I) wherein A is —C(=O)C(=O)NR$^{3a}$R$^{3b}$ are conveniently prepared as outlined in the following scheme.

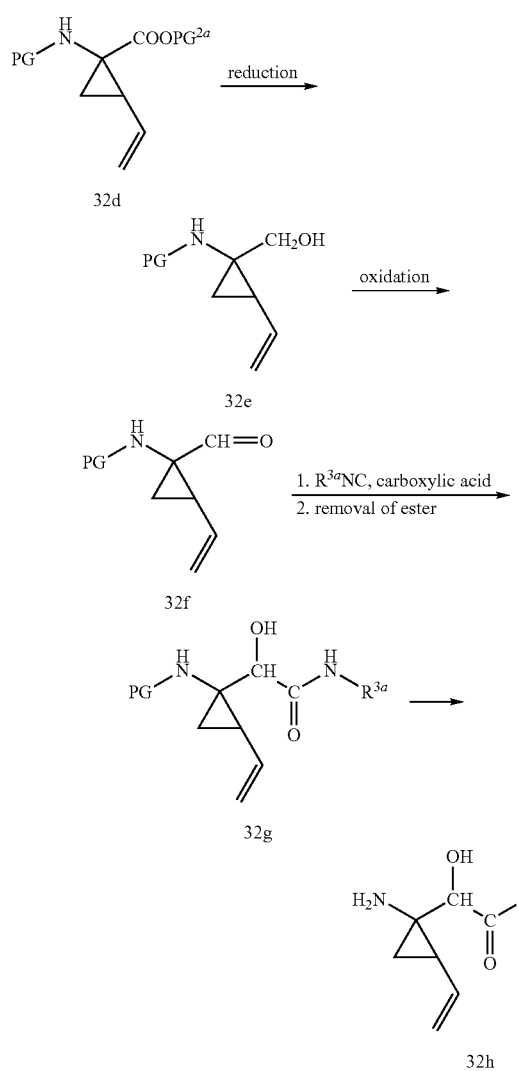

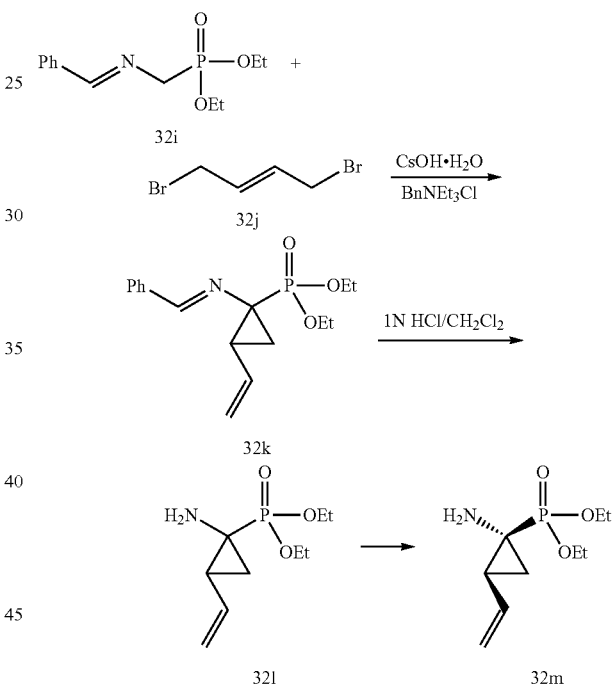

carboxylic ester are used in further reactions (such as removal of the N-protecting group, coupling with a P2 moiety, etc.). Oxidation of the α-hydroxy group of the P1 moiety is then performed at any convenient stage of the synthesis, e.g. after this coupling with a P2 moiety or at later stages of the synthesis, e.g. the last step, using a mild oxidant such as for instance Dess-Martin periodinane, thus giving compounds of formula I, or intermediates, wherein A is —C(=O)C(=O)NR$^{3a}$R$^{3b}$.

The above procedure, i.e. reduction of the ester, oxidation to the aldehyde, reaction with an isonitrile can also be performed at later stages of the synthesis procedure, e.g. after building up the macrocycle.

P1 building blocks useful for the preparation of compounds according to general formula (I) wherein A is —C(=O)NH—P(=O)(OR$^{4a}$)(R$^{4b}$), or —P(=O)(OR$^{4a}$)(R$^{4b}$) a phosphonate can be prepared following procedures described in WO 2006/020276. In particular compounds of formula (I) wherein A is —P(=O)(OR$^{4a}$)(R$^{4b}$) can be prepared as follows:

PG$^{2a}$ in starting material (32d) is an alkyl group, in particular $C_{1-6}$alkyl such as methyl or ethyl. (32d) can be obtained by an ester formation reaction of (32a) with an appropriate alkanol, or by introducing a nitrogen-protecting group PG on (12b), as described above. Reduction of the ester group in the amino acid derivative (32d) to the corresponding hydroxymethylene intermediate (32e), effected for example by treatment with lithium borohydride, followed by oxidation of the resulting hydroxymethylene group using a mild oxidant such as for instance Dess-Martin periodinane, provides the aldehyde (32f). Reaction of the latter aldehyde (32f) with a suitable isonitrile derivative and in the presence of a carboxylic acid such as trifluoroacetic acid (TFA) in the presence of a base, e.g. pyridine, in a Passerini reaction (as described, for example, in Org. Lett., Vol. 2, No 18, 2000), gives the carboxylic acid ester of the resulting α-hydroxy amide, e.g. in case of TFA, the trifluoroacetate. The carboxylic ester in the thus obtained α-hydroxy amide can then be removed using standard procedures, e.g. using basic conditions such as LiOH, thus yielding α-hydroxy amide (32g). Removal of group PG results in intermediates (32h), which can be coupled to a P2 group. The hydroxy function in (32g) can be oxidized to the corresponding α-keto amide, but in order to avoid side reactions the α-hydroxy amide or its precursor Starting material 32i is reacted with a base, in particular with CsOH, preferably in the presence of a phase transfer catalyst such as triethylbenzylammonium chloride, and 32j is added forming a cyclopropyl ring with a vinyl side chain, i.e. cyclopropyl phosphonate 32k. The phenyl-CH= protecting group is removed under acidic conditions (e.g. HCl in dichloromethane) yielding 32l. The latter can be resolved in its stereoisomers using art-known methodology, e.g. by formation of a salt with an optically active acid, for example with dibenzoyl-L-tartaric acid, which after removal of the tartaric acid derivative yields 32m. Analogues other that the ethyl phosphonates can be prepared from starting materials 32i having ester groups other than ethyl. The starting materials 32i are known materials or can easily be prepared using art-known methods.

Intermediates (12c-1) or (12c-2) in turn may be coupled to the appropriate proline, cyclopentane or cyclopentene derivatives as described above.

The pyrimidine group (i.e. radical R$^{10}$) can be introduced when preparing building blocks P2, as described above, or at a later stage of the synthesis, even as a last step.

Starting materials for the introduction of the R$^{10}$ group (e.g. R$^{10}$—OH and analogs) can be prepared as shown in the following reaction schemes.

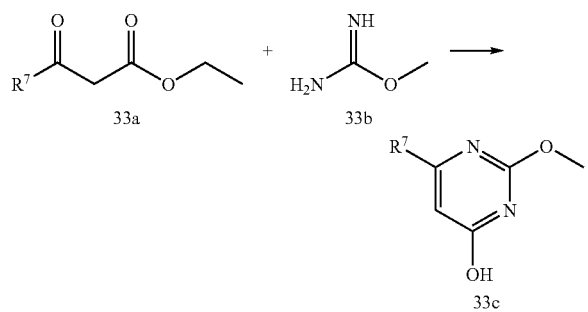

A suitably substituted β-keto ester (33a), carrying a group R$^7$ at the β-position, is reacted with 2-methylisourea (33b) in the presence of base such as sodium methoxide in a solvent like methanol, yielding the disubstituted pyrimidinol (33c).

An alternative route to various substituted pyrimidines utilises a common intermediate, which subsequently can be transformed into pyrimidine derivatives with diverse substitution patterns. A route to this intermediate (34d) is as follows.

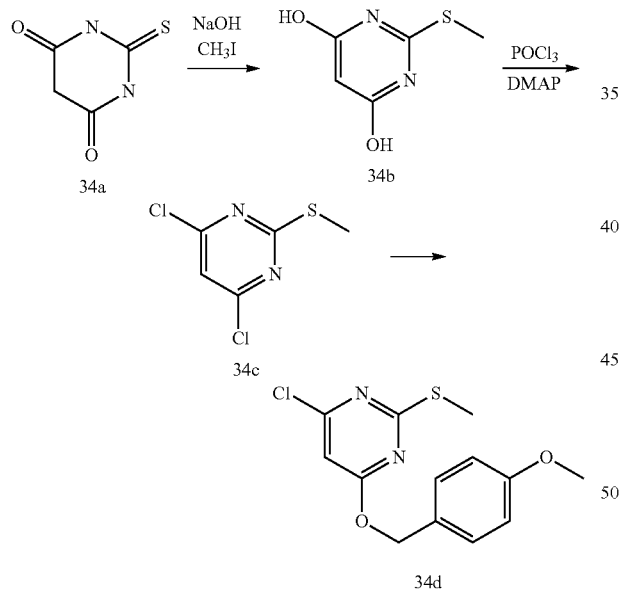

Selective alkylation of the sulphur atom of thiobarbituric acid (34a) by treatment with methyl iodide, or any other similar alkylating agent, in the presence of a base such as sodium hydroxide or the like, provides the thio ether derivative (34b). Substitution of the hydroxy group by chloro with an halogenating agent, for example by treatment with phosphorus trichloride in the presence of a base, such as dimethyl aminopyridine or the like, yields (34c) followed by reaction with a suitable derivative of benzyl alcohol, for example p-methoxybenzyl alcohol, in the presence of a base such as NaH provides the methoxybenzyl protected pyrimidinol (34d).

In a further aspect, this invention concerns intermediate (34d), a new compound that serves as a convenient intermediate to prepare compounds of formula (I). Intermediate (34d) offers large flexibility for the further synthesis since it can be selectively reacted at different positions of the pyrimidine ring in any desired order, either at this stage or at a later stage, for example at the end of the synthesis. For example, the thioether function can be oxidized to the corresponding sulfone followed by a nucleophilic substitution reaction with different nucluphiles, such as Grignard reagents, alcoholates or amines, to give pyrimidines carrying a C—, O- or N-linked substituent respectively, at the 2-position. Alternatively, the chloro substituent can be replaced by a desired alcoholate such as methoxide or the like, or Stille or Suzuki coupling conditions can be used in order to introduce a C-linked substituent for example an aryl or heteroaryl group.

The following scheme illustrates a method to introduce O-linked and C-linked substituents at positions 4 and 2 respectively of the pyrimidinol (3d).

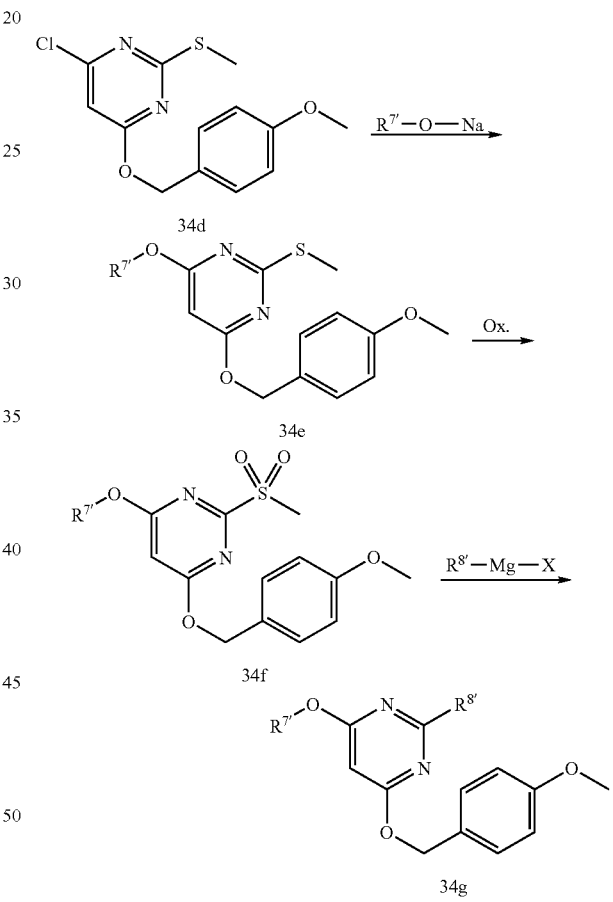

R$^7$ and R$^8$ are independently C$_1$-C$_6$alkyl, carbocyclyl or heterocyclyl
X is Cl, Br or I Substitution of the chloro substituent in (34d) by an alkoxylating agent, such as an alkali metal alkoxide, yields ether derivative (34e). Oxidation of the sulphur using a suitable oxidant, e.g. m.chlorophenyl mCPBA, to (34f), followed by substitution of the sulphone group in (34f) by using a suitable Grignard reagent provides the alkylated pyrimidinol (34g).

A C-linked substituent can be introduced at position 4 of the intermediate pyrimidinol derivative 3d for example by way of a Suzuki or Stille coupling as illustrated in the following scheme.

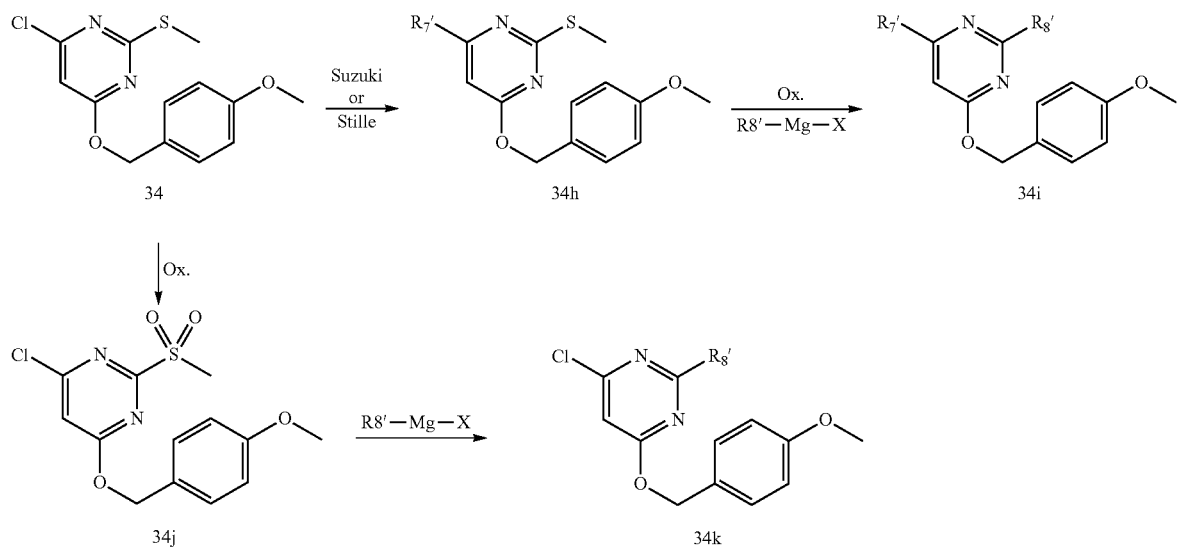

$R_7'$ and $R_8'$ are independently $C_{1-6}$alkyl, carbocyclyl or heterocyclyl
X is Cl, Br or I Subjecting the chloro compound (34d) to Suzuki or Stille coupling conditions provides the alkylated compound (34h) which subsequently can be oxidized to the sulphone and then reacted with a desired nucleophile for example a Grignard reagent as described above, to give the dialkylated pyrimidinol (34i). Alternatively, the oxidation-substitution step of the intermediate (34d) can be performed first obtaining (34j) and the chloro substituent substituted with a suitable nucleophile either directly afterwards yielding (34k) or at a later stage of the synthesis, for example as the last step, when the pyrimidine derivative is coupled to the P2 moiety.

Synthesis of the P3 Building Blocks

The P3 building blocks are available commercially or can be prepared according to methodologies known to the skilled in the art. One of these methodologies is shown in the scheme below and uses monoacylated amines, such as trifluoroacetamide or a Boc-protected amine

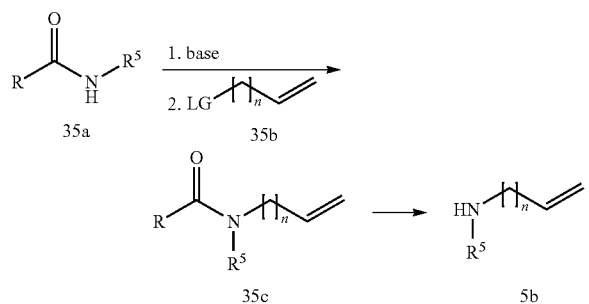

In the above scheme, R together with the CO group forms a N-protecting group, in particular R is t-butoxy, trifluoromethyl; $R^5$ and n are as defined above and LG is a leaving group, in particular halogen, e.g. chloro or bromo.

The monoacylated amines (33a) are treated with a strong base such as sodium hydride and are subsequently reacted with a reagent LG-$C_{5-8}$alkenyl (33b), in particular halo$C_{5-8}$alkenyl, to form the corresponding protected amines (33c). Deprotection of (33c) affords (5b), which are building blocks P3. Deprotection will depend on the functional group R, thus if R is t-butoxy, deprotection of the corresponding Boc-protected amine can be accomplished with an acidic treatment, e.g. trifluoroacetic acid. Alternatively, when R is for instance trifluoromethyl, removal of the R group is accomplished with a base, e.g. sodium hydroxide.

The following scheme illustrates yet another method for preparing a P3 building block, namely a Gabriel synthesis of primary $C_{5-8}$alkenylamines, which can be carried out by the treatment of a phthalimide (34a) with a base, such as NaOH or KOH, and with (33b), which is as specified above, followed by hydrolysis of the intermediate N-alkenyl imide to generate a primary $C_{5-8}$alkenylamine (5b-1).

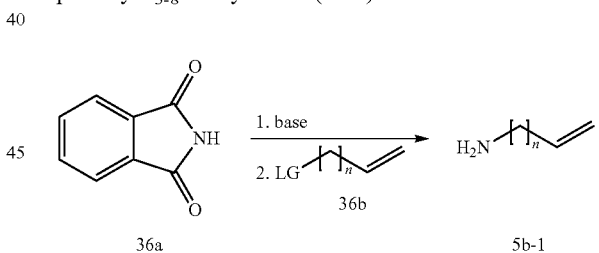

In the above scheme, n is as defined above.

Compounds of formula (I) may be converted into each other following art-known functional group transformation reactions. For example, amino groups may be N-alkylated, nitro groups reduced to amino groups, a halo atom may be exchanged for another halo.

A number of the intermediates used to prepare the compounds of formula (I) are known compounds or are analogues of known compounds, which can be prepared following modifications of art-known methodologies readily accessible to the skilled person.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I) that are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to act in a prophylactic way against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviruses the diseases include yellow fever, dengue fever, hemorraghic fever and encephalitis. A number of the compounds of this invention moreover are active against mutated strains of HCV. Additionally, many of the compounds of this invention show a favorable pharmacokinetic profile and have attractive properties in terms of bioavailability, including an acceptable half-life, AUC (area under the curve) and peak values and lacking unfavourable phenomena such as insufficient quick onset and tissue retention.

The in vitro antiviral activity against HCV of the compounds of formula (I) can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, N-oxides, pharmaceutically acceptable addition salts, and stereochemically isomeric forms, are useful in the treatment of individuals infected with a virus, particularly a virus that is HCV, and for the prophylaxis of viral infections, in particular HCV infections. In general, the compounds of the present invention may be useful in the treatment of warm-blooded animals infected with viruses, in particular flaviviruses such as HCV.

The compounds of the present invention or any subgroup thereof may therefore be used as a medicine. Said use as a medicine or method of treatment comprises the systemic administration to virally infected subjects or to subjects susceptible to viral infections of an amount effective to combat the conditions associated with the viral infection, in particular HCV infection.

The present invention also relates to the use of the present compounds or any subgroup thereof in the manufacture of a medicament for the treatment or the prevention of a viral infection, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

In general it is contemplated that an antiviral effective daily amount would be from 0.01 mg/kg to 500 mg/kg body weight, or from 0.1 mg/kg to 50 mg/kg body weight, or from 0.5 mg/kg to 5 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

The invention also relates to a combination of a compound of formula (I), including a stereoisomeric form thereof, a pharmaceutically acceptable salt, or a pharmaceutically acceptable solvate thereof, and another antiviral compound, in particular another anti-HCV compound. The term "combination" may relate to a product containing (a) a compound of formula (I), as specified above, and (b) optionally another anti-HCV compound, as a combined preparation for simultaneous, separate or sequential use in treatment of HCV infections.

Anti-HCV compounds that can be used in such combinations include agents selected from an HCV polymerase inhibitor, an HCV protease inhibitor, an inhibitor of another target in the HCV life cycle, and an immunomodulatory agent, and combinations thereof. HCV polymerase inhibitors include, NM283 (valopicitabine), R803, JTK-109, JTK-003, HCV-371, HCV-086, HCV-796 and R-1479 Inhibitors of HCV proteases (NS2-NS3 inhibitors and NS3-NS4A inhibitors) include the compounds of WO 02/18369 (see, e.g., page 273, lines 9-22 and page 274, line 4 to page 276, line 11); BILN-2061, VX-950, GS-9132 (ACH-806), SCH-503034, and SCH-6. Further agents that can be used are those disclosed in WO 98/17679, WO 00/056331 (Vertex); WO 98/22496 (Roche); WO 99/07734, (Boehringer Ingelheim), WO 2005/073216, WO 2005/073195 (Medivir) and structurally similar agents.

Inhibitors of other targets in the HCV life cycle, including NS3 helicase; metallo-protease inhibitors; antisense oligonucleotide inhibitors, such as ISIS-14803, AVI-4065 and the like; siRNA's such as SIRPLEX-140-N and the like; vector-encoded short hairpin RNA (shRNA); DNAzymes; HCV specific ribozymes such as heptazyme, RPI.13919 and the like; entry inhibitors such as HepeX-C, HuMax-HepC and the like; alpha glucosidase inhibitors such as celgosivir, UT-231B and the like; KPE-02003002; and BIVN 401.

Immunomodulatory agents include, natural and recombinant interferon isoform compounds, including α-interferon, β-interferon, γ-interferon, ω-interferon and the like, such as Intron A®, Roferon-A®, Canferon-A300®, Advaferon®, Infergen®, Humoferon®, Sumiferon MP®, Alfaferone®, IFN-beta®, Feron® and the like; polyethylene glycol derivatized (pegylated) interferon compounds, such as PEG interferon-α-2a (Pegasys®), PEG interferon-α-2b (PEG-Intron®), pegylated IFN-α-con1 and the like; long acting formulations and derivatizations of interferon compounds such as the albumin-fused interferon albuferon α and the like; compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isatoribine and the like; thymosin α-1; ANA-245; ANA-246; histamine dihydrochloride;

propagermanium; tetrachlorodecaoxide; ampligen; IMP-321; KRN-7000; antibodies, such as civacir, XTL-6865, and the like; and prophylactic and therapeutic vaccines such as InnoVac C, HCV E1E2/MF59, and the like.

Other antiviral agents include, ribavirin, amantadine, viramidine, nitazoxanide; telbivudine; NOV-205; taribavirin; inhibitors of internal ribosome entry; broad-spectrum viral inhibitors, such as IMPDH inhibitors, and mycophenolic acid and derivatives thereof, and including, but not limited to VX-950, merimepodib (VX-497), VX-148, and/or VX-944); or combinations of any of the above.

Particular agents for use in said combinations include interferon-α (IFN-α), pegylated interferon-α or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

In another aspect there are provided combinations of a compound of formula (I) as specified herein and an anti-HIV compound. The latter preferably are those HIV inhibitors that have a positive effect on drug metabolism and/or pharmacokinetics that improve bioavailability. An example of such an HIV inhibitor is ritonavir. As such, this invention further provides a combination comprising (a) an HCV NS3/4a protease inhibitor of formula (I) or a pharmaceutically acceptable salt thereof; and (b) ritonavir or a pharmaceutically acceptable salt thereof. The compound ritonavir, its pharmaceutically acceptable salts, and methods for its preparation are described in WO 94/14436. U.S. Pat. No. 6,037,157, and references cited therein: U.S. Pat. No. 5,484,801, U.S. Ser. No. 08/402,690, WO95/07696, and WO95/09614, disclose preferred dosage forms of ritonavir. One embodiment relates to a combination comprising (a) an HCV NS3/4a protease inhibitor of formula (I) or a pharmaceutically acceptable salt thereof; and (b) ritonavir or a pharmaceutically acceptable salt thereof; optionally comprising an additional anti-HCV compound selected from the compounds mentioned above.

The invention also concerns a process for preparing a combination as described herein, comprising the step of combining a compound of formula (I), as specified above, and another agent, such as an antiviral, including an anti-HCV or anti-HIV agent, in particular those mentioned above.

The said combinations may find use in the manufacture of a medicament for treating HCV infection, or another pathogenic flavi- or pestivirus, in a mammal infected with therewith, said combination in particular comprising a compound of formula (I), as specified above and interferon-α (IFN-α), pegylated interferon-α, or ribavirin. Or the invention provides a method of treating a mammal, in particular a human, infected with HCV, or another pathogenic flavi- or pestivirus, comprising the administration to said mammal of an effective amount of a combination as specified herein. In particular, said treating comprises the systemic administration of the said combination and an effective amount is such amount that is effective in treating the clinical conditions associated with HCV infection.

In one embodiment the above-mentioned combinations are formulated in the form of a pharmaceutical composition that includes the active ingredients described above and a carrier, as described above. Each of the active ingredients may be formulated separately and the formulations may be co-administered, or one formulation containing both and if desired further active ingredients may be provided. In the former instance, the combinations may also be formulated as a combined preparation for simultaneous, separate or sequential use in HCV therapy. The said composition may take any of the forms described above. In one embodiment, both ingredients are formulated in one dosage form such as a fixed dosage combination. In a particular embodiment, the present invention provides a pharmaceutical composition comprising (a) a therapeutically effective amount of a compound of formula (I), including a stereoisomeric form thereof, or a pharmaceutically acceptable salt thereof, or a pharmaceutically acceptable solvate thereof, and (b) a therapeutically effective amount of ritonavir or a pharmaceutically acceptable salt thereof, and (c) a carrier.

The individual components of the combinations of the present invention can be administered separately at different times during the course of therapy or concurrently in divided or single combination forms. The present invention is meant to embrace all such regimes of simultaneous or alternating treatment and the term "administering" is to be interpreted accordingly. In a preferred embodiment, the separate dosage forms are administered simultaneously.

In one embodiment, the combinations of the present invention contains an amount of ritonavir, or a pharmaceutically acceptable salt thereof, that is sufficient to clinically improve the bioavailability of the HCV NS3/4a protease inhibitor of formula (I) relative to the bioavailability when said HCV NS3/4a protease inhibitor of formula (I) is administered alone. Or, the combinations of the present invention contains an amount of ritonavir, or a pharmaceutically acceptable salt thereof, which is sufficient to increase at least one of the pharmacokinetic variables of the HCV NS3/4a protease inhibitor of formula (I) selected from $t_{1/2}$, $C_{min}$, $C_{max}$, $C_{ss}$, AUC at 12 hours, or AUC at 24 hours, relative to said at least one pharmacokinetic variable when the HCV NS3/4a protease inhibitor of formula (I) is administered alone.

The combinations of this invention can be administered to humans in dosage ranges specific for each component comprised in said combinations, e.g. the compound of formula (I) as specified above, and ritonavir or a pharmaceutically acceptable salt, may have dosage levels in the range of 0.02 to 5.0 g/day.

The weight ratio of the compound of formula (I) to ritonavir may be in the range of from about 30:1 to about 1:15, or about 15:1 to about 1:10, or about 15:1 to about 1:1, or about 10:1 to about 1:1, or about 8:1 to about 1:1, or about 1:5 to 1:1 to about 5:1, or about 3:1 to about 1:1, or about 2:1 to 1:1. The compound formula (I) and ritonavir may be co-administered once or twice a day, preferably orally, wherein the amount of the compound of formula (I) per dose is from about 1 to about 2500 mg, or about 50 to about 1500 mg, or about 100 to about 1000 mg, or about 200 to about 600 mg, or about 100 to about 400 mg; and the amount of ritonavir per dose is from 1 to about 2500 mg, or about 50 to about 1500 mg, or about 100 to about 800 mg, or about 100 to about 400 mg, or 40 to about 100 mg of ritonavir.

EXAMPLES

The following examples are intended to illustrate the present invention and not to limit it thereto. Some examples show the preparation of building blocks, which may be coupled to any other appropriate building block described herein and not only to the building blocks of the exemplified end products of formula I.

Example 1

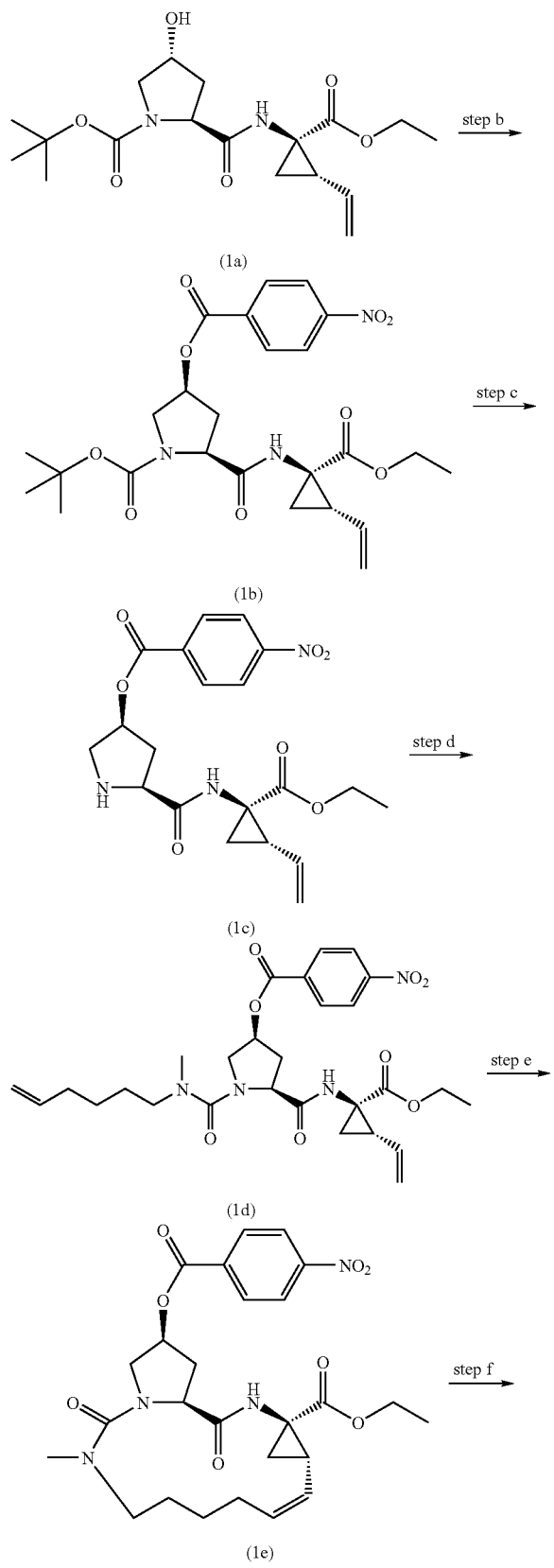

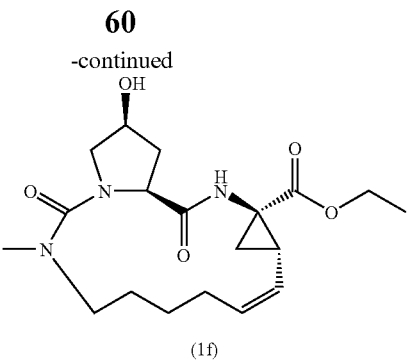

Step a: 2-(1-Ethoxycarbonyl-2-vinyl-cyclopropylcarbamoyl)-4-hydroxy-pyrrolidine-1-carboxylic acid tert-butyl ester (1a)

Boc-protected 4-hydroxy proline (4 g, 17.3 mmol), HATU (6.9 g, 18.2 mmol) and 1-amino-2-vinyl-cyclopropanecarboxylic acid ethyl ester prepared as described in WO03/099274, (3.5 g, 18.3 mmol) were dissolved in dimethylformamide (DMF) (60 ml) and cooled to 0° on an ice-bath. Diisopropylethyl amine (DIPEA) (6 ml) was added. The ice-bath was removed and the mixture was left at ambient temperature over-night. Dichloromethane (DCM) (~80 ml) was then added and the organic phase was washed with aqueous sodium hydrogen carbonate, citric acid, water, brine and dried over sodium sulfate. Purification by flash chromatography (ether→>7% methanol in ether) gave pure title compound (6.13 g, 96%).

Step b: 2-(1-Ethoxycarbonyl-2-vinyl-cyclopropylcarbamoyl)-4-(4-nitro-benzoyloxy)-pyrrolidine-1-carboxylic acid tert-butyl ester (1b)

The compound from step a (6.13 g, 16.6 mmol), 4-nitrobenzoic acid (4.17 g, 25 mmol) and PPh$_3$ (6.55 g, 25 mmol) was dissolved in tetrahydrofuran (THF) (130 ml). The solution was cooled to ~0° C. and diisopropyl azidocarboxylate (5.1 g, 25 mmol) was added slowly. The cooling was then removed and the mixture was left over-night at ambient condition. Aqueous sodium hydrogen carbonate (60 ml) was added and the mixture was extracted with dichloromethane. Purification by flash chromatography (pentane-ether, 2:1→pentane-ether, 1:2→2% methanol in ether) gave pure title compound (6.2 g, 72%).

Step c: 4-Nitro-benzoic acid 5-(1-ethoxycarbonyl-2-vinyl-cyclopropylcarbamoyl)-pyrrolidin-3-yl ester (1c)

The compound from step b (6.2 g, 12 mmol) was dissolved in an ice-cold mixture of trifluoromethanesulfonic acid 33% in dichloromethane. The ice-bath was then removed and the mixture was left at room temperature for ~1.5 h. The solvent was evaporated and 0.25 M sodium carbonate added and the mixture was extracted with dichloromethane. Evaporation gave the title compound (4.8 g, 95%) as a yellowish powder.

Step d: 4-Nitro-benzoic acid 5-(1-ethoxycarbonyl-2-vinyl-cyclopropylcarbamoyl)-1-(hex-5-enyl-methyl-carbamoyl)-pyrrolidin-3-yl ester (1d)

The amine 1c (4.5 g, 10.8 mmol) was dissolved in THF (160 ml). A tablespoon of sodium hydrogen carbonate was added followed by phosgene (11.3 ml, 20% in toluene). The mixture was stirred vigorously for 1 h. The mixture is filtrated and re-dissolved in dichloromethane (160 ml). Sodium hydrogen carbonate (~a tablespoon) was added followed by the amine hydrochloride (2.9 g, 21.6 mmol). The reaction was the left in room temperature over night. Purification by flash chromatography (ether→3% methanol in ether) gave pure title compound (5.48 g, 91%), Step e: 13-Methyl-17-(4-nitro-benzoyloxy)-2,14-dioxo-3,13,15-triazatricyclo-[13.3.0.0*4,6*]octadec-7-ene-4-carboxylic acid ethyl ester (1e)

The diene 1d (850 mg, 1.53 mmol) was dissolved in 1.5 l degassed and dried 1,2-dichloroethane and refluxed under argon atmosphere over night. Scavenger (MP-TMT, P/N 800470 from Argonaut technologies, ~½ teaspoon) was added and the mixture was stirred for 2 h, filtrated and concentrated by reduced pressure. The crude product was crystallized from dichloromethane/n-hexane to yield the title compound (600 mg, 74%).

Step f: 17-Hydroxy-13-methyl-2,14-dioxo-3,13,15-triaza-tricyclo[13.3.0.0*4,6*1]-octadec-7-ene-4-carboxylic acid ethyl ester (1f)

Compound 1e (200 mg, 0.38 mmol) was dissolved in a mixture of methanol/THF/water, 1:2:1, (20 ml) and cooled on ice-bath. Lithium hydroxide (1.9 ml, 1M) was added slowly. The mixture was stirred for 4 h at 0° C., then neutralized with aqueous acetic acid (20 ml) and extracted with dichloromethane. The organic phase was washed with bicarbonate, water, brine and dried over magnesium sulfate. Purification by chromatography (2% methanol in dichloromethane→4%) gave the title compound as a grayish powder (80%).

Step g: 2-Methoxy-6-phenylpyrimidin-4-ol (1g)

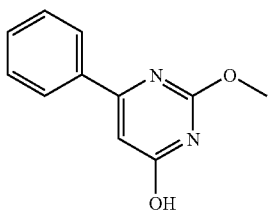

(1g)

Sodium (4.14 g, 180 mmol) was dissolved in dry methanol (120 ml) and the solution was cooled to 0-5° C. O-Methylisourea sulfat (10.3 g, 60 mmol) and ethyl benzoylacetate (11.5 g, 60 mmol) was added and the mixture was stirred for two hours at room temperature and then refluxed for twelve hours. The mixture was evaporated, acidified with 2M HCl and extracted three tines with ethyl acetate and three times with DCM. The organic phase was dried and evaporated and the residue was suspended in diethyl ether, the solid filtered off, washed and dried which gave the title compound, (1.0 g) MS+1=203.

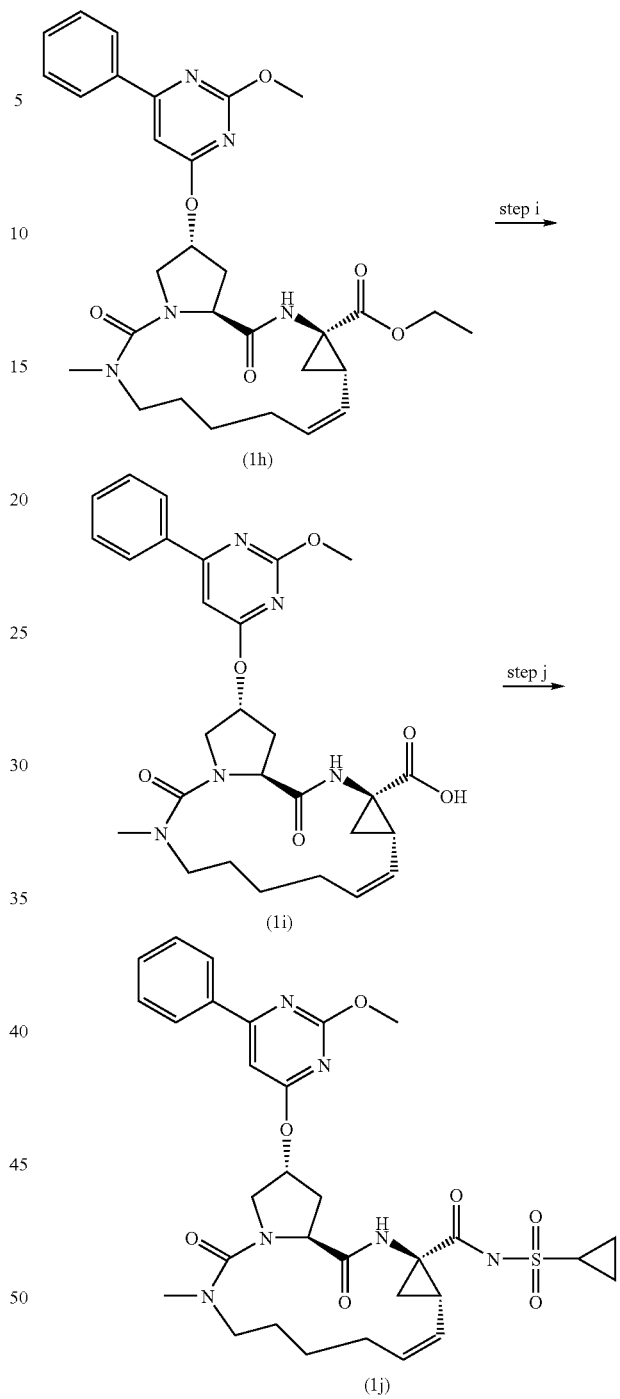

Step h: 17-(2-Methoxy-6-phenyl-pyrimidin-4-yloxy)-13-methyl-2,14-dioxo-3,13,15-triaza-tricyclo[13.3.0.0*4,6*]octa dec-7-ene-4-carboxylic acid ethyl ester (1 h)

Compound 1f (250 mg, 0.659 mmol), and compound 1g (160 mg, 0.791 mmol) and PPh₃ (432 mg, 1.648 mmol) were suspended in THF (30 ml) and DMF (2 ml) at 0° C. DIAD (0.32 ml, 1.648 mmol) was added and the reaction mixture was stirred at room temperature over night. Ether was added and some PPh₃O was filtered off. The reaction mixture was

Step i: 17-(2-Methoxy-6-phenyl-pyrimidin-4-yloxy)-13-methyl-2,14-dioxo-3,13,15-triaza-tricyclo [13.3.0.0*4,6*]octa dec-7-ene-4-carboxylic acid (1i)

Compound 1h (95 mg, 0.169 mmol) was dissolved in a 2:1:1 mixture of THF:MeOH:H₂O (24 ml). LiOH (1M, 1.7 ml) was added and the mixture was allowed to stir at room temperature over night. 5% Citric acid was added followed by DCM and after extraction the organic layer was dried (MgSO₄), filtered and evaporated. The residue was purified by column chromatography (DCM/MeOH 98/2→4/6) which gave the title compound (78 mg, 86%), MS (M+H)⁺536.

Step j: Cyclopropanesulfonic acid [17-(2-methoxy-6-phenyl-pyrimidin-4-yloxy)-13-methyl-2,14-dioxo-3,13,15-triaza-tricyclo[13.3.0.0*4,6*]octadec-7-ene-4-carbonyl]-amide (1j)

Compound 1i (78 mg, 0.146 mmol) and EDAC (34 mg, 0.175 mmol) were dissolved in DCM (3 ml). The reaction mixture was stirred at room temperature for 1 h (LC-MS indicated presence of the intermediate). Cyclopropane sulphonic amide (20 mg, 0.161 mmol) and DBU (46 µl, 0.307 mmol) were added and the reaction mixture was stirred at RT for 3.5 h. Citric acid (5%) was added and the organic layer was separated and washed with brine, dried (MgSO₄), filtered and evaporated. The residue was purified by preparative HPLC which gave the pure title compound (50 mg, 54%), (M+H)⁺639).

Example 2

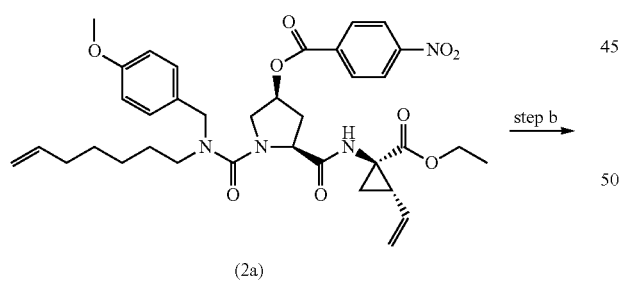

(2a)

step b →

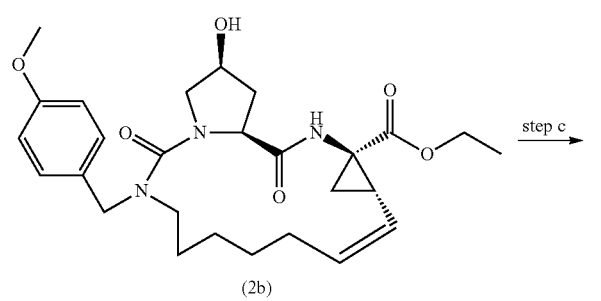

(2b)

step c →

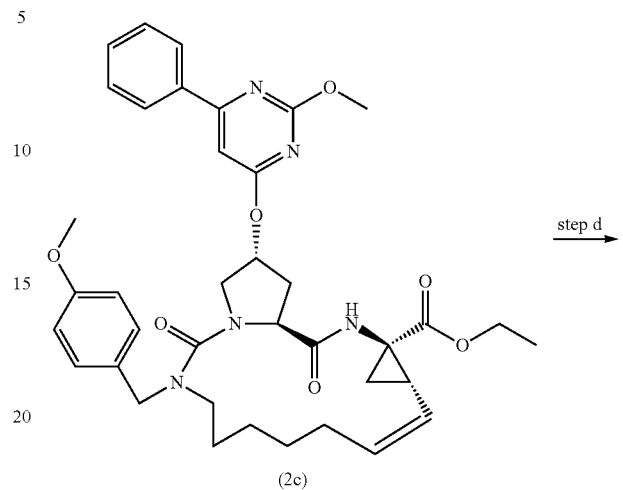

(2c)

step d →

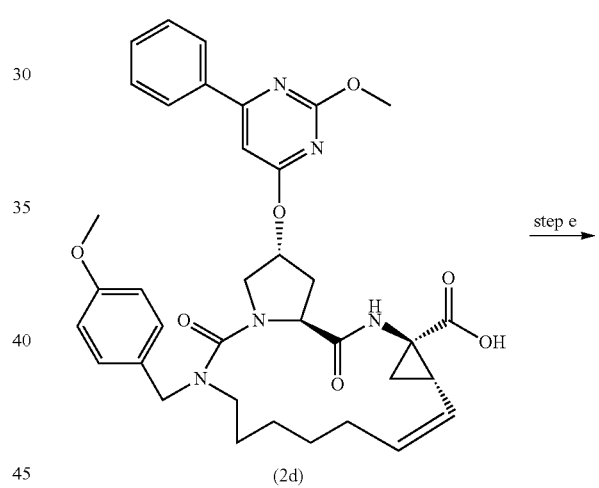

(2d)

step e →

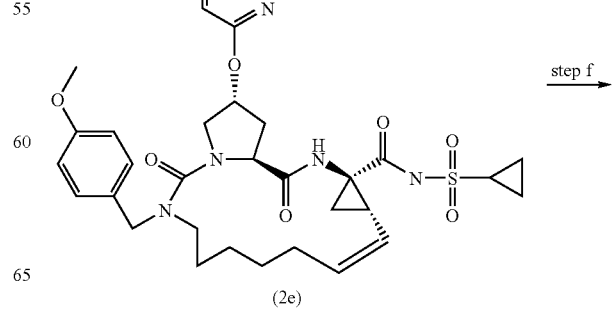

(2e)

step f →

-continued

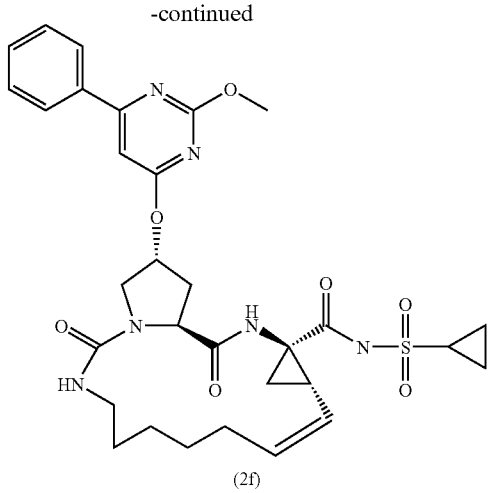

(2f)

Step a: 4-Nitro-benzoic acid 5-(1-ethoxycarbonyl-2-vinyl-cyclopropylcarbamoyl)-1-[hept-6-enyl-(4-methoxy-benzyl)-carbamoyl]-pyrrolidin-3-yl ester (2a)

To a solution of compound 1c (4.5 g, 10.8 mmol) in THF (160 mL) was added NaHCO$_3$ (1 tablespoon) and phosgene in toluene (1.93 M, 11.5 mL, 22 mmol). The mixture was vigorously stirred for 1 h at room temperature, and then filtered and evaporated. The residue was dissolved in CH$_2$Cl$_2$ (160 mL), and NaHCO$_3$ (1 tablespoon) and hept-5-enyl-(p-methoxybenzyl)-amine (4.3 g, 18.5 mmol) were added. After stirring overnight at room temperature the reaction mixture was filtered and evaporated to dryness. Flash column chromatography on silica gel (EtOAc:toluene 25:75→40:60) gave the title compound (6.59 g, 90%) as a light brown syrup.

Step b: 18-Hydroxy-14-(4-methoxy-benzyl)-2,15-dioxo-3,14,16-triaza-tricyclo-[14.3.0.0*4,6*]nonadec-7-ene-4-carboxylic acid ethyl ester (2b)

Compound 2a (1 g, 1.48 mmol) was dissolved in 1,2-dichloroethane (2 l). The mixture was degassed for 15 min using a stream of argon. Hoveyda-Grubbs catalyst (II) (50 mg, 5 mol %) was added and the mixture was refluxed for 4 h. The solvent was evaporated and the crude ester was dissolved in THF (100 ml), methanol (50 ml) and water (50 ml). The mixture was cooled to 0° C. on an ice-bath. Aqueous lithium hydroxide (20 ml, 1M) was added and the mixture was stirred at 0° C. for 4 h. The volume was then doubled by addition of water and the mixture was acidified with acetic acid. Extraction (dichloromethane) followed by flash column chromatography (methanol 1→5% in ether) gave pure title compound (450 mg, 61%).
MS (M+H)$^+$500.

Step c: 14-(4-Methoxy-benzyl)-18-(2-methoxy-6-phenyl-pyrimidin-4-yloxy)-2,15-dioxo-3,14,16-triaza-tricyclo[14.3.0.0*4,6*]nonadec-7-ene-4-carboxylic acid ethyl ester (2c)

The alcohol 2b (500 mg, 1 mmol), pyrimidinol (1 g) (243 mg, 1.2 mmol), PPh$_3$ (656 mg, 2.5 mmol) and DIAD (0.49 ml, 2.5 mmol) were dissolved in THF (40 ml) and DMF (3 ml). The reaction mixture was stirred at RT over night. The solvent was evaporated, ether was added and PPh$_3$O was filtered off.

Purification by column chromatography, toluene/EtOAc 9:1, gave of the title compound (680, 99%) MS (M+H)$^+$684.

Step d: 14-(4-Methoxybenzyl)-18-(2-methoxy-6-phenylpyrimidin-4-yloxy)-2,15-dioxo-3,14,16-triaza-tricyclo[14.3.0.0*4,6*]nonadec-7-ene-4-carboxylic acid (2d)

Compound 2c (0.680 mg, 0.996 mmol) was dissolved in a 2:1:1 mixture of THF:MeOH:H$_2$O (144 ml). LiOH (1 M, 10 ml) was added and the reaction mixture was stirred at RT overnight. 5% Citric acid was added, followed by DCM. The organic layer was separated, dried (MgSO$_4$), filtered and evaporated. The residue was purified by column chromatography, DCM: MeOH 9:1 which the title compound (380 mg, 58%), MS (M+H)$^+$656.

Step e: Cyclopropanesulfonic acid [14-(4-methoxy-benzyl)-18-(2-methoxy-6-phenyl-pyrimidin-4-yloxy)-2,15-dioxo-3,14,16-triaza-tricyclo [14.3.0.0*4,6*]nonadec-7-ene-4-carbonyl]amide (2e)

Compound 2d (200 mg, 0.305 mmol) was dissolved in DCM (10 ml). EDAC (70 mg, 0.366 mmol) was added and the reaction mixture was stirred at RT for 30 min. Cyclopropanesulfonic amide (41 mg, 0.336 mmol) and DBU (96 µl, 0.641 mmol) were added and the reaction was stirred at RT for 72 h. 5% Citric acid was added and the organic layer was separated and washed with brine, dried, filtered and evaporated. This material was used directly in the following step without further purification.

Step f: Cyclopropanesulfonic acid [18-(2-methoxy-6-phenylpyrimidin-4-yloxy)-2,15-dioxo-3,14,16-triaza-tricyclo[14.3.0.0*4,6*]nonadec-7-ene-4-carbonyl]-amide (2f)

Compound 2e was dissolved in a 1:2 mixture of TFA:DCM (12 ml) and stirred at RT for 1 h. NaHCO$_3$ was added and the organic layer was separated, dried, filtered and evaporated. The residue was purified by preparative HPLC which gave the pure title compound (32 mg, 16% over two steps). MS (M+H)$^+$639.

Example 3

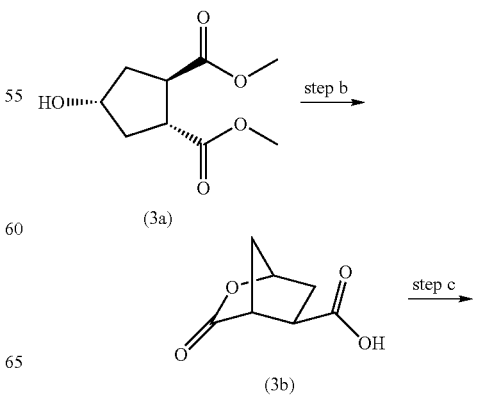

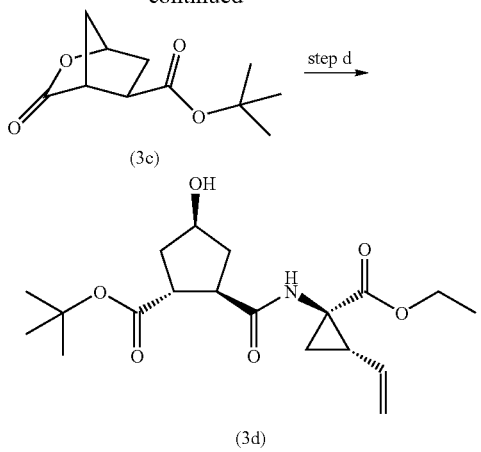

Step a: 4-Hydroxy-cyclopentane-1,2-dicarboxylic acid dimethyl ester (3a)

Sodium borohydride (1.11 g, 0.029 mol) was added to a stirred solution of (1R,2S)-4-oxo-cyclopentane1,2-dicarboxylic acid dimethyl ester (4.88 g, 0.0244 mol) in methanol (300 mL) at 0° C. After 1 h the reaction was quenched with 90 ml brine, concentrated and extracted with ethyl acetate. The organic phases were pooled, dried, filtered and concentrated. The crude product was purified by flash column chromatography (toluene/ethyl acetate 1:1) which gave the title compound (3.73 g, 76%) as a yellow oil.

Step b: 3-Oxo-2-oxa-bicyclo[2.2.1]heptane-5-carboxylic acid (3b)

Sodium hydroxide (1M, 74 mL, 0.074 mol) was added to a stirred solution of compound 3a (3.73 g, 0.018 mol) in methanol (105 mL) at room temperature. After 4 h, the reaction mixture was neutralized with 3M HCl, evaporated and co-evaporated with toluene several times. Pyridine (75 mL) and Ac$_2$O (53 mL) were added and the reaction mixture was allowed to shake overnight at room temperature. The mixture was then co-evaporated with toluene and purified by flash column chromatography (ethyl acetate+1% acetic acid) which gave the title compound (2.51 g, 88%) as a yellow oil.

Step c: 3-Oxo-2-oxa-bicyclo[2.2.1]heptane-5-carboxylic acid tert-butyl ester (3c)

Compound 3b (13.9 g, 89 mmol) was dissolved in dichloromethane (200 ml) and then cooled to approximately −10° C. under nitrogen. Isobutylene was bubbled into the solution until the total volume had increased to approximately 250 ml which gave a "clowdy solution". BF$_3$×Et$_2$O (5.6 ml, 44.5 mmol, 0.5 eq.) was added and the reaction mixture was kept at approximately −10° C. under nitrogen. After 10 min, a clear solution was obtained. The reaction was monitored by TLC (EtOAc-Toluene 3:2 acidified with a few drops of acetic acid and hexane-EtOAc 4:1, staining with basic permanganate solution). At 70 min only traces of compound 13 remained and aq. saturated NaHCO$_3$ (200 ml) was added to the reaction mixture, which was then stirred vigorously for 10 min. The organic layer was washed with saturated NaHCO$_3$ (3×200 ml) and brine (1×150 ml), then dried with sodium sulfite, filtered and concentrated into an oil containing small droplets. Upon addition of hexane to the residue the product crashed out. Addition of more hexane and heating to reflux gave a clear solution from which the product crystallized. The crystals were collected by filtration and washed with hexane (rt), then air-dried for 72 h which gave the title compound as colourless needles (12.45 g, 58.7 mmol, 66% from first harvest).

$^1$H-NMR (300 MHz, CD$_3$OD) δ 1.45 (s, 9H), 1.90 (d, J=11.0 Hz, 1H), 2.10-2.19 (m, 3H), 2.76-2.83 (m, 1H), 3.10 (s, 1H), 4.99 (s, 1H); $^{13}$C-NMR (75.5 MHz, CD$_3$OD) δ 27.1, 33.0, 37.7, 40.8, 46.1, 81.1, 81.6, 172.0, 177.7.

Step d: (1R,2R,4S)-2-(((1R,2S)-1-Ethoxycarbonyl-2-vinyl-cyclopropylcarbamoyl)-4-hydroxy-cyclopentanecarboxylic acid ten-butyl ester (3d)

Compound 3c (56 mg, 0.264 mmol) was dissolved in dioxane/water 1:1 (5 mL) and the mixture was cooled to 0° C. 1 M lithium hydroxide (0.52 mL, 0.520 mmol) was added and the mixture was stirred at 0° C. for 45 minutes, after which the mixture was neutralized with 1M hydrochloric acid, evaporated and co-evaporated with toluene. The crystalline residue was dissolved in DMF (5 mL) and (1R,2S)-1-amino-2-vinyl-cyclo-propane carboxylic acid ethyl ester hydrochloride (60 mg, 0.313 mmol) and diisopropylethylamine (DIEA) (138 μl, 0.792 mmol) were added and the solution was cooled to 0° C. HATU (120 mg, 0.316 mmol) was added and the mixture was stirred for 0.5 h at 0° C. and then for an additional 2 h at room temperature. The mixture was then evaporated and extracted with EtOAc, washed with brine, dried, filtered and concentrated. Purification by flash column chromatography (toluene/EtOAc 1:1) provided the title compound (86 mg, 89%) as a colourless oil. The afforded oil was crystallised from ethyl acetate-hexane.

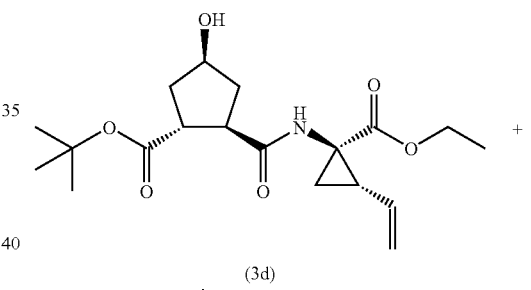

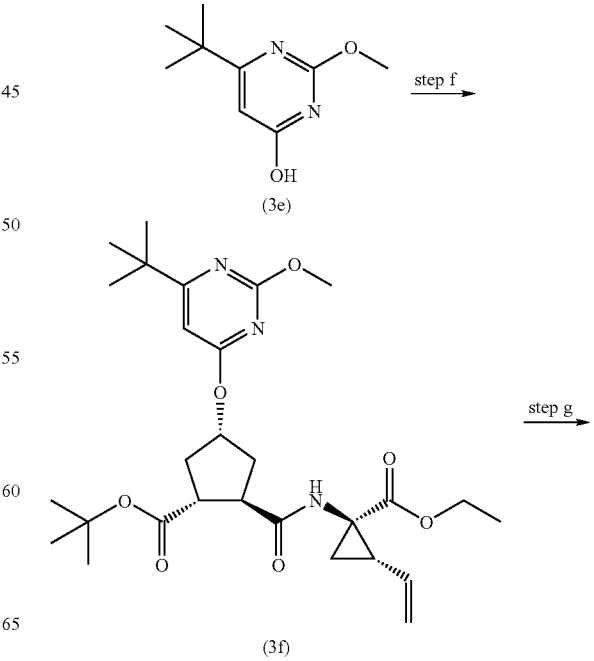

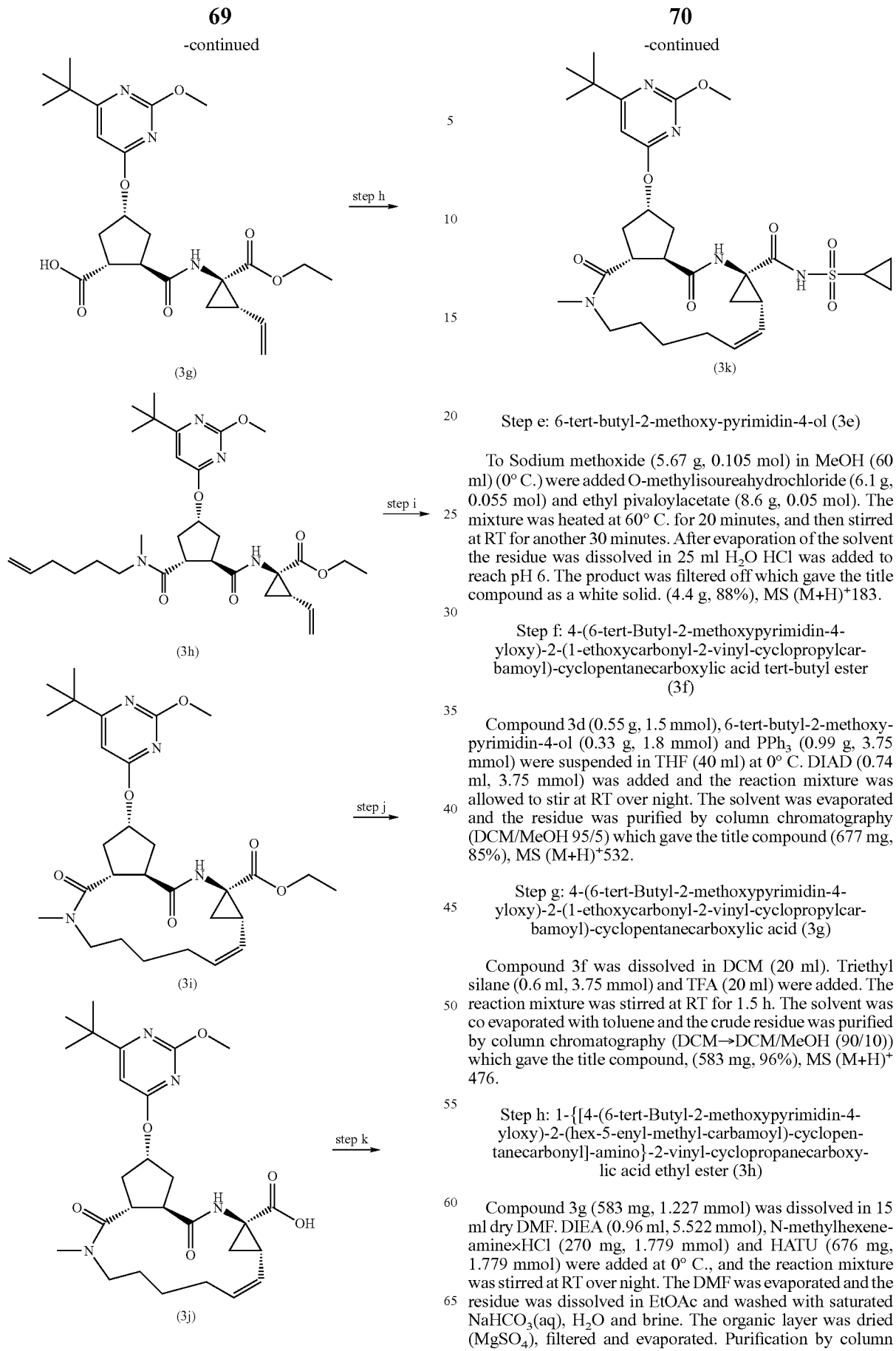

Step e: 6-tert-butyl-2-methoxy-pyrimidin-4-ol (3e)

To Sodium methoxide (5.67 g, 0.105 mol) in MeOH (60 ml) (0° C.) were added O-methylisoureahydrochloride (6.1 g, 0.055 mol) and ethyl pivaloylacetate (8.6 g, 0.05 mol). The mixture was heated at 60° C. for 20 minutes, and then stirred at RT for another 30 minutes. After evaporation of the solvent the residue was dissolved in 25 ml $H_2O$ HCl was added to reach pH 6. The product was filtered off which gave the title compound as a white solid. (4.4 g, 88%), MS (M+H)$^+$183.

Step f: 4-(6-tert-Butyl-2-methoxypyrimidin-4-yloxy)-2-(1-ethoxycarbonyl-2-vinyl-cyclopropylcarbamoyl)-cyclopentanecarboxylic acid tert-butyl ester (3f)

Compound 3d (0.55 g, 1.5 mmol), 6-tert-butyl-2-methoxy-pyrimidin-4-ol (0.33 g, 1.8 mmol) and PPh$_3$ (0.99 g, 3.75 mmol) were suspended in THF (40 ml) at 0° C. DIAD (0.74 ml, 3.75 mmol) was added and the reaction mixture was allowed to stir at RT over night. The solvent was evaporated and the residue was purified by column chromatography (DCM/MeOH 95/5) which gave the title compound (677 mg, 85%), MS (M+H)$^+$532.

Step g: 4-(6-tert-Butyl-2-methoxypyrimidin-4-yloxy)-2-(1-ethoxycarbonyl-2-vinyl-cyclopropylcarbamoyl)-cyclopentanecarboxylic acid (3g)

Compound 3f was dissolved in DCM (20 ml). Triethyl silane (0.6 ml, 3.75 mmol) and TFA (20 ml) were added. The reaction mixture was stirred at RT for 1.5 h. The solvent was co evaporated with toluene and the crude residue was purified by column chromatography (DCM→DCM/MeOH (90/10)) which gave the title compound, (583 mg, 96%), MS (M+H)$^+$ 476.

Step h: 1-{[4-(6-tert-Butyl-2-methoxypyrimidin-4-yloxy)-2-(hex-5-enyl-methyl-carbamoyl)-cyclopentanecarbonyl]-amino}-2-vinyl-cyclopropanecarboxylic acid ethyl ester (3h)

Compound 3g (583 mg, 1.227 mmol) was dissolved in 15 ml dry DMF. DIEA (0.96 ml, 5.522 mmol), N-methylhexene-amine×HCl (270 mg, 1.779 mmol) and HATU (676 mg, 1.779 mmol) were added at 0° C., and the reaction mixture was stirred at RT over night. The DMF was evaporated and the residue was dissolved in EtOAc and washed with saturated NaHCO$_3$(aq), $H_2O$ and brine. The organic layer was dried (MgSO$_4$), filtered and evaporated. Purification by column

Step i: 17-(6-tert-Butyl-2-methoxypyrimidin-4-yloxy)-13-methyl-2,14-dioxo-3,13-diaza-tricyclo[13.3.0.0*4,6*]octadec-7-ene-4-carboxylic acid ethyl ester (3i)

Compound 3h (500 mg, 0.87 mmol) and Hoveyda-Grubbs catalyst, $2^{nd}$ generation (50 mg) were dissolved in degassed and dry DCE (500 ml). The mixture was heated to reflux over night under $N_2$-atmosphere. The material was mixed with silica, the solvent was evaporated and the residue was purified by column chromatography, EtOAc/Heptane 30:70→50:50 which gave the title compound (350 mg, 74%), MS (M+H)$^+$ 543.

Step j: 17-(6-tert-Butyl-2-methoxypyrimidin-4-yloxy)-13-methyl-2,14-dioxo-3,13-diaza-tricyclo[13.3.0.0*4,6*]octadec-7-ene-4-carboxylic acid (3j)

Compound 3i (350 mg, 0.645 mmol) was dissolved in a 2:1:1 mixture of THF:MeOH:$H_2O$ (100 ml). LiOH (1 M, 6.5 ml) was added and the reaction mixture was stirred at 60° C. over night. The mixture was acidified by adding citric acid and then extracted three times with EtOAc. The combined organic layers were dried (MgSO$_4$), filtered and evaporated. The afforded residue was purified by column chromatography (DCM/MeOH 98/2→94/6) which gave the title compound (320 mg, 97%), MS (M+H)$^+$515.

Step k: Cyclopropanesulfonic acid [17-(6-tert-butyl-2-methoxypyrimidin-4-yloxy)-13-methyl-2,14-dioxo-3,13-diaza-tricyclo[13.3.0.0*4,6*]octadec-7-ene-4-carbonyl]amide (3k)

Compound 3j (120 mg, 0.233 mmol) was dissolved in DCM (10 ml). EDAC (54 mg, 0.28 mmol) was added and the reaction mixture was stirred at RT for 2.5 h. Cyclo-propanesulfonic acid amide (31 mg, 0.256 mmol) and DBU (73 µl, 0.489 mmol) were added and the reaction mixture was stirred at RT over night. 5% Citric acid was added and the organic layer was washed with brine, dried, filtered and evaporated. Purifica-tion by preparative HPLC yielded the pure title compound of (65 mg, 45%), MS (M+H)$^+$618.

Example 4

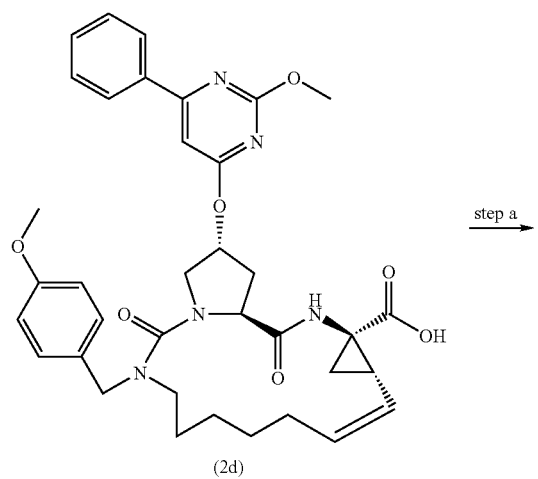

(2d)

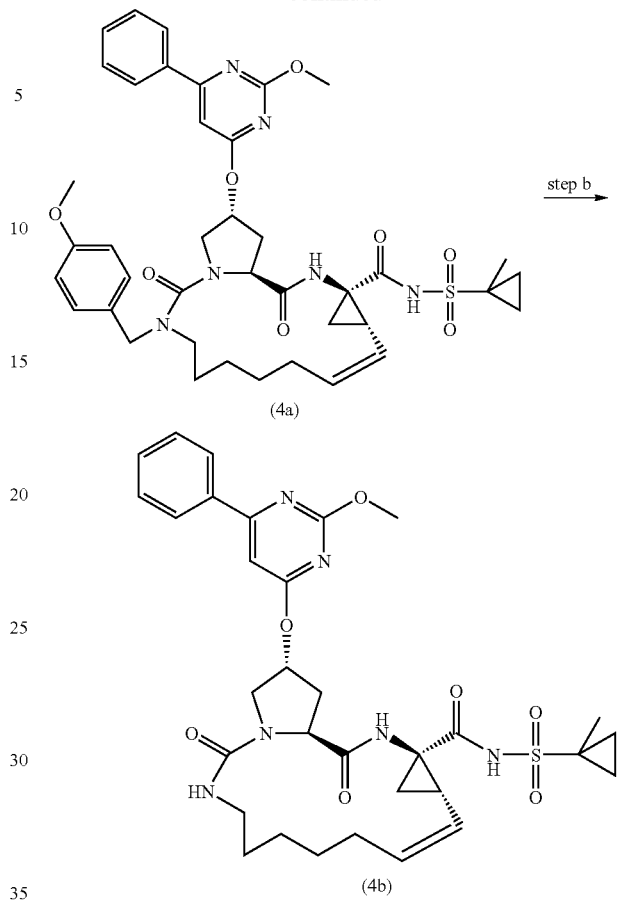

Step a: 1-Methyl-cyclopropanesulfonic acid [14-(4-methoxy-benzyl)-18-(2-methoxy-6-phenyl-pyrimidin-4-yloxy)-2,15-dioxo-3,14,16-triaza-tricyclo[14.3.0.0*4,6*]nonadec-7-ene-4-carbonyl]-amide (4a)

Compound 2d (130 mg, 0.198 mmol) was dissolved in DCM (10 ml). EDAC (46 mg, 0.238 mmol) was added and the reaction mixture was stirred at RT for 2.5 h. Methyl cyclopropanesulfonic amide (30 mg, 0.3218 mmol) and DBU (63 µl, 0.416 mmol) were added and the mixture was stirred at RT over night. 5% Citric acid was added and the organic layer was washed with brine, dried, filtered and evaporated. The material was used directly in the following step without further purification.

Step b: 1-Methyl-cyclopropanesulfonic acid [18-(2-methoxy-6-phenylpyrimidin-4-yloxy)-2,15-dioxo-3,14,16-triaza-tricyclo[14.3.0.0*4,6*]nonadec-7-ene-4-carbonyl]-amide (4b)

Compound 4a was dissolved in a 1:2 mixture of TFA:DCM (12 ml) and stirred at RT for 1 h. NaHCO$_3$ was added and the organic layer was dried, filtered and evaporated. The afforded residue was purified by preparative HPLC which gave the pure title compound (36 mg, 16% over two steps), MS (M+H)$^+$639.

Example 5

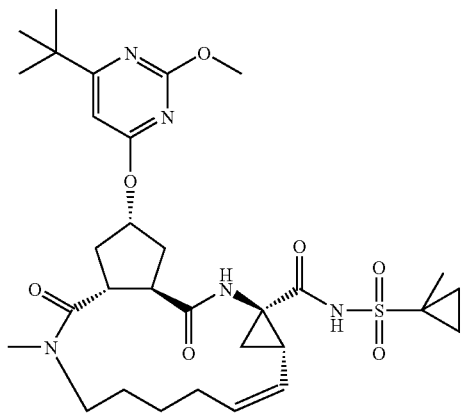

(5)

1-Methyl-cyclopropanesulfonic acid [17-(6-tert-butyl-2-methoxy-pyrimidin-4-yloxy)-13-methyl-2,14-dioxo-3,13-diaza-tricyclo[13.3.0.0*4,6*]octadec-7-ene-4-carbonyl]-amide (5)

Compound 3j (120 mg, 0.233 mmol) was dissolved in DCM (10 ml). EDAC (54 mg, 0.28 mmol) was added and the reaction mixture was stirred at RT for 2.5 h. Methyl cyclopropanesulfonic amide (35 mg, 0.256 mmol) and DBU (73 µl, 0.489 mmol) were added and the reaction mixture was stirred at RT over night. 5% Citric acid was added and the organic layer was separated and washed with brine, dried, filtered and evaporated. The residue was purified by preparative HPLC which gave the pure title compound (10.2 mg, 21%), MS (M+H)$^+$632.

Example 6

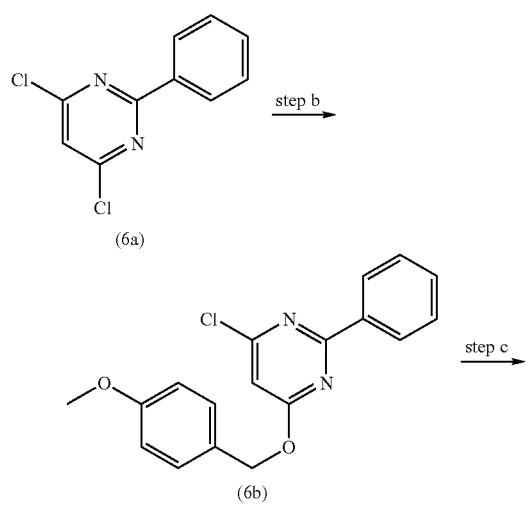

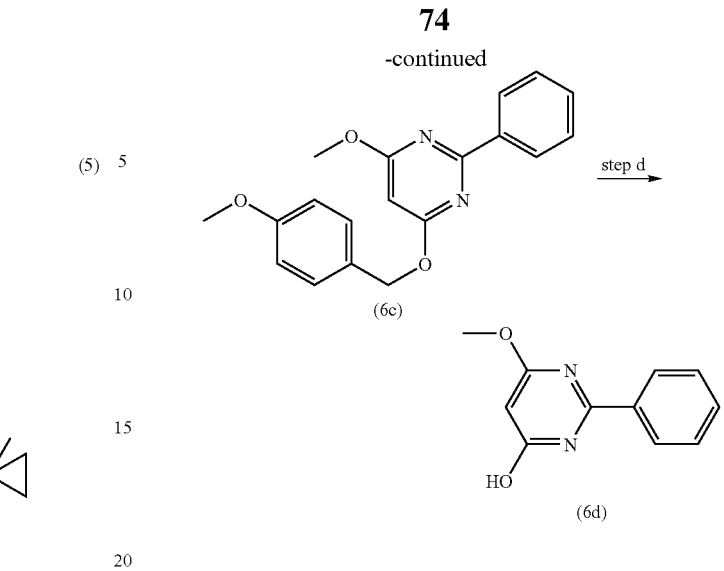

Step a: 4,6-Dichloro-2-phenyl-pyrimidine (6a)

To a mixture of 2-phenylpyrimidine-4,6-diol (7 g, 0.037 mol) in POCl$_3$ (26 ml, 0.279 mol), N,N-diethyl amine was added slowly (11.8 ml, 0.074 mol). The reaction mixture was heated to reflux for 3 h. Some of the POCl$_3$ was evaporated, and the residue was poured on ice followed by extraction with EtOAc. The organic layer was washed with brine, dried (MgSO$_4$), filtered and evaporated to give the title compound (5.16 g, 62%), MS (M+H)$^+$226.

Step b: 4-Chloro-6-(4-methoxybenzyloxy)-2-phenylpyrimidine (6b)

NaH (60%) (469 mg, 11.73 mmol) was added in portions to a stirred solution of 4,6-dichloro-2-phenyl-pyrimidine (2.2 g, 9.78 mmol) and 4-methoxy benzyl alcohol (1.62 mg, 11.73 mmol) in dry THF (55 ml) at 0° C. After 1.5 h, NaHCO$_3$ (aq) was added. Some solvent was evaporated and the residue was extracted with DCM, dried (MgSO$_4$), filtered and evaporated to give the title compound, (3.19 g, 100%), MS (M+H)$^+$327.

Step c: 4-Methoxy-6-(4-methoxy-benzyloxy)-2-phenyl-pyrimidine (6c)

NaOCH$_3$ (2.64 g, 0.049 mol) was dissolved in MeOH (180 ml). 4-Chloro-6-(4-methoxybenzyloxy)-2-phenylpyrimidine (3.19 g, 9.78 mmol) was added and the reaction mixture was stirred at 0° C. for 1 h. The mixture was then heated to reflux temperature for 7 h. The solvent was evaporated and the compound was purified by column chromatography (Heptane→Heptane/EtOAc 9/1) to give the title compound, (2 g, 64%), MS (M+H)$^+$323.

Step d: 6-Methoxy-2-phenylpyrimidin-4-ol (6d)

4-Methoxy-6-(4-methoxybenzyloxy)-2-phenylpyrimidine was dissolved in a mixture of TFA:DCM (1:2, 30 ml). The mixture was stirred at RT for 2 h. NaHCO$_3$ and DCM was added and the organic layer was separated off, dried, filtered and evaporated to give the title compound (1.04 g, 83%), MS (M+H)$^+$203.

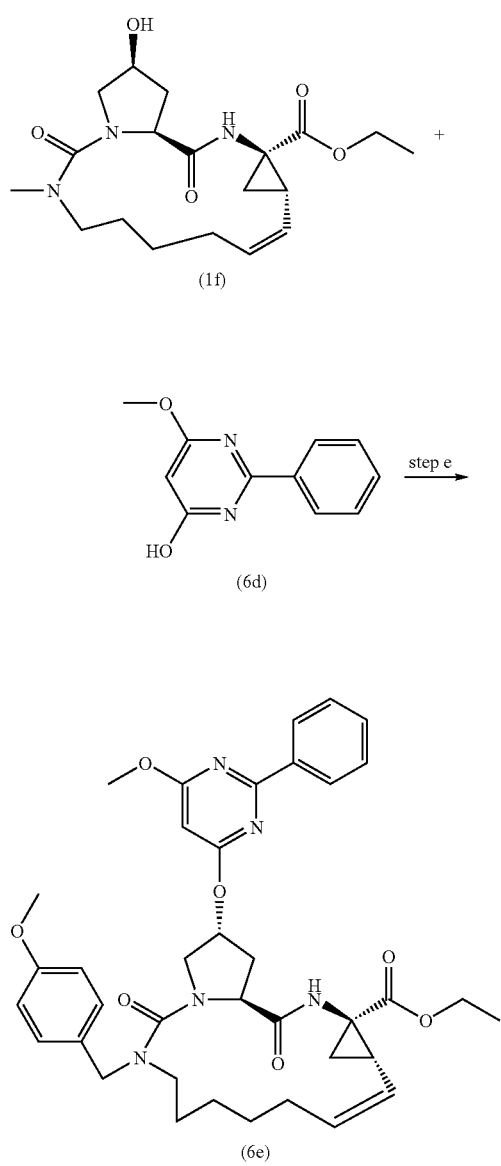

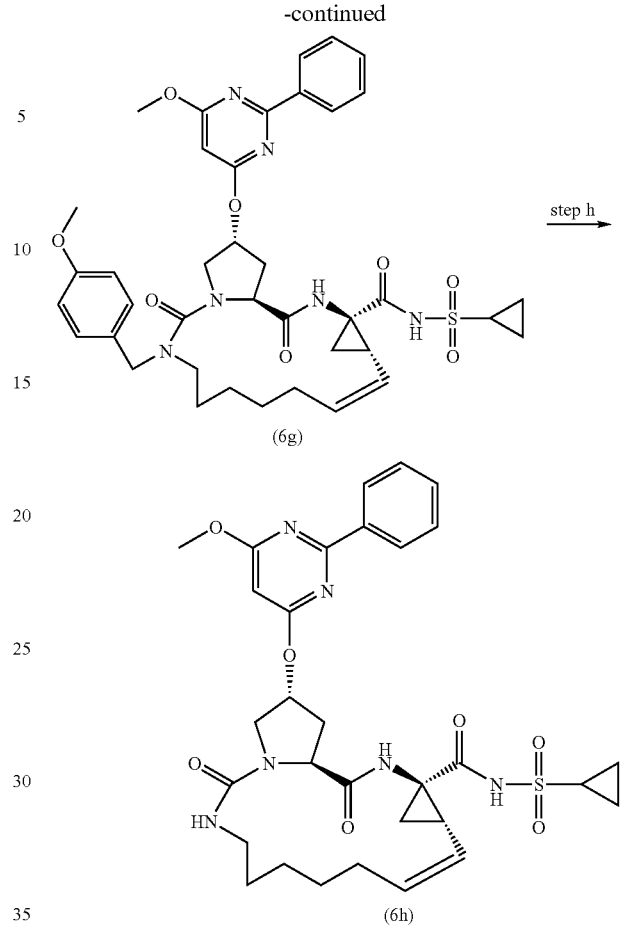

Step e: 14-(4-Methoxy-benzyl)-18-(6-methoxy-2-phenyl-pyrimidin-4-yloxy)-2,15-dioxo-3,14,16-triaza-tricyclo[14.3.0.0*4,6*]nonadec-7-ene-4-carboxylic acid ethyl ester (6e)

Compound 1f (500 mg, 1 mmol), 6-methoxy-2-phenylpyrimidin-4-ol (243 mg, 1.2 mmol), PPh$_3$ (656 mg, 2.5 mmol) and DIAD (0.49 ml, 2.5 mmol) were dissolved in THF (40 ml) and DMF (3 ml). The reaction mixture was allowed to stir at RT over night. The solvent was evaporated, ether was added and PPh$_3$O was filtered off. Purification by column chromatography, toluene/EtOAc 9:1, gave the title compound (410 mg, 60%), MS (M+H)$^+$ 684.

Step f: 14-(4-Methoxybenzyl)-18-(6-methoxy-2-phenylpyrimidin-4-yloxy)-2,15-dioxo-3,14,16-triaza-tricyclo[14.3.0.0*4,6*]nonadec-7-ene-4-carboxylic acid (6f)

Compound 6e (410 mg, 0.60 mmol) was dissolved in a 2:1:1 mixture of THF:MeOH:H$_2$O (144 ml). LiOH (1 M, 6 ml) was added and the reaction mixture was stirred at RT over night. 5% Citric acid was added followed by DCM. The organic layer was dried (MgSO$_4$), filtered and evaporated which gave the title compound (305 mg, 78%), MS (M+H)$^+$ 656.

Step g: Cyclopropanesulfonic acid [14-(4-methoxy-benzyl)-18-(6-methoxy-2-phenyl-pyrimidin-4-yloxy)-2,15-dioxo-3,14,16-triaza-tricyclo[14.3.0.0*4,6*]nonadec-7-ene-4-carbonyl]amide (6g)

Compound 6f (250 mg, 0.38 mmol) was dissolved in DCM (10 ml). EDAC (88 mg, 0.46 mmol) was added and the reaction mixture was stirred at RT over night. Cyclopropanelsulfonic amide (51 mg, 0.42 mmol) and DBU (120 μl, 0.80 mmol) were added and stirred at RT for 2 h. Citric acid was added, followed by separation of the organic layer, which was washed with brine, dried, filtered and evaporated. This material was used directly in the following step without further purification.

Step h: Cyclopropanesulfonic acid [18-(6-methoxy-2-phenylpyrimidin-4-yloxy)-2,15-dioxo-3,14,16-triaza-tricyclo[14.3.0.0*4,6*]nonadec-7-ene-4-carbonyl]-amide (6h)

Compound 6g was dissolved in a 1:2 mixture of TFA:DCM (24 ml) and stirred at RT for 1 h. NaHCO$_3$ was added and the organic layer was separated of, dried, filtered and evaporated. The residue was purified by preparative HPLC which gave the pure title compound (19 mg, 8% over two steps), MS (M+H)$^+$ 639.

Example 7

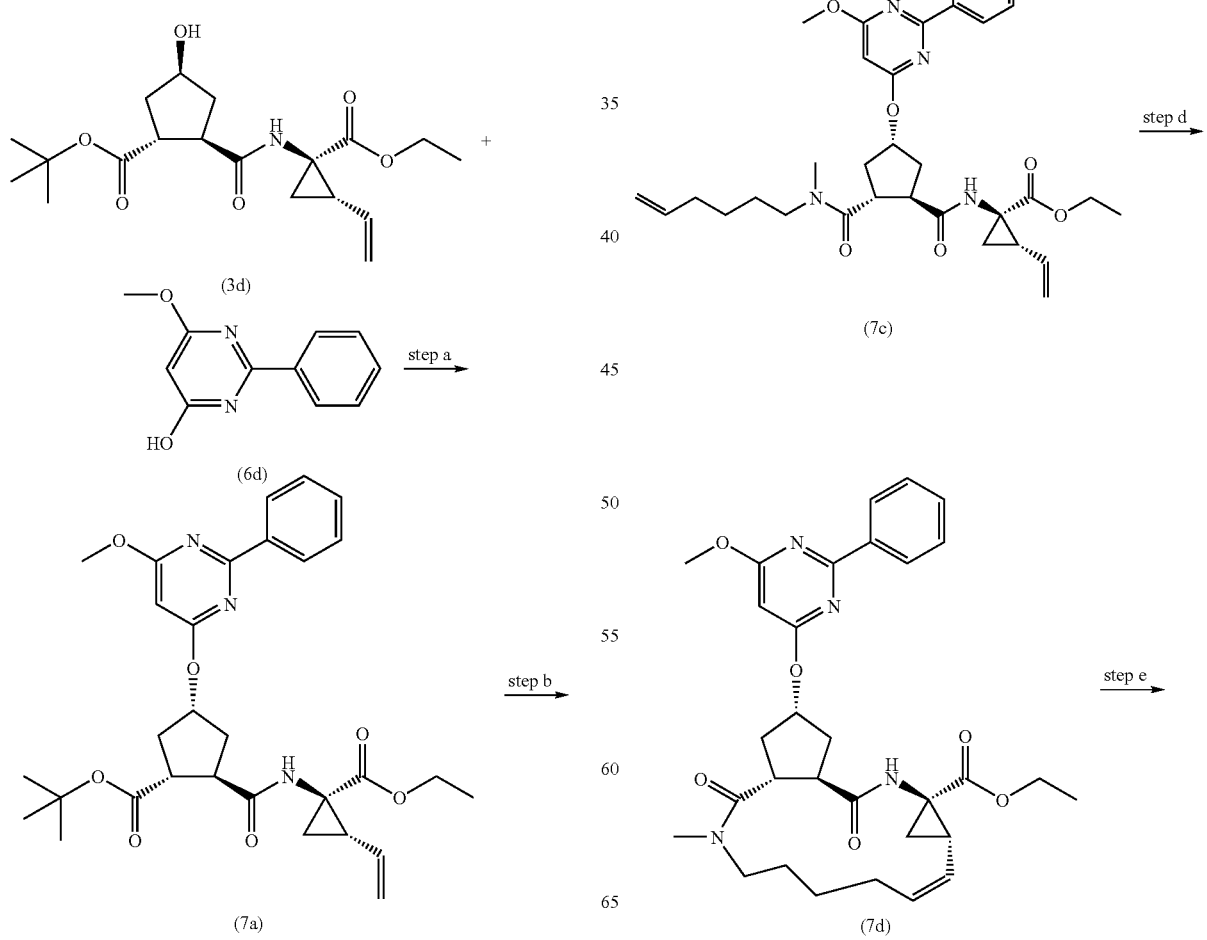

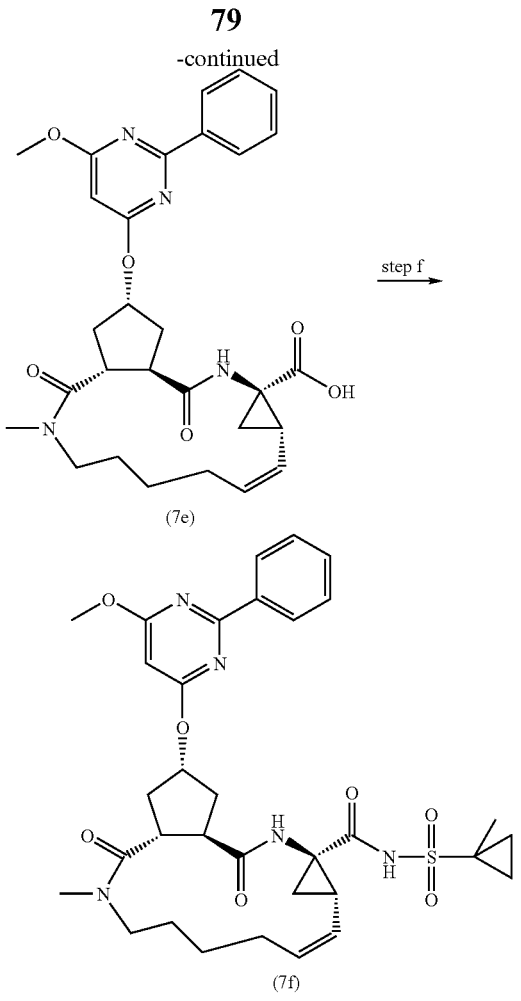

Step a: 2-(1-Ethoxycarbonyl-2-vinyl-cyclopropylcarbamoyl)-4-(6-methoxy-2-phenyl-pyrimidin-4-yloxy)-cyclopentanecarboxylic acid tert-butyl ester (7a)

Compound 6d (730 mg, 3.5 mmol), compound 3d (1.1 g, 3 mmol) and PPh$_3$ (1.97 g, 7.5 mmol) were suspended in THF (80 ml) and the flask was placed on an ice bath. DIAD (1.5 ml, 7.5 mmol) was added and the reaction mixture was stirred at RT over night. The solvent was evaporated, and the residue was dissolved in ether. PPh$_3$O was filtered off and further purification by column chromatography (Heptane/EtOAc, 4/1) gave the title compound (1.47 g, 89%), MS (M+H)$^+$552.

Step b: 2-(1-Ethoxycarbonyl-2-vinyl-cyclopropylcarbamoyl)-4-(6-methoxy-2-phenyl-pyrimidin-4-yloxy)-cyclopentanecarboxylic acid (7b)

Compound 7a (1.48 g, 2.68 mmol) was dissolved in 35 ml DCM. Triethylsilane (1.07 ml, 6.7 mmol) and 35 ml TFA were added and the mixture was stirred at RT for 45 minutes. The solvent was evaporated and co evaporated with toluene which gave the title product (1.32 g, 99%), MS (M+H)$^+$496.

Step c: 1-{[2-(Hex-5-enyl-methyl-carbamoyl)-4-(6-methoxy-2-phenylpyrimidin-4-yloxy)cyclopentanecarbonyl]-amino}-2-vinyl-cyclopropanecarboxylic acid ethyl ester (7c)

Compound 7b (1.32 g, 2.67 mmol) was dissolved in 30 ml dry DMF. DIEA (2.1 ml, 12.0 mmol), N-methylhexeneamine HCl (440 mg, 3.9 mmol) and HATU (1.48 g, 3.9 mmol) were added at 0° C., and the reaction mixture was stirred at RT over night. The DMF was evaporated and the residue was dissolved in EtOAc, washed with sat. NaHCO$_3$(aq), H$_2$O and brine. The organic layer was dried (MgSO$_4$), filtered and evaporated, followed by column chromatography (Heptane/EtOAc), giving the title compound. (1.1 g, 70%), MS (M+H)$^+$ 591.

Step d: 17-(6-Methoxy-2-phenylpyrimidin-4-yloxy)-13-methyl-2,14-dioxo-3,13-diaza tricyclo [13.3.0.0*4,6*]octadec-7-ene-4-carboxylic acid ethyl ester (7d)

Compound 7c (1 g, 1.69 mmol) and Hoveyda-Grubbs catalyst, 2$^{nd}$ generation (100 mg) were dissolved in degassed and dry DCE (1000 ml). The mixture was heated to reflux temperature over night under N$_2$-atmosphere. The material was mixed with silica and the solvent was evaporated. Purification by column chromatography, EtOAc/Heptane 30:70→50:50 gave the title compound (362 mg, 38%), MS (M+H)$^+$563.

Step e: 17-(6-Methoxy-2-phenylpyrimidin-4-yloxy)-13-methyl-2,14-dioxo-3,13-diaza-tricyclo [13.3.0.0*4,6*]octadec-7-ene-4-carboxylic acid (7e)

Compound 7d (362 mg, 0.644 mmol) was dissolved in a 2:1:1 mixture of THF:MeOH:H$_2$O (100 ml). LiOH (1 M, 6.5 ml) was added and the reaction mixture was stirred at 60° C. for 72 h. The reaction mixture was acidified by addition of 5% citric acid whereafter DCM was added. The organic layer was separated, dried (MgSO$_4$), filtered and evaporated which gave the title compound (344 mg, 100%), MS (M+H)$^+$535.

Step f: 1-Methyl-cyclopropanesulfonic acid [17-(6-methoxy-2-phenylpyrimidin-4-yloxy)-13-methyl-2,14-dioxo-3,13-diaza-tricyclo[13.3.0.0*4,6*]octadec-7-ene-4-carbonyl]-amide (7f)

Compound 7e (100 mg, 0.187 mmol) was dissolved in DCM (5 ml), and EDAC (43 mg, 0.224 mmol) was added. The reaction mixture was stirred at RT for 1 h. Methylcyclopropanesulfonic amide (28 mg, 0.206 mmol) and DBU (59 μl, 0.393 mmol) were added and the reaction mixture was stirred at RT over night. Citric acid was added and the organic layer was separated, washed with brine, dried, filtered and evaporated. Purification of the residue by preparative HPLC provided the pure title compound (110 mg, 90%), MS (M+H)$^+$ 652.

Example 8

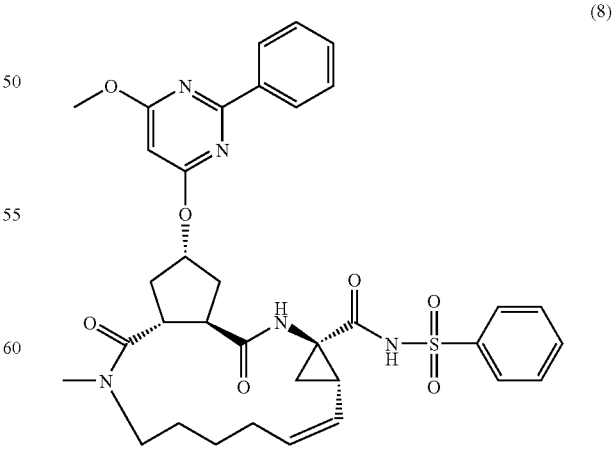

(8)

N-[17-(6-Methoxy-2-phenylpyrimidin-4-yloxy)-13-methyl-2,14-dioxo-3,13-diaza-tricyclo[13.3.0.0*4,6*]octadec-7-ene-4-carbonyl]-benzenesulfonamide (8)

Compound 7e (60 mg, 0.112 mmol) was dissolved in DCM (5 ml). EDAC (26 mg, 0.135 mmol) was added and the reaction mixture was stirred at RT over night. benzensulfonamide (19 mg, 0.123 mmol) and DBU (35 µl, 0.235 mmol) were added and the reaction mixture was stirred at RT for 2 h. Citric acid (5%) was added, the organic layer was separated, washed with brine, dried, filtered and evaporated. The residue was purified by preparative HPLC which gave the pure title compound. (36 mg, 48%), MS (M+H)+674.

Example 9

(9)

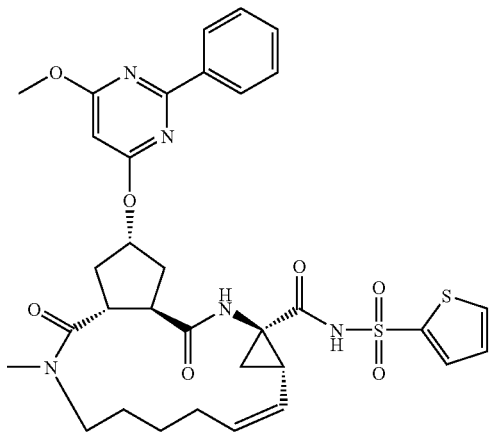

Thiophene-2-sulfonic acid [17-(6-methoxy-2-phenylpyrimidin-4-yloxy)-13-methyl-2,14-dioxo-3,13-diaza-tricyclo[13.3.0.0*4,6*]octadec-7-ene-4-carbonyl]-amide (9)

Compound 7e (27 mg, 0.05 mmol) was dissolved in DCM (3 ml). EDAC (12 mg, 0.06 mmol) was added and the reaction mixture was stirred at RT for 1 h. thiofen-2-sulfonic amide (9 mg, 0.055 mmol) and DBU (16 µl, 0.105 mmol) were added and the reaction mixture was stirred at RT for 2 h. Citric acid (5%) was added, the organic layer was separated, washed with brine, dried, filtered and evaporated. The residue was purified by preparative HPLC which gave the pure title compound. (30 mg, 88%), MS (M+H)+680.

Example 10

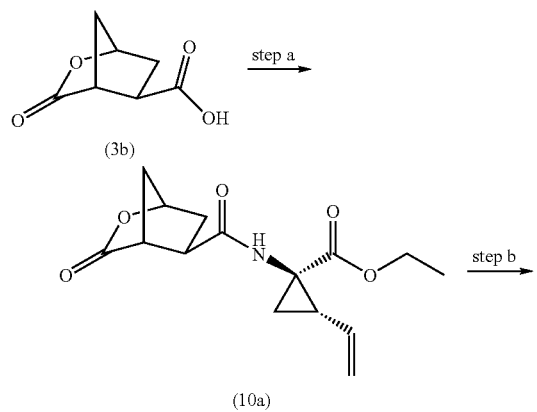

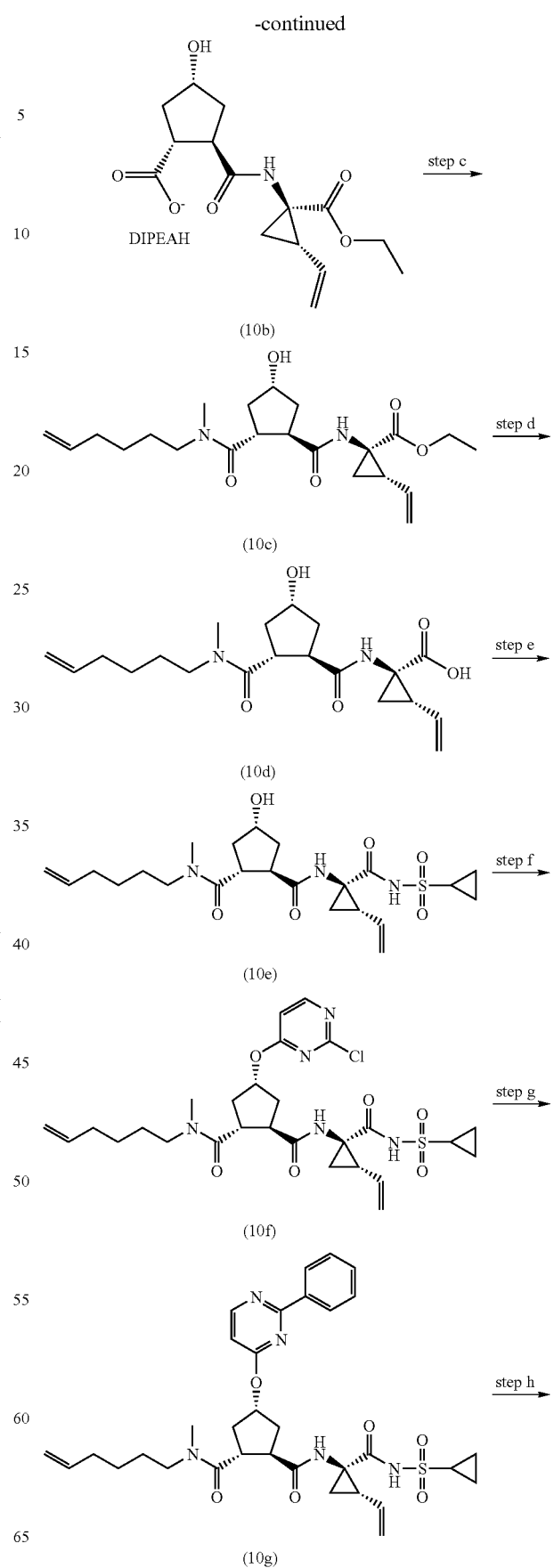

-continued

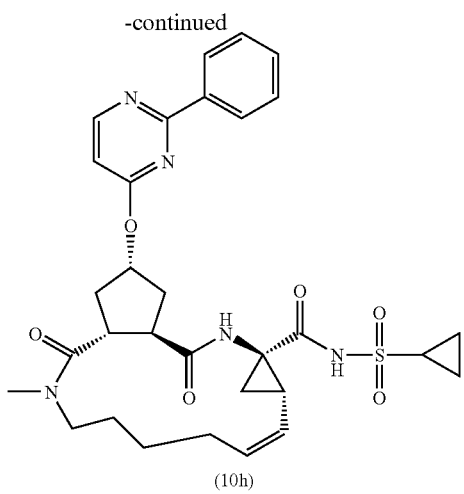

(10h)

Step a: 1-[(3-oxo-2-oxa-bicyclo[2.2.1]heptane-5-carbonyl)-amino]-2-vinyl-cyclopropane carboxylic acid ethyl ester (10a)

To a solution of compound 3b (857 mg, 5.5 mmol), in DMF (14 mL) and DCM (25 mL) at room temperature, was added the hydrochloride of 1-amino-2-vinyl-cyclopropanecarboxylic acid ethyl ester, prepared as described in WO03/099274, (1.15 g, 6.0 mmol), HATU (2.29 g, 6.0 mmol) and DIPEA (3.82 mL, 22 mmol). The reaction was stirred under $N_2$-atmosphere at ambient temperature for 1 h. LC/MS analysis showed complete conversion and the reaction mixture was concentrated in vacuo. The residue was redissolved in DCM (100 ml) and 0.1 M HCl (aq) and the phases were separated. The organic phase was washed with $NaHCO_3$ (aq) and brine, dried ($MgSO_4$) and filtered. Removal of the solvent in vacuo afforded the target compound (1.6 g, 99%). LC/MS >95%, m/z (ESI$^+$)=294 (MH$^+$)

Step b: 2-(1-Ethoxycarbonyl-2-vinyl-cyclopropylcarbamoyl)-4-hydroxy-cyclopentane carboxylic acid diisopropylethylamine salt (10b)

To a solution of compound 10a (800 mg, 2.73 mmol) in water (15 ml) in a 20 ml microwave reaction vessel was added DIPEA (1.2 ml, 6.8 mmol) and a magnetic stirrbar. The reaction vessel was sealed and the immiscible slurry was shaken vigorously before insertion in the microwave cavity. After 1 min of pre-stirring, the reaction was irradiated for 40 min to a set temperature of 100° C. After cooling to 40° C., the transparent solution was concentrated in vacuo, and the residual brown oil co-evaporated 3× with MeCN to remove any residual water. The crude title compound, in the form of a DIPEA salt, was immediately taken forward to the next step. LC/MS >95%, m/z (ESI$^+$)=312 (MH$^+$).

Step c: 1-{[2-(Hex-5-enyl-methyl-carbamoyl)-4-hydroxy-cyclopentanecarbonyl]-amino}-2-vinyl-cyclopropane carboxylic acid ethyl ester (10e)

The crude compound 10b (5.5 mol) was dissolved in DCM (50 mL) and DMF (14 mL) followed by addition of HATU (2.09 g, 5.5 mmol), N-methyl-N-hex-5-enylamin (678 mg, 6.0 mmol) and DIPEA (3.08 mL, 17.5 mmol) at room temperature. The reaction was stirred at ambient temperature for 1 h. LC/MS analysis showed complete conversion of the starting materials and the reaction mixture was concentrated in vacuo. The residue was redissolved in EtOAc (100 mL) and the organic phase washed with 0.1 M HCl (aq), $K_2CO_3$ (aq) and brine, dried ($MgSO_4$) and filtered. Removal of the solvent in vacuo gave an oil which was purified by flash chromatography (Silica, EtOAc:MeOH) to afford the title compound (1.65 g, 74%). TLC (Silica): MeOH:EtOAc 5:95, $R_f$=0.5; LC/MS >95%, m/z (ESI$^+$)=407 (MH$^+$).

Step d: 1-{[2-(Hex-5-enyl-methyl-carbamoyl)-4-hydroxy-cyclopentanecarbonyl]-amino}-2-vinyl-cyclopropanecarboxylic acid (10d)

Compound 10c (493 mg, 1.21 mmol) was dissolved in DMF (1 mL) and transferred to a 20 mL microwave reaction vessel equipped with a magnetic stirring bar and aqueous LiOH (2 M, 10.5 mL) was added. The reaction vessel was sealed and the immiscible slurry was shaken vigorously before insertion in the microwave cavity. The reaction was irradiated for 30 min to 130° C. The reaction mixture was cooled to 40° C. and the clear solution was acidified to pH 2 with aqueous HCl (1 M, 24 ml) and extracted with EtOAc (3×20 ml). The pooled org phases were washed with brine, dried ($MgSO_4$) and filtered. The solvent was removed in vacuo to afford the title compound (410 mg, 90%). LC/MS >95%, m/z (ESI$^+$)=379 (MH$^+$).

Step e: N-(1-Cyclopropanesulfonylaminocarbonyl-2-vinyl-cyclopropyl)-2-(hex-5-enyl-methyl-aminocarbonyl)-4-hydroxy-cyclopentane-carboxamide (10e)

The crude acid 10d (410 mg, 1.09 mmol) was dissolved in DMF (1.5 ml) and DCM (4.5 ml) followed by addition of EDAC (417 mg, 2.18 mmol) at room temperature. The mixture was allowed to incubate with stirring at room temperature. After 10 min, DMAP (133 mg, 1.09 mmol) was added followed by another 20 min incubation at room temperature. Subsequently, a pre-mixed solution of cyclopropanesulfonic acid amide (527 mg, 4.36 mmol) and DBU (663 mg, 4.36 mmol) in DMF (2 ml) and DCM (2 ml) was added followed by heating in the microwave to 100° C. for 30 min. The resulting red solution was concentrated in vacuo and re-dissolved in EtOAc (20 ml). The organic phase was washed with 1 M HCl (aq) (3×10 ml) and brine (10 ml), dried ($MgSO_4$) and filtered. The solvent was evaporated in vacuo to yield the crude sulfonamide which was further purified by chromatography (Silica, EtOAc:MeOH, 97.5:2.5) which gave the title compound (403 mg, 77%); LC/MS >95%, m/z (ESI$^+$)=482 (MH$^+$).

Step f: N-(1-Cyclopropanesulfonylaminocarbonyl-2-vinyl-cyclopropyl)-2-(hex-5-enyl-methyl-aminocarbonyl)-4-(2-chloropyrimidin-4-yloxy)-cyclopentane-carboxamide (10f)

Compound 10e (43 mg, 89.3 mmol) was dissolved in DMF (2 ml) and the solution was cooled to 0° C. and NaH (11 mg, 0.27 mmol) was added. After 0.5 h 2,4-dichloro-pyrimidine was added. The reaction was stirred at 0° C. for 2 h and then quenched by addition of citric acid. The reaction mixture was extracted with DCM (3×10 ml) and the combined organic phases were washed with citric acid, water and brine. The organic phase was dried over $MgSO_4$ and filtered. The solvent was removed in vacuo to yield the crude target compound (43 mg, 81%); LC/MS m/z (ESI$^+$)=595 (MH$^+$).

Step g: N-(1-Cyclopropanesulfonylaminocarbonyl-2-vinyl-cyclopropyl)-2-(hex-5-enyl-methyl-amino-carbonyl)-4-(2-phenylpyrimidin-4-yloxy)-cyclopentane-carboxamide (10 g)

Compound 10f (43 mg, 72.4 mmol), phenylboronic acid (13 mg, 109 μmol) and (PPh₃)₂PdCl₂ (5 mg, 7.2 umol) were mixed in a microwave reaction vial and heated in the microwave at 120° C. for 20 min. The reaction mixture was then quenched by addition of citric acid (20 ml) and extracted 2 times with DCM (10 ml). The combined organic phases were washed with water (2×10 ml) and brine (10 ml), dried over MgSO₄ and filtered. The solvent was removed in vacuo and the crude product was purified by preparative LC-MS which gave the title compound (5.9 mg, 13%), (ESI⁺)=636 (MH⁺).

Step h: Cyclopropanesulfonic acid [13-methyl-2,14-dioxo-17-(2-phenylpyrimidin-4-yloxy)-3,13-diaza-tricyclo[13.3.0.0*4,6*]octadec-7-ene-4-carbonyl]-amide (10h)

Hoveyda Grubbs catalyst (2nd generation) (1.5 mg, 2.3 μmol) was weighed into a dry microwave reaction vial followed by capping of the vial. A degassed solution of compound 10g was added to the vial via a syringe and the reaction mixture was again degassed with N₂. The reaction was microwave heated at 150° C. for 10 min. The solvent was removed in vacuo and the crude product was purified on preparative LC-MS which gave the title compound (0.9 mg, 16%), (ESI⁺)=608 (MH⁺).

Example 11

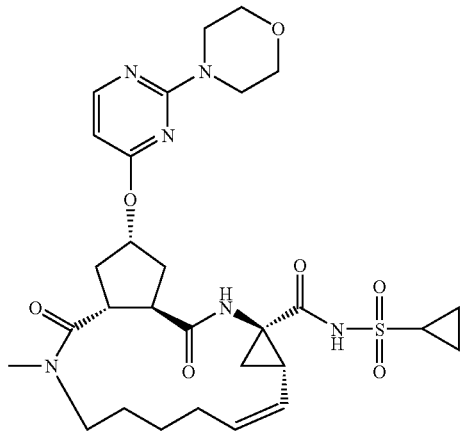

(11)

Cyclopropanesulfonic acid [13-methyl-17-(2-morpholin-4-yl-pyrimidin-4-yloxy)-2,14-dioxo-3,13-diaza-tricyclo[13.3.0.0*4,6*]octadec-7-ene-4-carbonyl]-amide (11)

Compound 10f (31 mg, 0.052 mmol) and morpholine (0.1 ml) in THF was left at ambient temperature for 20 hrs, volatiles were stripped of and the residue was dissolved in DCE (15 ml) to which Hoyeda-Grubbs II catalyst (7 mg) was added. The mixture was heated in a microwave oven at 150° C. for 10 min under an atmosphere of nitrogen, then concentrated to dryness and purified by column chromatography on silica gel eluted with DCM-MeOH 2% followed by prep. HPLC-MS-UV to give pure title compound, (4.7 mg), (M+H)⁺616.2.

Example 12

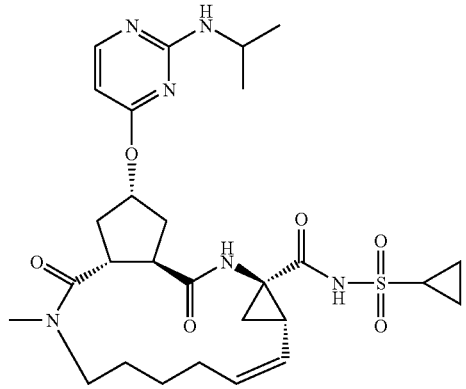

(12)

Cyclopropanesulfonic acid [17-(2-isopropylami-nopyrimidin-4-yloxy)-13-methyl-2,14-dioxo-3,13-diaza-tricyclo[13.3.0.0*4,6*]octadec-7-ene-4-carbonyl]-amide (12)

Compound 10f (30 mg, 0.05 mmol) and isopropylamine (excess) in THF (10 ml) was heated in a microwave oven at 110° C. for 30 min and then left at ambient temperature for 16 hrs. The solvent was stripped of and the residue was redissolved in DCE (15 ml) and degassed with nitrogen. Hoyeda-Grubbs II catalyst (7 mg) was added and the mixture was heated in a microwave oven at 150° C. for 10 min. The mixture was concentrated to dryness and purified by prep. HPLC-MS-UV which gave the pure title compound (3.1 mg), (M+H)⁺=589.2.

Example 13

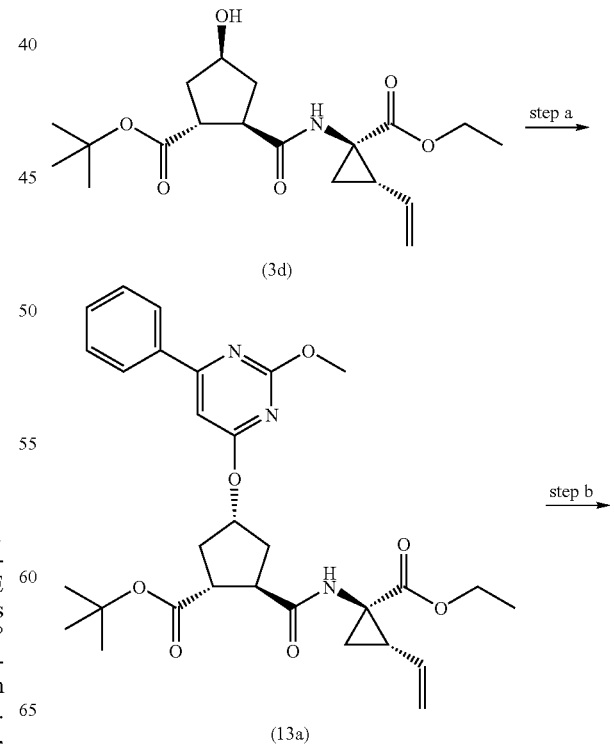

-continued

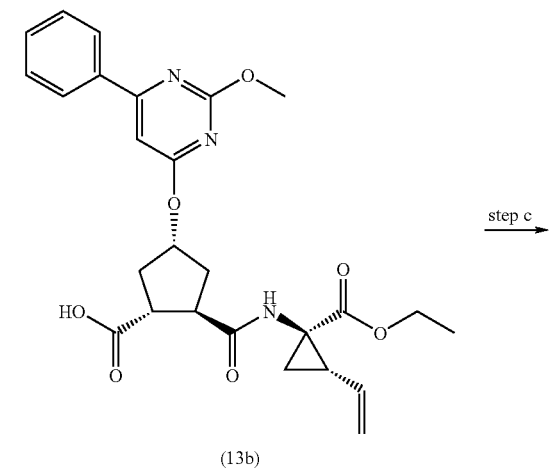

(13b)

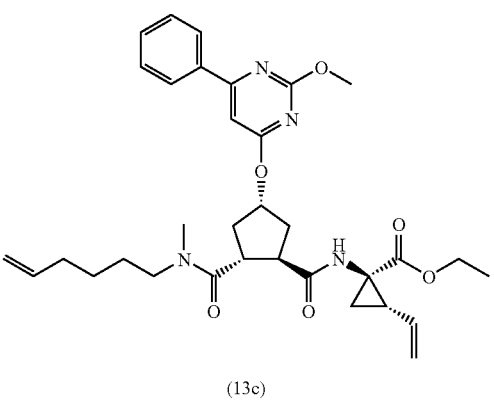

(13c)

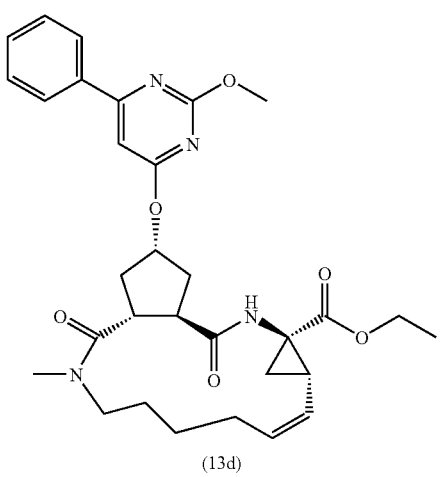

(13d)

-continued

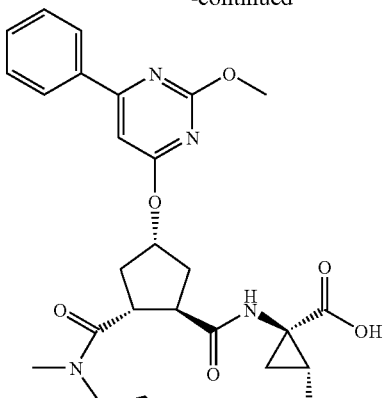

(13e)

step f →

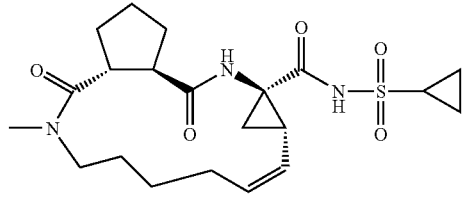

(13f)

Step a: 2-(1-Ethoxycarbonyl-2-vinyl-cyclopropylcarbamoyl)-4-(2-methoxy-6-phenyl-pyrimidin-4-yloxy)-cyclopentanecarboxylic acid tert-butyl ester (13a)

To a cooled suspension of the alcohol 3d (0.74 g, 2 mmol), 2-methoxy-6-phenyl-pyrimidin-4-ol (0.49 g, 2.4 mmol) and triphenylphosphine (1.31 g, 5 mmol) in dry THF (50 ml) was added DIAD (1.0 g, 5 mmol) and the mixture was stirred at room temperature overnight. The mixture was evaporated and the title compound isolated by silica gel chromatography eluted with hexane ethyl acetate, (1.0 g, 90%), (M+H)$^+$552.

Step b: 2-(1-Ethoxycarbonyl-2-vinyl-cyclopropylcarbamoyl)-4-(2-methoxy-6-phenyl-pyrimidin-4-yloxy)-cyclopentanecarboxylic acid (13b)

To a solution of compound 13a (1.0 g, 1.81 mmol) in DCM (30 ml) was added triethylsilane (0.53 g, 4.53 mmol) and TFA (20 ml) and the mixture was stirred at room temperature for 1 hour. The solution was evaporated under reduced pressure and co-evaporated two times with toluene which gave the title compound (1.2 g), (M+H)$^+$496.

Step c: 1-{[2-(Hex-5-enyl-methyl-carbamoyl)-4-(2-methoxy-6-phenyl-pyrimidin-4-yloxy)-cyclopentanecarbonyl]-amino}-2-vinyl-cyclopropanecarboxylic acid ethyl ester (13c)

To a ice cooled solution of the crude acid 13b (1.2 g, 1.81 mmol), N-methylhexeneamine hydrochloride (0.404 g, 2.7 mmol) and DIEA (1.2 g, 9.1 mmol) was added HATU (1.02 g, 2.7 mmol) and the mixture was stirred for twenty minutes on an ice bath and two hours at room temperature. A saturated solution of sodium hydrogen carbonate was added and the mixture was extracted three times with ethyl acetate. The combined organic phases were washed with saturated sodium hydrogen carbonate and brine and dried with sodium sulphate, filtered and evaporated under reduced pressure. The product was isolated by silica gel chromatography with hexane ethyl acetate, (0.8 g, 74%), (M+H)$^+$591.

Step d: 17-(2-Methoxy-6-phenyl-pyrimidin-4-yloxy)-13-methyl-2,14-dioxo-3,13-diaza-tricyclo[13.3.0.0*4,6*]octadec-7-ene-4-carboxylic acid ethyl ester (13d)

To a solution of the diolefin 13c (760 mg, 1.28 mmol) in DCE (700 ml) under argon (three times evaporated three times filled with argon) was added Hoveyda Grubbs catalyst 2nd generation (80 mg) and the mixture was refluxed overnight. The solvent was evaporated under reduced pressure and the residue was purified by silica gel chromatography with hexane ethyl acetate which gave the title compound (0.52 g, 70%), (M+H)$^+$563.

Step e: 17-(2-Methoxy-6-phenylpyrimidin-4-yloxy)-13-methyl-2,14-dioxo-3,13-diaza-tricyclo[13.3.0.0*4,6*]octadec-7-ene-4-carboxylic acid (13e)

To a solution of compound 13d (470 mg, 0.83 mmol) in a mixture of THF methanol 1:1 (30 ml) was added 1 M LiOH solution (10 ml) and the mixture was stirred for four days at room temperature. A 5% solution of citric acid was added and the mixture was extracted three times with ethyl acetate. The organic phase was dried with sodium sulphate and evaporated on silica gel. The product was isolated by silica gel chromatography eluted with DCM methanol, (400 mg, 88%), (M+H)$^+$535.

Step f: Cyclopropanesulfonic acid [17-(2-methoxy-6-phenylpyrimidin-4-yloxy)-13-methyl-2,14-dioxo-3,13-diaza-tricyclo[13.3.0.0*4,6*]octadec-7-ene-4-carbonyl]-amide (13f)

A solution of the acid 13e (150 mg, 0.28 mmol) and EDAC (65 mg, 0.34 mmol) in dry DCM (3 ml) was stirred overnight. Cyclopropane sulphonamide (72.7 mg, 0.6 mmol) and DBU (120 mg, 0.8 mmol) was added and the mixture was stirred overnight at room temperature. 5% Citric acid was added and the mixture was extracted with ethyl acetate. The organic phase was washed two times with 5% citric acid and water, dried with sodium sulphate and evaporated under reduced pressure. Purification by HPLC gave the title compound, (100 mg, 56%), (M+H)$^+$638

Example 14

(14)

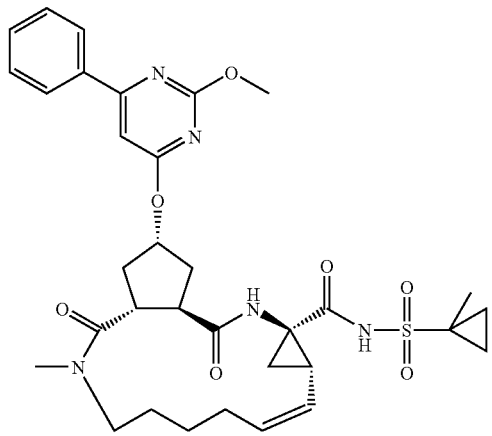

1-Methyl-cyclopropanesulfonic acid [17-(2-methoxy-6-phenyl-pyrimidin-4-yloxy)-13-methyl-2,14-dioxo-3,13-diaza-tricyclo[13.3.0.0*4,6*]octadec-7-ene-4-carbonyl]-amide (14)

A solution of the acid 13e (250 mg, 0.46 mmol) and EDAC (150 mg, 0.6 mmol) in dry DCM (4 ml) was stirred overnight at room temperature. Methylcyclopropane sulphonamide (78 mg, 0.58 mmol) and DBU (182 mg, 1.2 mmol) were added and the mixture was stirred for additional 6 hours at room temperature. 5% Citric acid was added and the mixture was extracted with ethyl acetate. The organic phase was washed two times with 5% citric acid and water, dried with sodium sulphate and evaporated under reduced pressure. Purification by column chromatography on silica gel eluted with diethyl ether-ethyl acetate gave the pure title compound, (130 mg, 44%), (M+H)$^+$652.

Example 15

(15)

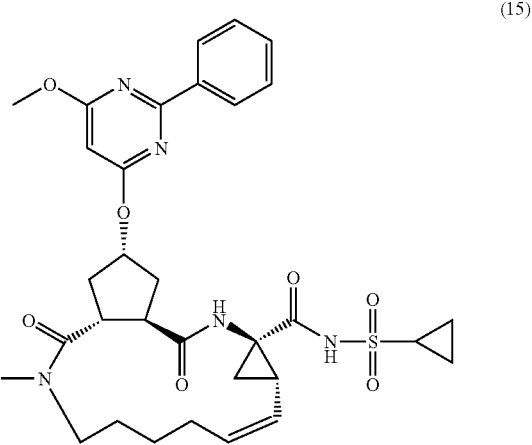 [SMILES: COc1cc(O[C@@H]2C[C@H]3C(=O)N[C@]4(C(=O)NS(=O)(=O)C5CC5)C[C@H]4/C=C\CCCCN(C)C(=O)[C@@H]3C2)nc(-c2ccccc2)n1]

Cyclopropanesulfonic acid [17-(6-methoxy-2-phenylpyrimidin-4-yloxy)-13-methyl-2,14-dioxo-3,13-diaza-tricyclo[13.3.0.0*4,6*]octadec-7-ene-4-carbonyl]-amide (15)

The procedure described in Example 7 step f was followed but using cyclopropane sulfonamide instead of methylcyclopropane sulfoneamide, which gave the title compound, (200 mg, 60%), (M+H)$^+$638.

Example 16

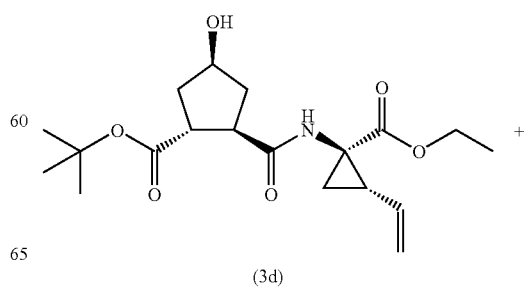

(3d)

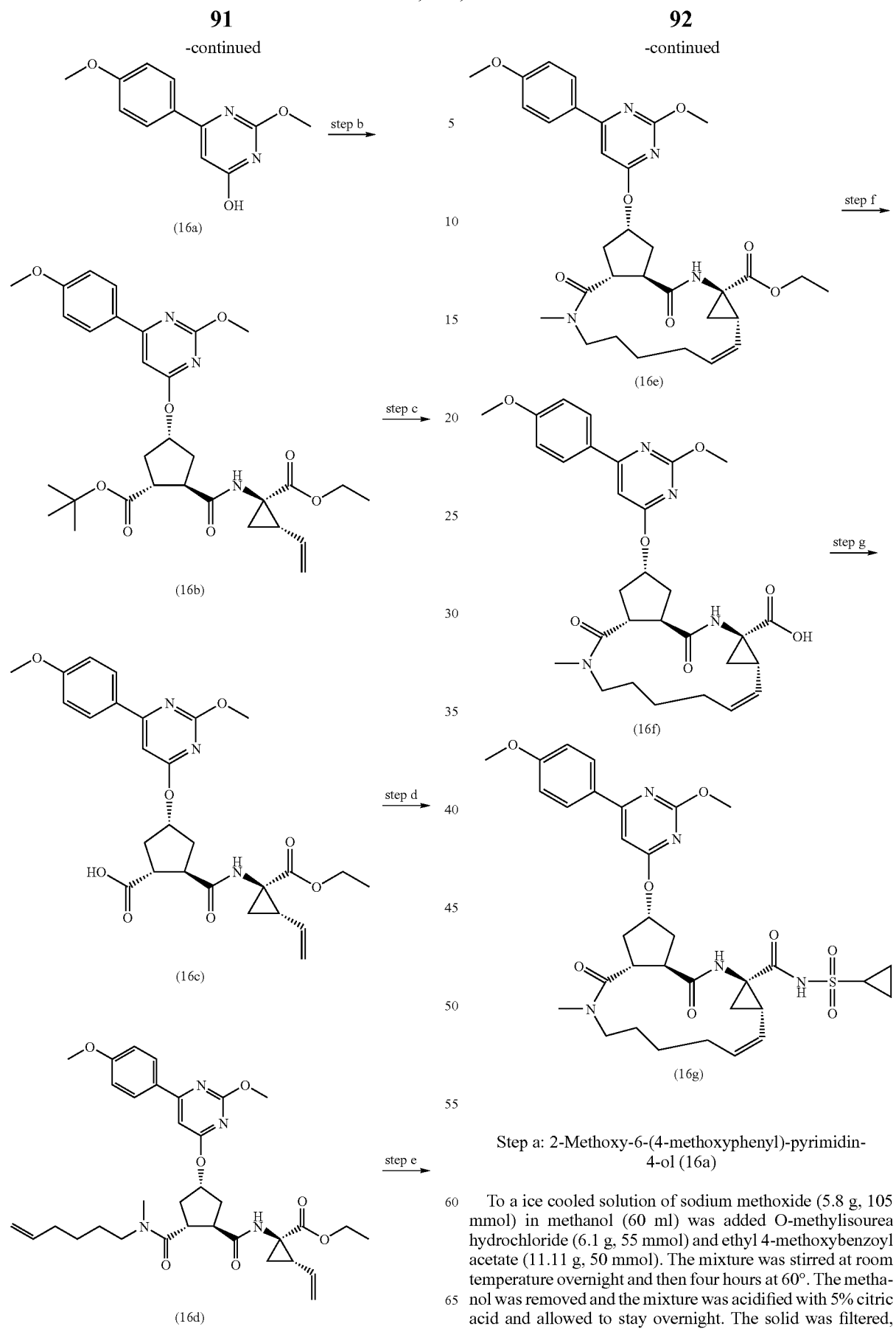

Step a: 2-Methoxy-6-(4-methoxyphenyl)-pyrimidin-4-ol (16a)

To a ice cooled solution of sodium methoxide (5.8 g, 105 mmol) in methanol (60 ml) was added O-methylisourea hydrochloride (6.1 g, 55 mmol) and ethyl 4-methoxybenzoyl acetate (11.11 g, 50 mmol). The mixture was stirred at room temperature overnight and then four hours at 60°. The methanol was removed and the mixture was acidified with 5% citric acid and allowed to stay overnight. The solid was filtered, washed with water and suspended in warm ethanol. The mixture was cooled and the title compound was filtered off and collected as a solid, (2.0 g, 7%), (M+H)+233.

Step b: 2-(1-Ethoxycarbonyl-2-vinyl-cyclopropylcarbamoyl)-4-[2-methoxy-6-(4-methoxyphenyl)-pyrimidin-4-yloxy]-cyclopentanecarboxylic acid tert-butyl ester (16b)

The alcohol 3d (0.74 g, 2 mmol) was reacted with 2-methoxy-6-(4-methoxyphenyl)-pyrimidin-4-ol (0.58 g, 2.5 mmol) in the presence of triphenylphosphine (1.31 g, 5 mmol) and DIAD (1.0 g, 5 mmol) in dry THF (50 ml) according to the procedure described in Example 13 step a. Purification by column chromatography on silica gel eluted with ethyl acetate-hexane gave the title compound (1.12 g, 95%), (M+H)+582.

Step c: 2-(1-Ethoxycarbonyl-2-vinyl-cyclopropylcarbamoyl)-4-[2-methoxy-6-(4-methoxy-phenyl)-pyrimidin-4-yloxy]-cyclopentanecarboxylic acid (16c)

Compound 16b (1.11 g, 1.9 mmol) was treated with triethylsilane (0.55 g, 4.75 mmol) and TFA (30 ml) according to the procedure described in Example 13 step b which gave the crude title compound, (1.3 g), (M+H)+526.

Step d: 1-({2-(Hex-5-enyl-methyl-carbamoyl)-4-[2-methoxy-6-(4-methoxy-phenyl)-pyrimidin-4-yloxy]-cyclopentanecarbonyl}-amino)-2-vinyl-cyclopropanecarboxylic acid ethyl ester (16d)

The acid 16c (1.2 g, 2 mmol) was reacted with N-methylhexeneamine (340 mg, 3.0 mmol) and DIEA (1.29 g, 10.0 mmol) in dry DMF (30 ml) according to the procedure described in Example 13 step c. Purification by column chromatography on silica gel gave the title compound, (1.02 g, 82%), (M+H)+621.

Step e: 17-[2-Methoxy-6-(4-methoxy-phenyl)-pyrimidin-4-yloxy]-13-methyl-2,14-dioxo-3,13-diaza-tricyclo[13.3.0.0*4,6*]octadec-7-ene-4-carboxylic acid ethyl ester (16e)

The diolefin 16d (0.95 g, 1.53 mmol) was reacted with Hoveyda Grubbs 2nd generation catalyst (140 mg) in DCE (900 ml) according to the procedure described in Example 13 step d which gave the crude title compound, (560 mg, 62%), (M+H)+565.

Step f: 17-[2-Methoxy-6-(4-methoxy-phenyl)-pyrimidin-4-yloxy]-13-methyl-2,14-dioxo-3,13-diaza-tricyclo[13.3.0.0*4,6*]octadec-7-ene-4-carboxylic acid (16f)

A solution of the ethyl ester 16e (1.2 g, 2 mmol) in THF/MeOH 1:1 (30 ml) was treated with a 1M solution of LiOH as described in Example 13 step d. Purification by column chromatography on silica gel gave the crude title compound, (400 mg, 77%), (M+H)+565.

Step g: Cyclopropanesulfonic acid {17-[2-methoxy-6-(4-methoxy-phenyl)-pyrimidin-4-yloxy]-13-methyl-2,14-dioxo-3,13-diaza-tricyclo[13.3.0.0*4,6*]octadec-7-ene-4-carbonyl}-amide (16g)

The acid 16f (195 mg, 0.34 mmol) was reacted with cyclopropane sulfonamide (53 mg, 0.44 mmol), EDAC (85 mg, 0.44 mmol) and DBU (137 mg, 0.9 mmol) in dry DCM (3 ml) according to the procedure described in Example 13 step f. Purification by column chromatography on silica gel eluted with diethyl ether-ethyl acetate gave the title compound, (100 mg, 45%), (M+H)+668.

Example 17

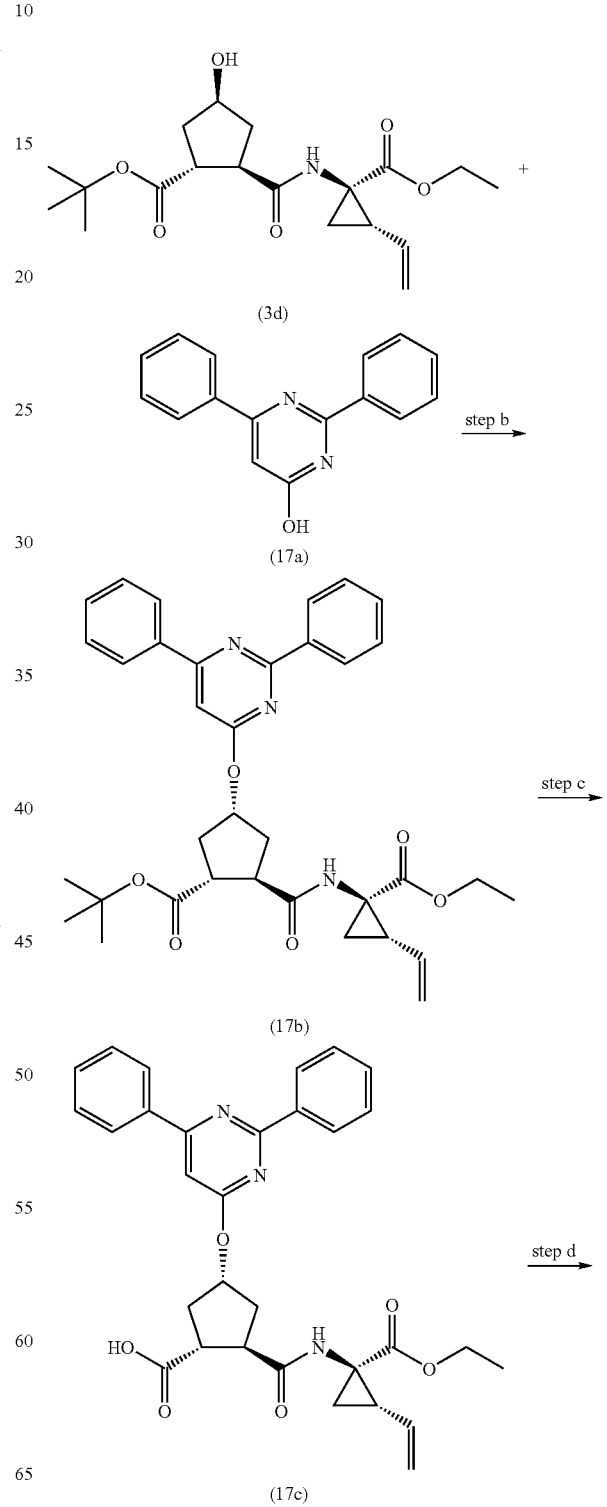

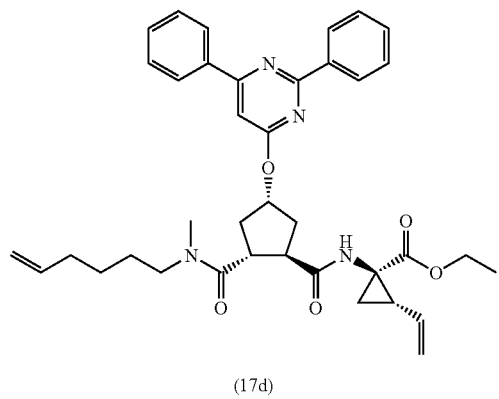

(17d)

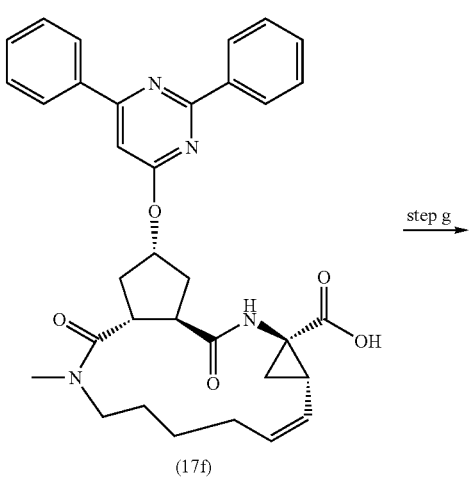

(17e)

(17f)

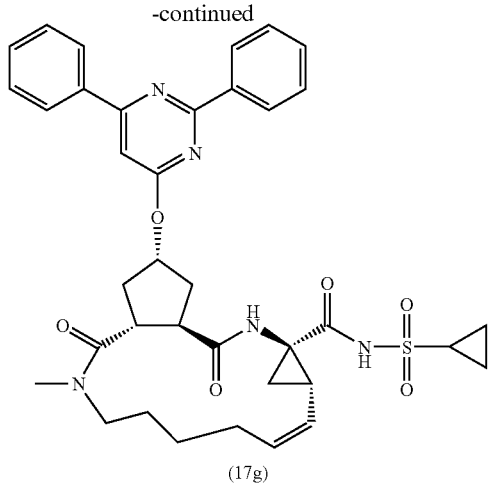

(17g)

Step a: 2,6-Diphenyl-pyrimidin-4-ol (17a)

To a ice cooled solution of sodium hydroxide (2.4 g, 60 mmol) in water (30 ml) was added benzamidine hydrochloride hydrate (9.4 g, 60 mmol) and ethyl benzoylacetate (12.1 g, 63 mmol). Ethanol (ca 30 ml) was added and the mixture was stirred at room temperature overnight. The solid was filtered off, washed with water and diethyl ether and dried which gave the title compound (9.0 g, 60%), $(M+H)^+$1 249.

Step b: 4-(2,6-Diphenyl-pyrimidin-4-yloxy)-2-(1-ethoxycarbonyl-2-vinyl-cyclopropylcarbamoyl)-cyclopentanecarboxylic acid tert-butyl ester (17b)

The alcohol 3d (0.74 g, 2 mmol) was reacted with 2,6-diphenylpyrimidin-4-ol (0.62 g, 2.5 mmol) in the presence of triphenylphosphine (1.31 g, 5 mmol) and DIAD (1.0 g, 5 mmol) in dry THF (50 ml) according to the procedure described in Example 13 step a. Purification by column chromatography on silica gel eluted with ethyl acetate-hexane gave the title compound (1.2 g, 100%), $(M+H)^+$598.

Step c: 4-(2,6-Diphenyl-pyrimidin-4-yloxy)-2-(1-ethoxycarbonyl-2-vinyl-cyclopropylcarbamoyl)-cyclopentanecarboxylic acid (17c)

Compound 17b (1.2 g, 2 mmol) was treated with triethylsilane (0.58 g, 5.0 mmol) and TFA (25 ml) according to the procedure described in Example 13 step b, which gave the crude title compound, (1.2 g), $(M+H)^+$542.

Step d: 1-{[4-(2,6-Diphenyl-pyrimidin-4-yloxy)-2-(hex-5-enyl-methyl-carbamoyl)-cyclopentanecarbonyl]-amino}-2-vinyl-cyclopropanecarboxylic acid ethyl ester (17d)

The acid 17c (1.2 g, 2 mmol) was reacted with N-methyl-hexeneamine (340 mg, 3.0 mmol) DIEA (1.29 g, 10.0 mmol) and HATU (1.1 g, 3 mmol) in dry DMF (30 ml) according to the procedure described in Example 13 step c. Purification by column chromatography on silica gel gave the title compound (1.2 g, 93%), $(M+H)^+$637.

Step e: 17-(2,6-Diphenyl-pyrimidin-4-yloxy)-13-methyl-2,14-dioxo-3,13-diaza-tricyclo[13.3.0.0*4, 6*]octadec-7-ene-4-carboxylic acid ethyl ester (17e)

The diolefin 17d (0.95 g, 1.49 mmol) was reacted with Hoveyda Grubbs $2^{nd}$ generation catalyst (135 mg) in DCE (900 ml) according to the procedure described in Example 13 step d, which gave the title compound, (0.69 g, 76%), (M+H)+ 609.

Step f: 17-(2,6-Diphenyl-pyrimidin-4-yloxy)-13-methyl-2,14-dioxo-3,13-diazatricyclo-[13.3.0.0*4, 6*]octadec-7-ene-4-carboxylic acid (17f)

A solution of the ethyl ester 17e (0.67 g, 1.1 mmol) in THF/MeOH 1:1 (30 ml) was treated with a 1M solution of LiOH (15 ml) as described in Example 13 step d which gave the title compound, (0.49 g, 76%), (M+H)+581.

Step g: Cyclopropanesulfonic acid [17-(2,6-diphenyl-pyrimidin-4-yloxy)-13-methyl-2,14-dioxo-3,13-diaza-tricyclo[13.3.0.0*4,6*]octadec-7-ene-4-carbonyl]-amide (17g)

The acid 17f (240 mg, 0.41 mmol) was reacted with cyclopropane sulfonamide (63 mg, 0.52 mmol), EDAC (105 mg, 0.55 mmol) and DBU (182 mg, 1.2 mmol) in dry DCM according to the procedure described in Example 13 step f. Purification by column chromatography on silica gel eluted with diethyl ether-ethyl acetate gave the title compound, (175 mg, 62%), (M+H)+684.

Example 18

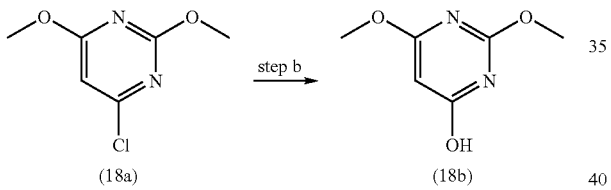

Step a: Synthesis of 4-chloro-2,6-dimethoxypyrimidin (18a)

2.4.6-Trichloropyrimidin (5.5 g, 30 mmol) was added at once to an ice cooled solution of sodium methoxide (3.3 g, 60 mmol) in methanol (120 ml). The mixture was stirred for one hour at about 5° C. and for two hours at room temperature. The solvent was removed under reduced pressure, water was added and the product was extracted three times with ethyl acetate. The combined organic phases were washed with water, dried with sodium sulphate and evaporated which gave the title compound (5.0 g, 95%), purity about 85%

Step b: 2,6-Dimethoxypyrimidin-4-ol (18b)

A suspension of 4-chloro-2,6-dimethoxy-pyrimidine (4.9 g, 28 mmol), DABCO (6.4 g, 57 mmol) and potassium carbonate (13.8 g, 100 mmol) was refluxed in water (150 ml) for one hour. The mixture was cooled acidified with 5% citric acid and extracted three times with ethyl acetate and three times with DCM with about 105 THF and 10% MeOH. The combined organic phases were dried and evaporated which gave the title compound (1.5 g, 34%), (M+H)+1 157.

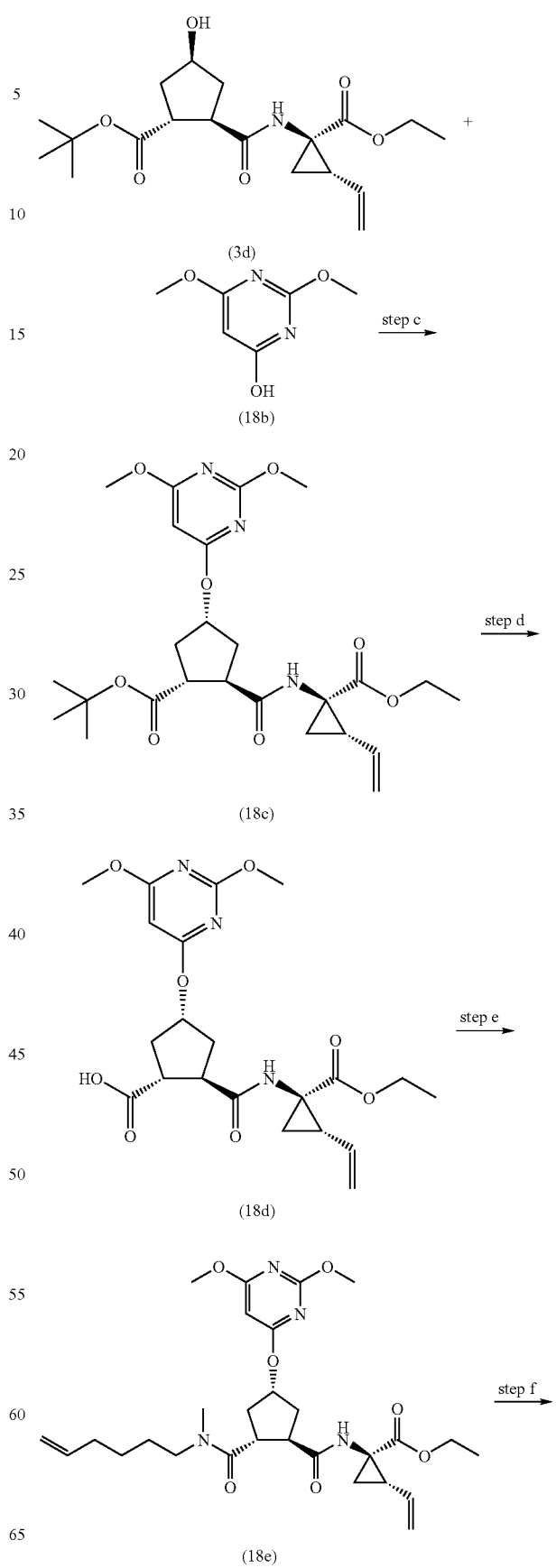

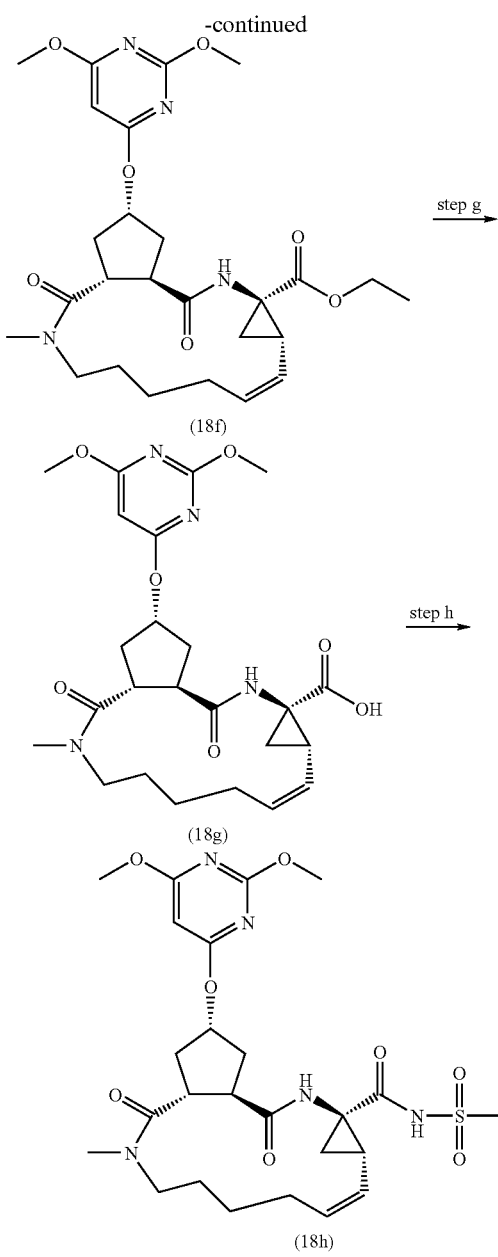

(18f)

(18g)

(18h)

Step c: 4-(2,6-Dimethoxy-pyrimidin-4-yloxy)-2-(1-ethoxycarbonyl-2-vinylcyclo-propylcarbamoyl)-cyclopentanecarboxylic acid tert-butyl ester (18c)

The alcohol 3d (0.74 g, 2 mmol) was reacted with 2,6-dimethoxypyrimidin-4-ol (0.47 g, 3.0 mmol) in the presence of triphenylphosphine (1.31 g, 5 mmol) and DIAD (1.0 g, 5 mmol) in dry THF (50 ml) according to the procedure described in Example 13 step a. Purification by column chromatography on silica gel eluted with ethyl acetate-hexane gave the title compound (0.93 g, 93%), (M+H)$^+$506.

Step d: 4-(2,6-Dimethoxy-pyrimidin-4-yloxy)-2-(1-ethoxycarbonyl-2-vinylcyclo-propylcarbamoyl)-cyclopentanecarboxylic acid (18d)

Compound 18c (0.92 g, 1.83 mmol) was treated with triethylsilane (0.58 g, 5.0 mmol) and TFA (25 ml) in DCM (25 ml) according to the procedure described in Example 13 step b which gave the title compound, (0.83 g), (M+H)$^+$450.

Step e: 1-{[4-(2,6-Dimethoxy-pyrimidin-4-yloxy)-2-(hex-5-enyl-methyl-carbamoyl)-cyclopentanecarbonyl]-amino}-2-vinyl-cyclopropanecarboxylic acid ethyl ester (18e)

The acid 18d (1.2 g, 2 mmol) was reacted with N-methyl-hexeneamine (0.34 g, 3.0 mmol), DIEA (1.29 g, 10.0 mmol) and HATU (1.1 g, 3 mmol) in dry DMF (30 ml) according to the procedure described in Example 13 step c. Purification by column chromatography on silica gel gave the title compound (0.74 g, 74%), (M+H)$^+$545.

Step f: 17-(2,6-Dimethoxy-pyrimidin-4-yloxy)-13-methyl-2,14-dioxo-3,13-diaza-tricyclo[13.3.0.0*4,6*]octadec-7-ene-4-carboxylic acid ethyl ester (18f)

The diolefin 18e (0.73 g, 1.34 mmol) was reacted with Hoveyda Grubbs 2$^{nd}$ generation catalyst (100 mg) in DCE (700 ml) according to the procedure described in Example 13 step d. Purification by column chromatography on silica gel gave the title compound, (0.34 g, 49%), (M+H)$^+$517.

Step g: 17-(2,6-Dimethoxy-pyrimidin-4-yloxy)-13-methyl-2,14-dioxo-3,13-diaza-tricyclo[13.3.0.0*4,6*]octadec-7-ene-4-carboxylic acid (18g)

A solution of the ethyl ester 18f (0.33 g, 0.64 mmol) in THF/MeOH 1:1 (20 ml) was treated with a 1M solution of LiOH (10 ml) as described in Example 13 step d. Purification by column chromatography on silica gel eluted with DCM-MeOH gave the title compound, (0.31 g, 99%), (M+H)$^+$489.

Step h: Cyclopropanesulfonic acid [17-(2,6-dimethoxy-pyrimidin-4-yloxy)-13-methyl-2,14-dioxo-3,13-diaza-tricyclo[13.3.0.0*4,6*]octadec-7-ene-4-carbonyl]-amide (18h)

The acid 18g (1.2 g, 2 mmol) was reacted with cyclopropane sulfonamide (73 mg, 0.6 mmol), EDAC (115 mg, 0.6 mmol) and DBU (215 mg, 1.4 mmol) in dry DCM (3 ml) according to the procedure described in Example 13 step f. Purification by column chromatography on silica gel eluted with diethyl ether-ethyl acetate gave the title compound, (185 mg, 70%), (M+H)$^+$592.

Example 19

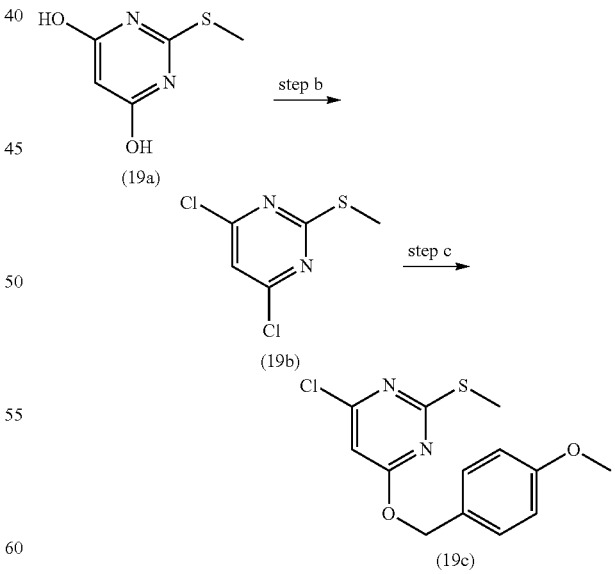

Step a: 2-Methylsulfanyl-pyrimidine-4,6-diol (19a)

Methyl iodide (32.64 g, 220 mmol) was added dropwise to a suspension of thiobarbituric acid (29 g, 200 mmol) in EtOH (300 ml) and 2M NaOH solution in water (110 ml) at room temperature. The mixture was stirred at room temperature overnight and then stirred for two hours at 60° C. The ethanol was removed, water was added and the mixture was allowed to stay for 2 hours on an ice bath. The solid title compound was filtered of, washed with ice cold water and dried (30 g, 95%).

Step b: 4,6-Dichloro-2-methylsulfanyl-pyrimidine (19b)

2-Methylsulfanyl-pyrimidine-4,6-diol (30.0 g, 189 mmol) was added slowly to phosphorus oxychloride (350 ml) while cooling on ice then N,N-diethylaniline (52.5 ml) was added slowly while cooling. The mixture was slowly warmed till reflux and refluxed for 2.5 hours. The mixture was evaporated and added to crushed ice. The mixture was extracted three times with ethyl acetate and the combined organic layers were washed three times with water, once with brine and concentrated. Purification by column chromatography on silica gel eluted with hexane-ethyl acetate gave the title compound (36 g, 97%).

Step c: 4-Chloro-6-(4-methoxy-benzyloxy)-2-methylsulfanyl-pyrimidine (19c)

To a solution of 4-methoxybenzyl alcohol (8.9 g, 65 mmol) in dry DMF (100 ml) was added a 60% suspension of sodium hydride (2.2 g, 55 mmol) in portions and the mixture was stirred for two hours at room temperature. The mixture was cooled in an ice bath and 4,6-dichloro-2-methylsulfanyl-pyrimidine (9.8 g, 50 mmol) in dry THF (20 ml) was added. The mixture was then stirred for 72 h at room temperature. Water was added and the mixture was extracted twice with ethyl acetate. The organic phase was washed with water, dried with sodium sulphate and evaporated under reduce pressure. The residue was purified by silica gel chromatography eluted with hexane ethyl acetate which gave the title compound (9.1 g, 61%), (M+H)$^+$296
$^1$H-NMR CDCl$_3$ δ 2.59 (s, 3H), 3.80 (s, 3H), 5.38 (s, 2H), 6.40 (s, 1H) 6.90 (d, 2H), 7.38 d (d, 2H).

Example 20

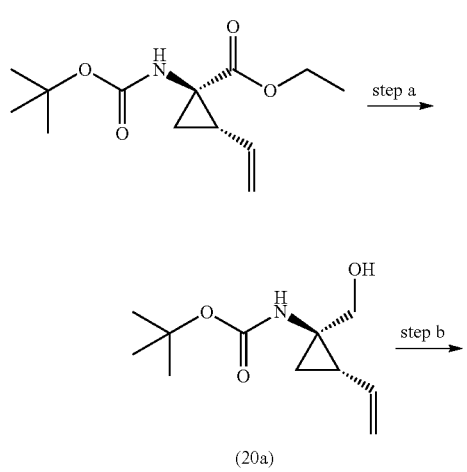

(20a)

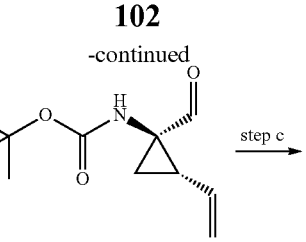

(20b)

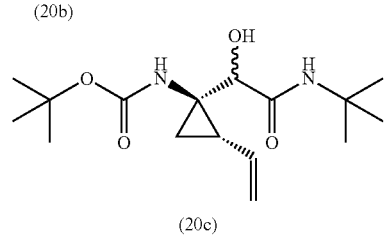

(20c)

Step a: (1-Hydroxymethyl-2-vinylcyclopropyl)-carbamic acid tert-butyl ester (20a)

To a solution of 1-tert-butoxycarbonylamino-2-vinyl-cyclopropanecarboxylic acid ethyl ester (0.51 g, 2.0 mmol) in THF (10 ml) at 0° C. was added a 2M solution of lithiumborohydride (4 ml, 8 mmol). The reaction mixture was monitored by TLC (7:3 hexane-ethyl acetate, stained using ammoniummolybdate-cerium sulfate in aq. 10% sulfuric acid) and after stirring overnight at rt, the reaction was carefully quenched using aq. 10% citric acid (25 ml, dropwise addition at 0° C.). The obtained mixture was washed with dichloromethane (3×10 ml), and the combined organic layers were dried (Na$_2$SO$_4$), filtered and concentrated. Flash chromatography of the residue using 1:1 hexane-ethyl acetate as eluent, followed by concentration of the appropriate fractions and drying the residue in vacuum overnight, gave the product as a colourless syrup (0.407 g, 1.91 mmol, 96%).
NMR data (400 MHz, CDCl$_3$): $^1$H, δ 0.98 (m, 1H), 1.15 (m, 1H), 1.44 (s, 9H), 1.84 (m, 1H), 3.20 (brs, 1H), 3.60 (dd, 1H), 3.78 (brm, 1H), 5.10-5.26 (m, 3H), 5.70 (m, 1H).

Step b: (1-Formyl-2-vinyl-cyclopropyl)-carbamic acid tert-butyl ester (20b)

To a stirred solution of the alcohol 20a (0.152 g, 0.71 mmol) in dichloromethane (5 ml) was added Dess-Martin periodinane (0.33 g, 0.78 mmol) at rt. The reaction was monitored by TLC (3:2 Hexane-ethyl acetate, UV-monitoring and staining using ammoniummolybdate-cerium sulfate in aq. 10% sulfuric acid). Staining indicates a fairly clean reaction, but UV monitoring indicates several byproducts). After 1 h the obtained yellow-red solution was diluted with dichloromethane (20 ml), then washed with 1:1 aq. 10% sodium thiosulfate/aq. saturated sodium hydrogen carbonate (3×20 ml), then dried (Na$_2$SO$_4$), filtered and concentrated. Flash chromatography of the residue using stepwise gradient elution (ethyl acetate in hexane 20-30%) followed by concentration of the appropriate fractions and drying the residue in vacuum overnight, gave the title compound as a colourless oil (0.054 g, 0.255 mmol, 36%).

Step c: [1-(tert-Butylcarbamoyl-hydroxy-methyl)-2-vinyl-cyclopropyl]-carbamic acid tert-butyl ester (20c)

To a solution of the aldehyde 20b (0.054 g, 0.255 mmol) and tert-butylisonitrile (0.043 ml, 0.38 mmol) in dichloromethane (1 ml) and pyridine (0.083 ml, 1.02 mmol) under nitrogen was added trifluoroacetic acid (0.039 ml, 0.51 mmol). After 30 min at rt, the reaction mixture was allowed to reach rt and was stirred for another 2 days. TLC (7:3 hexane-ethyl acetate) and LC-MS monitoring then indicated approx 60% conversion and the reaction mixture was diluted with ethyl acetate (10 ml). The solution was washed successively with aq. 10% citric acid (3×5 ml) and aq. saturated sodium hydrogen carbonate (3×5 ml)), then dried (Na$_2$SO$_4$), filtered and concentrated. The residue was then treated with 1:1:1 aq. 1M LiOH/THF/MeOH (1.5 ml) for 10 min at rt, then diluted with aq. 10% citric acid and taken into ethyl acetate, then dried (Na$_2$SO$_4$), filtered and concentrated. Column chromatography of the residue using 7:3 hexane-ethyl acetate as eluent followed by concentration of the appropriate fractions and drying the residue in vacuum overnight, gave the product as a colourless solid (0.027 g, 0.086 mmol, 34%).

NMR (400 MHz, CDCl$_3$): $^1$H, δ 1.24 (m, 1H), 1.33-1.40 (m, 10H), 1.44 (s, 9H), 1.87 (m, 1H), 3.65 (d, 1H), 5.21 (m, 3H), 5.50 (d, 1H), 5.89 (m, 1H), 7.03 (brs, 1H). α-Hydroxyamide derivatives of the inhibitors of the invention are then achieved by removing the N-boc group from the title compound followed by coupling of the afforded amine to an acid, such as the acid 1i, according to the procedure described in Example 1 step j.

General Procedure for Oxidizing α-Hydroxyamides into α-Ketoamides:

Typically the α-hydroxyamide is dissolved in dichloromethane (20-30 ml/g) at rt, then Dess-Martin Periodinane (1.1 equivalents) is added and the reaction mixture is monitored by TLC and LC-MS. After or near completion of the reaction the reaction mixture is diluted with dichloromethane and then washed with 1:1 aq. 10% sodium thiosulphate/aq. saturated sodium hydrogen carbonate (3 times), then dried (Na$_2$SO$_4$), filtered and concentrated. The residue is purified by column chromatography or preparative-LC.

Example 21

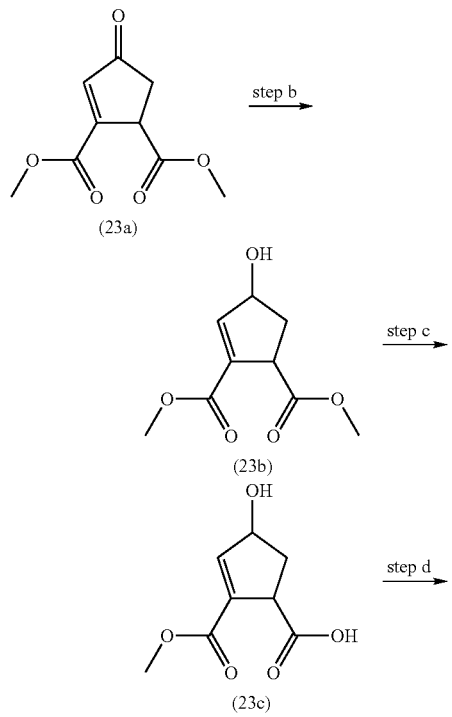

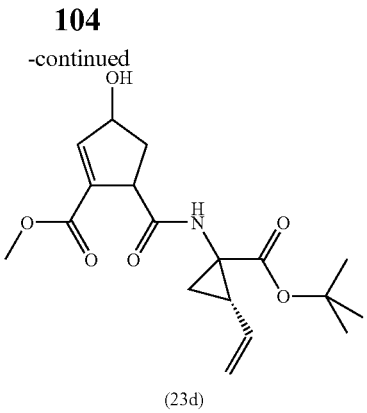

(23d)

Step a: 4-oxocyclopent-2-ene-1,2-dicarboxylic acid dimethyl ester (23a)

(1R,2S)-4-oxo-cyclopentane-1,2-dicarboxylic acid dimethyl ester (4.8 g, 23.8 mmol) and CuBr$_2$ (11.9 g, 53.2 mmol) were dissolved in dry THF (70 ml) and the mixture was refluxed for two hours at 90° C. The formed CuBr was filtrated off and the organic phase was concentrated. CaCO$_3$ (2.7 g, 27.2 mmol) and DMF (70 mL) were added and the mixture was held at 100° C. for one hour. The dark brown mixture was poured over ice (35 g) and the formed precipitate was filtrated off. The aqueous layer was extracted with ethyl acetate (1×300 ml+3×150 ml). The organic phases were dried, filtrated and concentrated. Purification by flash chromatography (toluene/EtOAc 9:1) gave the title compound (2.1 g, 45%) as yellow crystals Step b: 4-hydroxy-cyclopent-2-ene-1,2-dicarboxylic acid dimethyl ester (23b)

NaBH$_4$ (0.66 g, 17.5 mmol) dissolved in MeOH (23 mL) was added to a cold solution (−30° C.) of the ketone 23a (3.18 g, 16.1 mmol). After nine minutes the excess of NaBH$_4$ was destroyed by adding brine (80 mL). The mixture was concentrated and extracted with ethyl acetate (4×80 ml). The organic phases were dried, filtrated and concentrated which gave the title compound (3.0 g, 92%) as a yellow oil.

Step c: 4-hydroxy-cyclopent-2-ene-1,2-dicarboxylic acid 2-methyl ester (23c)

LiOH (0.52 g, 22 mmol) was added to an ice-cold solution of the alcohol 23b (3.4 g, 22 mmol) dissolved in dioxane and water (1:1, 110 mL). After two and a half hours the mixture was co-evaporated with toluene and methanol. Purification by flash chromatography (toluene/Ethyl acetate 3:1+1% HOAc) gave the title compound (1.0 g, 27%) as yellow-white crystals.

$^1$H-NMR (300 MHz, CD$_3$OD): δ 1.78-1.89 (m, 1H), 2.70-2.84 (m, 1H), 3.56-3.71 (m, 1H), 3.76 (s, 3H), 4.81-4.90 (m, 1H), 6.76-6.81 (m, 1H); $^{13}$C-NMR (75.5 MHz, CDCl$_3$): δ 38.0, 48.0, 52.4, 75.7, 137.0, 146.2, 165.0 178.4.

Step d: 5-(1-tert-Butoxycarbonyl-2-vinyl-cyclopropylcarbamoyl)-3-hydroxy-cyclopent-1-enecarboxylic acid methyl ester (23d)

Reaction of compound the acid 23c (50 mg, 37 mmol) with (1R,2S)-1-amino-2-vinyl-cyclopropane carboxylic acid tert-butyl ester according to the method described in Example 1 step j, provided the title compound as a slightly yellow oil (50 mg, 38%). $^1$H-NMR (300 MHz, CDCl$_3$): δ [(1.38 & 1.42) s, 9H], 1.75-1.83 (m, 1H), 2.00-2.21 (m, 3H), 3.55-3.63 (m, 1H), [(3.77 & 3.82) s, 3H], 4.20-4.38 (m, 1H), 4.65-4.80 (m, 1H), 5.13-5.20 (m, 1H), 5.22-5.38 (m, 1H), 5.60-5.82 (m, 1H), 6.95-6.96 (m, 2H). Inhibitors of the invention are achieved from the title compound by coupling of the afforded cyclopentenol derivative to a desired pyrimidinol for example as described in Example 3 step f, followed by hydrolysis of the methyl ester using a reagent like LiOH; coupling of a desired alkenylamine and macrocyclisation as described in Example 3 step h and i; hydrolysis of the tert. butyl ester by treatment with for example TFA and finally coupling of a desired sulphone amide derivative for example as described in Example 3, step k.

Example 22

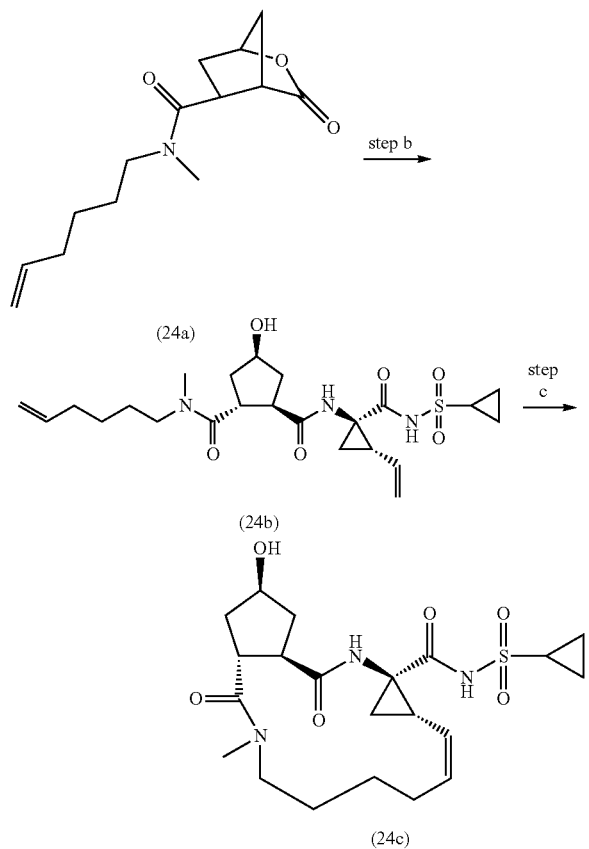

Step a: 3-Oxo-2-oxa-bicyclo[2.2.1]heptane-5-carboxylic acid hex-5-enyl-methylamide (24a)

To HATU (2.17 g, 5.7 mmol) and N-methyl hex-5-enylamine hydrochloride (6.47 mmol) in 5 mL DMF, under argon in an ice bath, were added 1R,4R,5R-3-oxo-2-oxa-bicyclo[2.2.1]heptane-5-carboxylic acid (835.6 mg, 5.35 mmol) in 11 ml DMF followed by DIEA (2.80 ml, 16 mmol). After stirring for 40 min, the mixture was stirred at rt for 5 h. The solvent was evaporated, the residue dissolved in EtOAc (70 mL) and washed with saturated NaHCO$_3$ (10 ml). The aqueous phase was extracted with EtOAc (2×25 ml). The organic phases were combined, washed with saturated NaCl (20 mL), dried over Na$_2$SO$_4$, and evaporated. Flash column chromatography (150 g silica gel, 2/1 EtOAc-petroleum ether (PE), TLC detection by aqueous KMnO4, Rf 0.55 in 4/1 EtOAc-PE) gave the title compound as a yellow oil (1.01 g, 75%).

Step b: N-(1-Cyclopropanesulfonylaminocarbonyl-2-vinyl-cyclopropyl)-2-(hex-5-enyl-methyl-aminocarbonyl)-4-hydroxy-cyclopentane-carboxamide (24b)

LiOH solution (0.15M, 53 mL, 8 mmol) was added to the lactone amide 24a (996 mg, 3.96 mmol) in an ice bath and stirred for 1 h. The mixture was acidified to pH 2-3 with 1N HCl and evaporated, co-evaporated with toluene several times, and dried under vacuum overnight. (1R,2S)-cyclopropanesulfonic acid (1-amino-2-vinyl-cyclopropane-carbonyl) amide hydrochloride (4.21 mmol) and HATU (1.78 g, 4.68 mmol) were added. The mixture was cooled in an ice bath under argon, DMF (25 mL) and then DIEA (2.0 mL, 11.5 mmol) were added. After stirring for 30 min, the mixture was stirred at rt for 3 h. After evaporation of solvent, the residue was dissolved in EtOAc (120 mL), washed successively with 0.5 N HCl (20 mL) and saturated NaCl (2×20 mL), and dried over Na$_2$SO$_4$. Flash column chromatography (200 g YMC silica gel, 2-4% MeOH in CH$_2$Cl$_2$ gave white solids (1.25 g, 66%).

Step c: Cyclopropanesulfonic acid (17-hydroxy-13-methyl-2,14-dioxo-3,13-diaza-tricyclo[13.3.0.0*4,6*]octadec-7-ene-4-carbonyl)-amide (24c)

The cyclopentanol 24b (52.0 mg, 0.108 mmol) was dissolved in 19 ml 1,2-dichloroethane (bubbled with argon prior to use). The Hoveyda-Grubbs $2^{nd}$ generation catalyst (6.62 mg, 10 mole %) was dissolved in DCE (2×0.5 ml) and added. The green solution was bubbled with Ar for 1 min. Aliquots (4 ml each) were transferred into five 2 to 5-ml microwave tubes. To the last tube was added 0.8 mL rinsing with solvent. Each tube was heated by microwave (rt to 160° C. in 5 min). All aliquots were combined and the solvent evaporated. Flash column chromatography (silica gel, 3→7% MeOH in CH$_2$Cl$_2$) gave 24.39 mg solids (Rf 0.28 in 10% MeOH-CH$_2$Cl$_2$ with two spots). The solids were combined with a 9.66-mg sample and subjected to a second chromatography (2→8% MeOH in EtOAc) to give cream solids (23 mg) with 80% of the desired compound (26% yield).

Inhibitors of the invention are achieved from the title compound by coupling of the afforded cyclopentenol derivative to a desired pyrimidinol for example as described in Example 1 step h.

Example 23

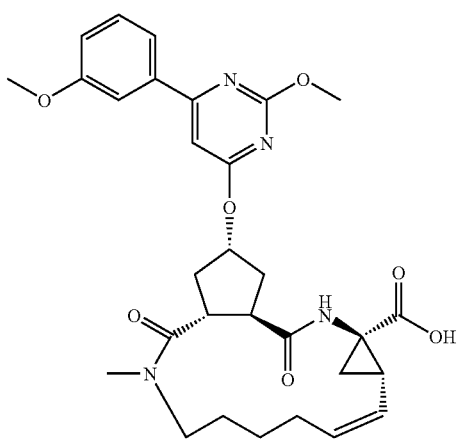 [SMILES: COc1cccc(-c2cc(O[C@@H]3C[C@H]4C(=O)N[C@]5(C(=O)O)C[C@H]5/C=C\CCCCN(C)C(=O)[C@@H]4C3)nc(OC)n2)c1]

17-[2-Methoxy-6-(3-methoxy-phenyl)-pyrimidin-4-yloxy]-13-methyl-2,14-dioxo-3,13-diaza-tricyclo[13.3.0.0*4,6*]octadec-7-ene-4-carboxylic acid (25)

The procedure described in example 16, steps a-f, was followed but using ethyl 3-methoxybenzoyl acetate (9 g, 40 mmol) instead of ethyl 4-methoxybenzoyl acetate in step a, which gave the title compound (305 mg), MS Example 24

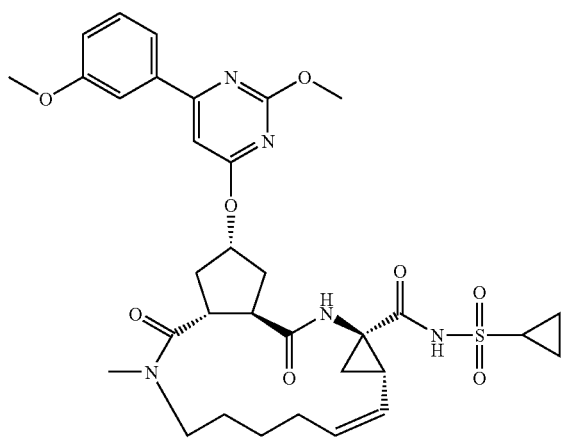 [SMILES: COc1cccc(-c2cc(O[C@@H]3C[C@H]4C(=O)N[C@]5(C(=O)NS(=O)(=O)C6CC6)C[C@H]5/C=C\CCCCN(C)C(=O)[C@@H]4C3)nc(OC)n2)c1]

Cyclopropanesulfonic acid {17-[2-methoxy-6-(3-methoxy-phenyl)-pyrimidin-4-yloxy]-13-methyl-2,14-dioxo-3,13-diaza-tricyclo[13.3.0.0*4,6*]octadec-7-ene-4-carbonyl}-amide (26)

The acid 25 (150 mg, 0.26 mmol) was reacted with cyclopropane sulphonamide (64 mg, 0.53 mmol) according to the procedure described in Example 16 step g, which gave the title compound (110 mg, 62%), MS [M+1] 668.

Example 25

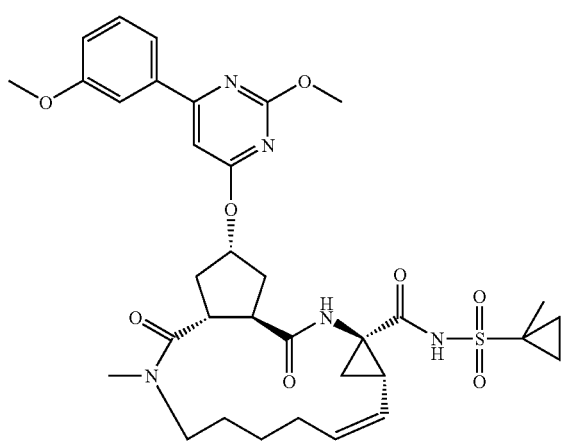

1-Methyl-cyclopropanesulfonic acid {17-[2-methoxy-6-(3-methoxy-phenyl)-pyrimidin-4-yloxy]-13-methyl-2,14-dioxo-3,13-diaza-tricyclo[13.3.0.0*4,6*]octadec-7-ene-4-carbonyl}-amide (27)

The acid 25 (150 mg, 0.26 mmol) was reacted with methylcyclopropane sulphonamide (72 mg, 0.53 mmol) according to the procedure described in Example 16 step g, which gave the title compound (90 mg, 50%), MS [M+1] 682.

Activity of Compounds of Formula (I)

Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion ($neo^R$, neomycine phosphotransferase). The construct is bordered by 5' and 3' NTRs (non-translated regions) from HCV type 1b. Continued culture of the replicon cells in the presence of G418 ($neo^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease by 50% the level of detected luciferase activity, or more specifically, the ability of the genetically linked HCV replicon RNA to replicate.

Inhibition Assay

The aim of this in vitro assay is to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-NH$_2$ (AnaSpec, San José, USA), was measured spectrofluorometrically in the presence of a peptide cofactor, KKGSVVIVGRIVLSGK (Åke Engström, Department of Medical Biochemistry and Microbiology, Uppsala University, Sweden). [Landro, 1997 #Biochem 36 9340-9348]. The enzyme (1 nM) was incubated in 50 mM HEPES, pH 7.5, 10 mM DTT, 40% glycerol, 0.1% n-octyl-D-glucoside, with 25 μM NS4A cofactor and inhibitor at 30° C. for 10 min, whereupon the reaction was initiated by addition of 0.5 μM substrate. Inhibitors were dissolved in DMSO, sonicated for 30 sec. and vortexed. The solutions were stored at −20° C. between measurements.

The final concentration of DMSO in the assay sample was adjusted to 3.3%. The rate of hydrolysis was corrected for inner filter effects according to published procedures.

[Liu, 1999 Analytical Biochemistry 267 331-335]. Ki values were estimated by non-linear regression analysis (GraFit, Erithacus Software, Staines, MX, UK), using a model for competitive inhibition and a fixed value for Km (0.15 μM). A minimum of two replicates was performed for all measurements.

Compounds of the invention are preferably potent against wild type virus and mutant HCV virus, especially virus comprising drug escape mutations. Drug escape mutations are those arising in patients due to the selective pressure of a prior art anti viral and which confer enhanced resistance to that antiviral.

The inhibition of certain mutant HCV exhibited by the compounds of the invention can be determined as described in WO2004/039970.

A156T and D168V are particularly relevant drug escape mutants in the context of HCV therapy using NS3 protease inhibitors and compounds of the invention preferably have low Ki values against these mutants.

The following Table 1 lists representative compounds that were prepared according to the above examples. The activities of the compounds tested are also depicted in Table 1. The legend for values A, B, C, D, E, and F is as follows:

value A corresponds to an $EC_{50}$>10 μM;

value B corresponds to an $EC_{50}$ between 10 μM and 1 μM;

value C corresponds to an $EC_{50}$ between 0.99 μM and 200 nM;

value D corresponds to an $EC_{50}$ between 199 nM and 0.5 nM.

value E corresponds to a Ki>1 μM;

value F corresponds to a Ki between 1 μM and 100 nM;

value G corresponds to a Ki between 99.9 nM and 5 nM;

value H corresponds to a Ki between 4.9 nM and 0.1 nM.

| Example nr. | $EC_{50}$ Replicon assay | Ki Enzymatic assay |
|---|---|---|
| Example 1 | B | H |
| Example 2 | B | H |
| Example 3 | B | G |
| Example 4 | C | H |
| Example 5 | A | F |
| Example 6 | D | H |
| Example 7 | D | H |
| Example 9 | B | n.d. |
| Example 10 | A | E |
| Example 11 | A | G |
| Example 12 | A | G |
| Example 14 | C | G |
| Example 16 | C | H |
| Example 17 | C | H |
| Example 24 | D | |
| Example 25 | D | |

The invention claimed is:

1. A compound of the formula I:

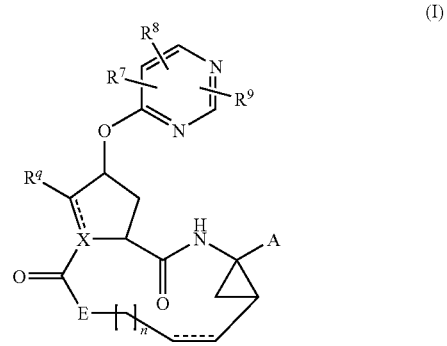

wherein:
A is —C(=O)OR$^1$, —C(=O)—NH—SO$_2$—R$^2$, wherein;
R$^1$ is hydrogen; or C$_{1-6}$alkyl;
R$^2$ is C$_{3-7}$cycloalkyl, phenyl; or thiazolyl or pyridyl, any of which is optionally substituted with one or two substituents selected from C$_{1-6}$alkyl, C$_{1-6}$alkoxy, trifluoromethyl, and halo;
X is N, CH and when X bears a double bond it is C;
R$^q$ is hydrogen, or where X is C or CH, R$^q$ may also be C$_{1-6}$alkyl;
E is NR$^5$;
R$^5$ is hydrogen, C$_{1-6}$alkyl, C$_{1-6}$alkoxyC$_{1-6}$alkyl, or C$_{3-7}$cycloalkyl;
n is 3, 4, 5 or 6;
each dotted line ----- independently represents an optional double bond;
each aryl independently is phenyl optionally substituted with one, two or three substituents selected from halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, amino, mono- or diC$_{1-6}$alkylamino, azido, mercapto, C$_{1-6}$alkylthio, polyhaloC$_{1-6}$alkyl, polyhaloC$_{1-6}$alkoxy, C$_{3-7}$cycloalkyl, and Het$^1$;
each Het independently is a 5 or 6 membered saturated, partially unsaturated or completely unsaturated heterocyclic ring containing 1, 2, 3 or 4 heteroatoms each independently selected from nitrogen, oxygen and sulfur, said heterocyclic ring being optionally substituted with one, two or three substituents each independently selected from halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, amino, mono- or diC$_{1-6}$alkylamino, azido, mercapto, polyhaloC$_{1-6}$alkyl, polyhaloC$_{1-6}$alkoxy, C$_{3-7}$cycloalkyl, Het$^1$;
each Het$^1$ independently is pyrrolidinyl, piperidinyl, piperazinyl, 4-C$_{1-6}$alkyl-piperazinyl, 4-C$_{1-6}$alkylcarbonyl-piperazinyl, and morpholinyl and wherein the morpholinyl and piperidinyl groups may optionally substituted with one or two C$_{1-6}$alkyl radicals;
wherein the pyrimidinyl radical

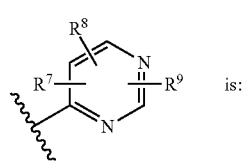 is:

-continued

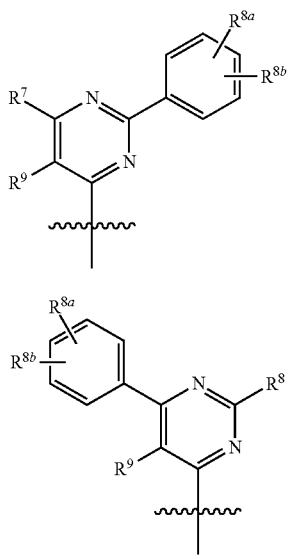

(a-1)

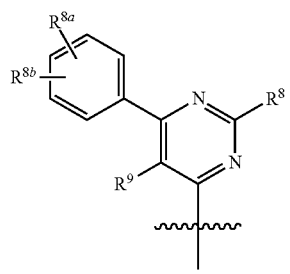

(a-2)

wherein R$^7$ and R$^8$ independently are phenyl or C$_{1-6}$alkoxy; R$^9$ is hydrogen or C$_{1-6}$alkyl;

each R$^{8a}$ or R$^{8b}$ independently is hydrogen, C$_{1-6}$alkoxy or a stereoisomer, N-oxide or pharmaceutically acceptable addition salt thereof.

2. A compound of claim 1, wherein n is 4 or 5.

3. A compound of claim 1 or 2, wherein ----- adjacent the —(CH$_2$)$_n$— moiety is a double bond.

4. A compound of claim 1 or 2, wherein ----- in the five membered ring having X is a single bond and R$^q$ is hydrogen.

5. A compound of claim 1, wherein X is N.

6. A compound of claim 1, wherein A is —C(=O)—NH—SO$_2$R$^2$; and R$^2$ is C$_{3-7}$cycloalkyl, phenyl; or thiazolyl or pyridyl, either of which is optionally substituted with one or two substituents selected from C$_{1-6}$alkyl, C$_{1-6}$alkoxy, trifluoromethyl, and halo.

7. A compound of claim 1, wherein A is C(=O)OR$^1$ wherein R$^1$ is hydrogen or methyl.

8. A composition comprising the compound of claim 1 in a pharmaceutically acceptable carrier.

9. A method of treating hepatitis C virus infections comprising administering to a human in need of such treatment, a compound of claim 1.

10. The composition of claim 8 having another antiviral compound.

11. A composition according to claim 10 wherein the other antiviral compound is an anti-HCV compound.

12. A compound according to claim 1, wherein C$_{1-6}$alkyl is methyl, C$_{1-6}$alkoxy is methoxy, and halo is fluoro or chloro.

13. A compound according to claim 6, wherein C$_{1-6}$alkyl is methyl and halo is fluoro or chloro.

* * * * *